(12) United States Patent
Shen et al.

(10) Patent No.: US 8,669,374 B2
(45) Date of Patent: *Mar. 11, 2014

(54) FUNCTIONALIZED CYANINE DYES (PEG)

(76) Inventors: Gene Shen, Santa Clara, CA (US);
Stephen Yue, Eugene, OR (US)

( * ) Notice: Subject to any disclaimer, the term of this patent is extended or adjusted under 35 U.S.C. 154(b) by 105 days.

This patent is subject to a terminal disclaimer.

(21) Appl. No.: 13/218,395

(22) Filed: Aug. 25, 2011

(65) Prior Publication Data

US 2012/0058482 A1    Mar. 8, 2012

Related U.S. Application Data

(60) Provisional application No. 61/377,004, filed on Aug. 25, 2010, provisional application No. 61/377,022, filed on Aug. 25, 2010, provisional application No. 61/377,031, filed on Aug. 25, 2010, provisional application No. 61/377,038, filed on Aug. 25, 2010, provisional application No. 61/377,048, filed on Aug. 25, 2010.

(51) Int. Cl.
*C07D 209/02* (2006.01)
*C12Q 1/68* (2006.01)
*G01N 33/53* (2006.01)

(52) U.S. Cl.
USPC ............... 548/455; 435/6.1; 435/7.1; 435/7.2

(58) Field of Classification Search
USPC .............................. 548/455; 435/6.1, 7.1, 7.2
See application file for complete search history.

(56) References Cited

U.S. PATENT DOCUMENTS

| | | |
|---|---|---|
| 4,711,955 A | 12/1987 | Ward et al. |
| 5,106,990 A | 4/1992 | Ohno et al. |
| 5,627,027 A | 5/1997 | Waggoner |
| 5,688,648 A | 11/1997 | Mathies et al. |
| 5,808,044 A | 9/1998 | Brush et al. |
| 5,986,086 A | 11/1999 | Brush et al. |
| 6,114,350 A | 9/2000 | Randall et al. |
| 6,197,956 B1 | 3/2001 | Randall et al. |
| 6,224,644 B1 | 5/2001 | Randall et al. |
| 6,255,083 B1 | 7/2001 | Williams |
| 6,265,193 B1 | 7/2001 | Brandis et al. |

(Continued)

FOREIGN PATENT DOCUMENTS

| | | |
|---|---|---|
| JP | 2000-094834 A | 4/2000 |
| WO | WO 2005-033245 A1 | 4/2005 |

(Continued)

OTHER PUBLICATIONS

Akeson, M. et al., "Microsecond time-scale discrimination among polycytidylic acid, polyadenylic acid, and polyuridylic acid as homopolymers or as segments within single RNA molecules," *Biophys, J.*, 77:3227-3233 (1999).

(Continued)

*Primary Examiner* — Jezia Riley
(74) *Attorney, Agent, or Firm* — Morgan, Lewis & Bockius LLP

(57) ABSTRACT

The invention provides a novel class of cyanine dyes that are functionalized with a linker moiety that facilitates their conjugation to other species and substituent groups which increase the water-solubility, and optimize the optical properties of the dyes. Also provided are conjugates of the dyes, methods of using the dyes and their conjugates and kits including the dyes and their conjugates.

31 Claims, 8 Drawing Sheets

(56) References Cited

U.S. PATENT DOCUMENTS

| | | |
|---|---|---|
| 6,331,632 B1 | 12/2001 | Reedy et al. |
| 6,399,335 B1 | 6/2002 | Kao et al. |
| 6,437,141 B2 | 8/2002 | Randall et al. |
| 6,917,726 B2 | 7/2005 | Levene et al. |
| 7,013,054 B2 | 3/2006 | Levene et al. |
| 7,033,764 B2 | 4/2006 | Korlach et al. |
| 7,041,812 B2 | 5/2006 | Kumar et al. |
| 7,052,839 B2 | 5/2006 | Nelson et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,170,050 B2 | 1/2007 | Turner et al. |
| 7,181,122 B1 | 2/2007 | Levene et al. |
| 7,223,541 B2 | 5/2007 | Fuller et al. |
| 7,292,742 B2 | 11/2007 | Levene et al. |
| 7,302,146 B2 | 11/2007 | Turner et al. |
| 7,393,640 B2 | 7/2008 | Kumar et al. |
| 2002/0156288 A1 | 10/2002 | Caputo et al. |
| 2006/0240439 A1 | 10/2006 | Smith et al. |
| 2006/0281109 A1 | 12/2006 | Ost et al. |
| 2007/0072196 A1 | 3/2007 | Xu et al. |
| 2007/0099212 A1 | 5/2007 | Harris |
| 2007/0104649 A1 | 5/2007 | Fischer et al. |
| 2008/0267883 A1 | 10/2008 | Rajopadhye et al. |
| 2009/0269759 A1 | 10/2009 | Menchen et al. |
| 2009/0275036 A1 | 11/2009 | Hardin et al. |
| 2010/0323389 A1* | 12/2010 | Xu et al. ............ 435/29 |
| 2011/0313129 A1 | 12/2011 | Hu et al. |

FOREIGN PATENT DOCUMENTS

| | | |
|---|---|---|
| WO | WO 2006-111726 A1 | 10/2006 |
| WO | WO 2012-054749 A1 | 4/2012 |
| WO | WO 2012-054784 A1 | 4/2012 |

OTHER PUBLICATIONS

Braslavsky, I. et al., "Sequence information can be obtained from single DNA molecules," *Proc. Natl. Acad. Sci. USA*, 100:3960-3964 (2003).

Eid. J., "Real-Time DNA Sequencing from Single Polymerase Molecules," Science, vol. 323, p. 133-138, 2009.

Jett, J. H. et al., "High-speed DNA sequencing: An approach based upon fluorescence detection of single molecules," *J. Biomol. Struct. Dynamics*, 7:301-309 (1989).

Lagerqvist, J. et al., "Fast DNA sequencing via transverse electronic transport," *Nano Lett.*, 6:779-782 (2006).

Levene, M. J. et al., "Zero-mode waveguides for single-molecule analysis at high concentrations," *Science*, 299:682-686 (2003).

Metzker, M. L., "Emerging Technologies in DNA Sequencing," *Genome Res.*, 15:1767-1776 (2005).

Rhee, K. J. et al., "Predicting the utilization of helicopter emergency medical services: an approach based on need," *Annals of emergency medicine*, 13:916-923 (1984).

Stephan, J. et al., "Towards a general procedure for sequencing single DNA molecules," *J. Biotechnol.*, 86:255-267 (201).

Wang, Li, et al., "Novel Asymmetric Cy5 Dyes: Synthesis, Photostabilities and High Sensitivity in Protein Fluorescene Labeling," J. of Photochem. and Photobio. A: Chem., vol. 210, p. 168-172, 2010.

Werner, J. H. et al., "Progress towards single-molecule DNA sequencing: a one color demonstration," *J. Biotechnol.*, 102:1-14 (2003).

* cited by examiner

| Entry # | R1 | R2 | R3 | R4 | R5 | R6 | R7 | R1' | R2' | R3' | R4' | R5' | R6' | absorption |
|---|---|---|---|---|---|---|---|---|---|---|---|---|---|---|
| 1 | H | H | SO$_3$H | H | D | D | L | H | H | SO$_3$H | H | D | D | 650 nm |
| 2 | H | H | SO$_3$H | H | D | D | L | H | H | SO$_3$H | H | D | D | 653 nm |
| 3 | H | H | SO$_3$H | H | D | D | M | H | H | SO$_3$H | H | D | D | 650 nm |
| 4 | H | H | SO$_3$H | H | D | CH$_3$ | M | H | H | SO$_3$H | H | D | D | 650 nm |
| 5 | H | H | SO$_3$H | H | D | CH$_3$ | M | H | H | SO$_3$H | H | D | D | 645 nm |
| 6 | H | A | H | A | D | CH$_3$ | M | H | A | H | A | D | CH$_3$ | 638 nm |
| 7 | H | A | H | A | D | CH$_3$ | P | H | A | H | A | D | CH$_3$ | 640 nm |
| 8 | | | | | | | | | | | | | | |

FIGURE 3(b)

| Entry # | R1 | R2 | R3 | R4 | R5 | R6 | R7 | R1' | R2' | R3' | R4' | R5' | R6' | absorption |
|---|---|---|---|---|---|---|---|---|---|---|---|---|---|---|
| 1 | H | SO₃H | H | SO₃H | D | CH₃ | M | H | SO₃H | H | SO₃H | D | CH₃ | 672 nm |
| 2 | H | SO₃H | H | SO₃H | D | D | M | H | SO₃H | H | SO₃H | D | D | 680 nm |
| 3 | H | SO₃H | H | SO₃H | D | D | M | H | SO₃H | H | SO₃H | D | D | 678 nm |
| 4 | H | SO₃H | H | SO₃H | D | CH₃ | N | H | SO₃H | H | SO₃H | D | CH₃ | 666 nm |
| 5 | | | | | | | | | | | | | | |
| 18 | | | | | | | | | | | | | | |

FUNCTIONALIZED CYANINE DYES (PEG)

CROSS-REFERENCE TO RELATED APPLICATIONS

This application claims priority to U.S. Provisional Application Nos. 61/377,004, filed on Aug. 25, 2010, 61/377,022, filed on Aug. 25, 2010, 61/377,031, filed on Aug. 25, 2010, 61/377,038, filed on Aug. 25, 2010, and 61/377,048, filed on Aug. 25, 2010 the disclosures of which are incorporated herein by reference in their entirety for all purposes:

BACKGROUND OF THE INVENTION

1. Field of Invention

The present invention relates generally to the synthesis of fluorescent compounds that are analogues of cyanine dyes. The compounds of the invention are fluorophores that are derivatized to allow their facile attachment to another moiety. The invention also relates to improved methods for sequencing and genotyping nucleic acid in a single molecule configuration. An exemplary method involves detection of single molecules of fluorescent labels released from a nucleic acid during synthesis of an oligonucleotide.

2. Background

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, saccharides, pharmaceuticals, metabolites, microorganisms and other materials of diagnostic value. Examples of such materials include narcotics and poisons, drugs administered for therapeutic purposes, hormones, pathogenic microorganisms and viruses, peptides, e.g., antibodies and enzymes, and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations. However, such labels are expensive, hazardous, and their use requires sophisticated equipment and trained personnel. Thus, there is wide interest in non-radioactive labels, particularly in labels that are observable by spectrophotometric, spin resonance, and luminescence techniques, and reactive materials, such as enzymes that produce such molecules.

Labels that are detectable using fluorescence spectroscopy are of particular interest because of the large number of such labels that are known in the art. Moreover, as discussed below, the literature is replete with syntheses of fluorescent labels that are derivatized to allow their attachment to other molecules, and many such fluorescent labels are commercially available.

Fluorescent nucleic acid probes are important tools for genetic analysis, in both genomic research and development, and in clinical medicine. As information from the Human Genome Project accumulates, the level of genetic interrogation mediated by fluorescent probes will expand enormously. One particularly useful class of fluorescent probes includes self-quenching probes, also known as fluorescence energy transfer probes, or FET probes. The design of different probes using this motif may vary in detail. In an exemplary FET probe, both a fluorophore and a quencher are tethered to a nucleic acid. The probe is configured such that the fluorophore is proximate to the quencher and the probe produces a signal only as a result of its hybridization to an intended target. Despite the limited availability of FET probes, techniques incorporating their use are rapidly displacing alternative methods.

To enable the coupling of a fluorescent label with a group of complementary reactivity on a carrier molecule, a reactive derivative of the fluorophore is prepared. For example, Reedy et al. (U.S. Pat. No. 6,331,632) describe cyanine dyes that are functionalized at an endocyclic nitrogen of a heteroaryl moiety with hydrocarbon linker terminating in a hydroxyl moiety. The hydroxyl moiety is converted to the corresponding phosphoramidite, providing a reagent for conjugating the cyanine dye to a nucleic acid. Waggoner (U.S. Pat. No. 5,627,027) has prepared derivatives of cyanine and related dyes that include a reactive functional group through which the dye is conjugated to another species. The compounds set forth in Ohno et al. (U.S. Pat. No. 5,106,990) include cyanine dyes that have a $C_1$-$C_5$ hydrocarbyl linker terminated with a sulfonic acid, a carboxyl or a hydroxyl group. Randall et al. (U.S. Pat. Nos. 6,197,956; 6,114,350; 6,224,644; and 6,437,141) disclose cyanine dyes with a linker arm appended to an endocyclic heteroaryl nitrogen atom. The linkers include a thiol, amine or hydroxyl group, or a protected analogue of these residues. Additional linker arm-cyanine dyes are disclosed by Brush et al. (U.S. Pat. Nos. 5,808,044; 5,986,086). These cyanine dyes are derivatized at both endocyclic heteroaryl nitrogen atoms with a hydrocarbyl linker terminating in a hydroxyl moiety. One hydroxyl moiety is converted to the corresponding phosphoramidite and the other is protected as a dimethoxytrityl ether.

Cyanine dyes are particularly popular fluorophores and are widely used in many biological applications due to their high quantum yield and high molar absorbtivity. Cyanine dyes are, however, susceptible to photobleaching during prolonged excitation. Moreover, due the rigid planar structure of these compounds, they have a tendency to stack and self-quench. Thus, provision of cyanine dyes having an enhanced brightness and decreased tendency to stack, thereby mitigating the effects of photobleaching and stacking is an important object. Furthermore, cyanine dyes that are hydrophilic are less attracted to other species such as proteins and surfaces, which reduces adventitious binding of the fluorophore and enhances the precision and accuracy of assays and other analyses utilizing cyanine fluorophores. The present invention meets these objects and other needs.

SUMMARY OF THE INVENTION

The present invention provides a class of cyanine-based fluorophores modified to improve their fluorescent and other physicochemical properties. Thus, it is a general object of the invention to provide cyanine dyes that are hydrophilic, are resistant to photobleaching, or maintain a high level of brightness despite photobleaching, and have a lower tendency to stack or otherwise aggregate than current cyanine fluorophores.

Exemplary dyes of the invention find particular use in DNA sequencing modalities, particularly single molecule sequencing modalities. Previous dyes used in such applications have had less than ideal properties. For example, certain dyes give suboptimal performance, because, as was discovered, the dyes are insufficiently hydrophilic, insufficiently bright, do not emit steadily (i.e., blink), undergo photobleaching upon prolonged irradiation or they aggregate. These deficiencies can cause misreads in DNA sequencing analyses, providing inaccurate results. In various embodiments, the present invention provides a solution to one or more of these factors contributing to suboptimal dye performance. In various embodiments, the hydrophilicity of the dyes is enhanced by the addition to the cyanine core or a side group attached to the cyanine core of a water-soluble polymer, sulfonic acid, or carboxylic acid moieties or groups containing sulfonic acid or carboxylic acid moieties. Moreover, it was discovered that substitution of a cyanine dye with charged, hydrophilic moieties protects the cyanine chromophore from the dye's microenvironment and reduces blinking, aggregation and photobleaching. Thus, in various embodiments, the dyes are brighter, more photostable and their emission is more constant. Furthermore, for DNA sequencing, particularly single molecule sequencing, resolution of the absorbance of the dye emissions is important to sensitivity and accuracy of the measurements underlying the sequence determination. Accordingly, in various embodiments, the present invention provides dyes with emissions tuned to achieve useful levels of resolution in the emission peaks of the dyes when they are used in combinations of 2, 3, 4 or more different dyes attached to nucleic acids. Thus, in various embodiments, the present invention provides a solution to the problem. In exemplary embodiments, the dyes of the invention provide at least a 2%, at least a 5%, at least a 7% or at least a 10% improvement in readlength in a single molecule DNA sequencing protocol when compared with dyes that are not functionalized as are the dyes of the invention.

In exemplary embodiments, the dyes of the invention are utilized in DNA sequencing in real time using a single polymerase enzyme attached to the bottom of the small nanometer size hole called zero-mode waveguide (ZMW). Fluorescent signals of 4 different colors that correspond to 4 different DNA bases: A, G, C, T are detected. Since the most robust methodologies read through as many bases on a template oligonucleotide as possible, it is desirable to utilize dyes that do not limit the readlength or the accuracy of the measurements. The water-soluble, cyanine dyes of the invention are of use in such measurements and in some embodiments increase the accuracy of the measurements by at least 2%, at least 5%, at least 7% or at least 10% in a single molecule DNA sequencing protocol when compared with dyes that are not functionalized as are the dyes of the invention.

In an exemplary embodiment, the invention provides cyanine dyes derivatized with a water-soluble polymer and/or multiple ionizable groups such as sulfonic or carboxylic acids. Exemplary fluorophores of the invention also include within their structure(s) a versatile linker arm, the structure and position of which is readily alterable, thereby allowing the conjugation of the label through a variety of positions on the cyanine nucleus to a carrier molecule. The cyanine-based labels are readily attached to a label, such as a nucleic acid, using techniques well known in the art, or modifications of such techniques that are well within the abilities of those of ordinary skill in the art. The versatility of the labels set forth herein provides a marked advantage over currently utilized cyanine labels, probes assembled using those labels and methods relying upon such labels and probes. Moreover, the present invention provides a class of chemically versatile labels in which the fluorophore can be engineered to have a desired light excitation and emission profile.

In a first aspect, the present invention provides a fluorescent compound having the formula:

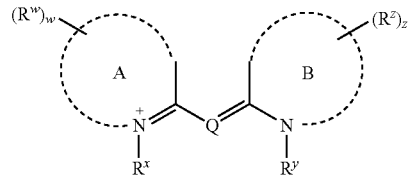

A and B independently selected monocyclic, bicyclic or polycyclic aryl or heteroaryl moieties. When A and/or B is a bicyclic polycyclic moiety, two or more of the rings are optionally fused. Exemplary polycyclic moieties include indole and benzoindole. Q is a substituted or unsubstituted methine moiety (e.g., —(CH=C(R))$_c$—CH=), in which c is an integer selected from 1, 2, 3, 4, or 5 and R is an "alkyl group substituent" as defined herein. When two or more R groups are present, they are optionally joined to form a ring. Each $R^w$, $R^x$, $R^y$ and $R^z$ is independently selected from those substituents set forth in the Definitions section herein as "alkyl group substituents" and "aryl group substituents." The indices w and z are independently selected from the integers from 0 to 6. In an exemplary embodiment, at least one of $R^w$, $R^x$, $R^y$ and $R^z$ is C(O)NR°(CH$_2$)$_h$G in which G is a member selected from SO$_3$H and CO$_2$H, R° is H or substituted or unsubstituted alkyl or heteroalkyl and the index h is an integer from 1 to 20. In exemplary embodiments, at least 1, 2, 3, 4, 5, or 6 of $R^x$, $R^y$, $R^w$ and $R^z$ are alkylsulfonic acid or heteroalkylsulfonic acid and at least one of these moieties is alkylcarboxylic acid or heteroalkylcarboxylic acid. In exemplary embodiments, at least one of $R^w$, $R^x$, $R^y$ and $R^z$ includes a water-soluble polymer (e.g., poly(ethylene glycol)) component.

In various embodiments, at least one of $R^w$, $R^y$ and $R^z$ is functionalized with an additional dye moiety bonded to the cyanine dye core shown above. In an exemplary embodiment, the additional dye moiety is bonded to the dye core through a linker, a polyvalent scaffold, or a linker-polyvalent scaffold conjugate.

In a further aspect, the invention provides a method of monitoring an enzyme reaction. The method generally comprises providing a reaction mixture comprising the enzyme and at least a first reactant composition. An exemplary reactant composition comprises a compound having a component that reacts with the enzyme, a fluorescent label component, and an adaptor or linker-adaptor component joining the reactant component to the label component. The reaction mixture is then illuminated to excite the fluorescent label component, and a fluorescent signal from the reaction mixture characteristic of the enzyme reaction is detected.

The invention also provides methods of monitoring nucleic acid synthesis reactions. The methods comprise contacting a polymerase/template/primer complex with a fluorescently labeled nucleotide or nucleotide analog having a nucleotide or nucleotide analog component, a fluorescent label component, and an adaptor or linker-adaptor component joining die nucleotide or nucleotide analog component to the label component. A characteristic signal from the fluorescent dye is then detected that is indicative of incorporation of the nucleotide or nucleotide analog into a primer extension reaction.

In various embodiments, the present invention provides methods of using the compounds described herein for performing nucleic acid analyses, and particularly nucleic acid sequence analyses. In various embodiments, the compounds of the invention are used in single molecule nucleic acid sequencing. Exemplary methods of the invention comprise using a template nucleic acid complexed with a polymerase enzyme in a template dependent polymerization reaction to produce a nascent nucleic acid strand, contacting the polymerase and template nucleic acid with a compound of the invention, and detecting whether or not the compound or a substructure thereof (e.g., a monophosphate nucleic acid) was incorporated into the nascent strand during the polymerization reaction, and identifying a base in the template strand based upon incorporation of the compound. Preferably, the foregoing process is carried out so as to permit observation of individual nucleotide incorporation reactions, through the use of, for example, an optical confinement, that allows observation of an individual polymerase enzyme, or through the use of a heterogeneous assay system, where fluorophores released from incorporated analogs are detected.

The compounds and compositions of the invention are of use in single molecule or single molecule real time DNA sequencing assays. Of particular note in this context is the ability provided by the invention to design fluorophores with selected absorbance and emission properties including wavelength and intensity. The compounds of the invention provide for very versatile assay design. For example, according to the present invention a series of fluorophores of use in an assay are readily designed to have selected absorbance and emission wavelengths and emission intensities, allowing multiple fluorophores to be utilized and distinguished in an assay. In exemplary embodiments, use of compounds of the invention in a multifluorophore assay, e.g., single molecule DNA sequencing, enhances assay performance by at least about 10%, at least about 20% or at least about 30% over a similar assay using currently available fluorophores.

Other aspects, embodiments and objects of the present invention will be apparent from the detailed description that follows.

BRIEF DESCRIPTION OF THE DRAWINGS

FIG. 2(b) is a tabulation of exemplary dyes according to the generic structure of FIG. 2(a).

FIG. 3(b) is a tabulation of exemplary dyes according to the generic structure of FIG. 3(a).

DETAILED DESCRIPTION OF THE INVENTION

Abbreviations

Figure 1A:
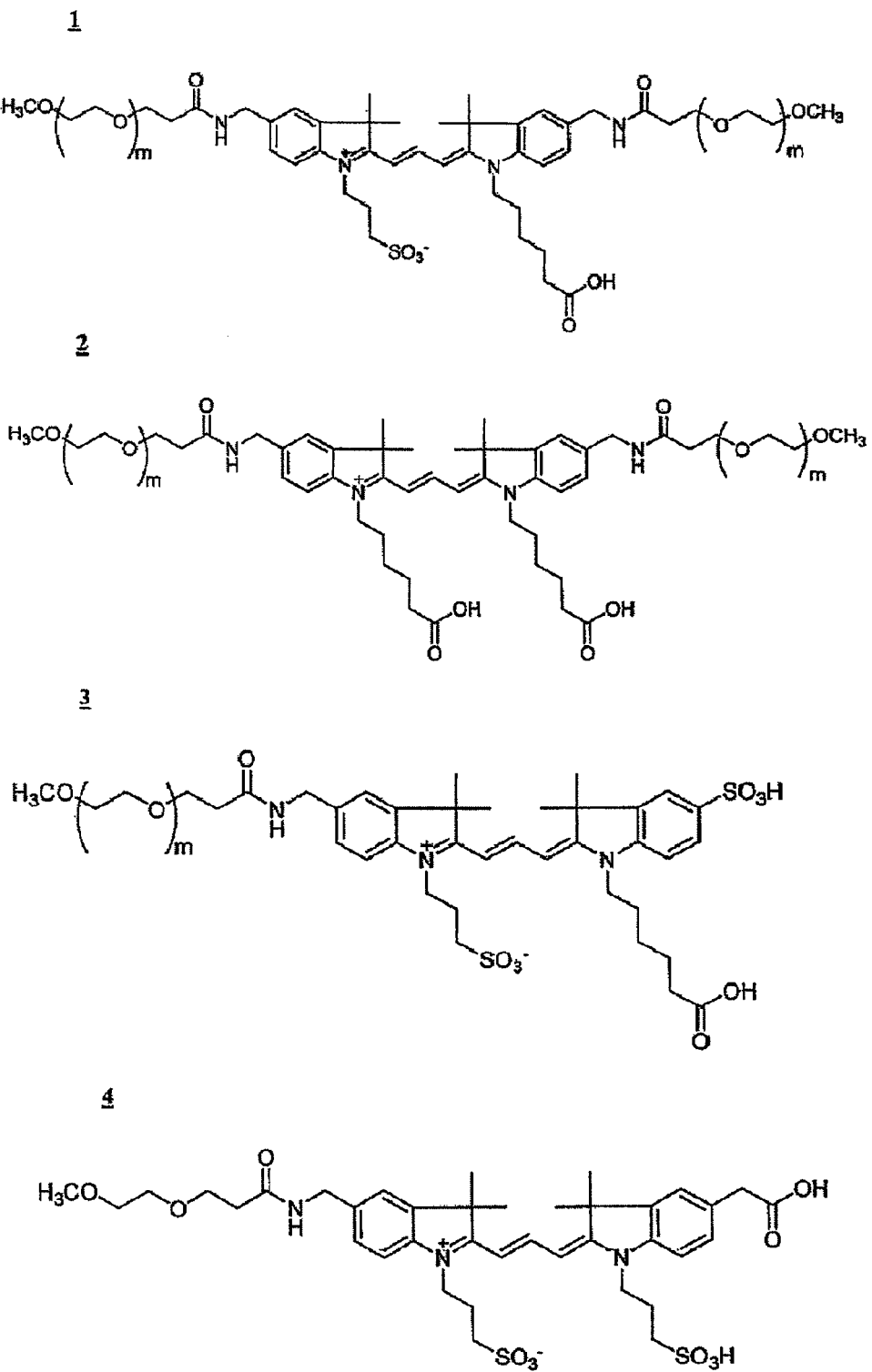
FIG. 1(a through d) displays representative poly(ethylene glycol)-derivatized cyanine dyes of the invention.
Figure 1B:
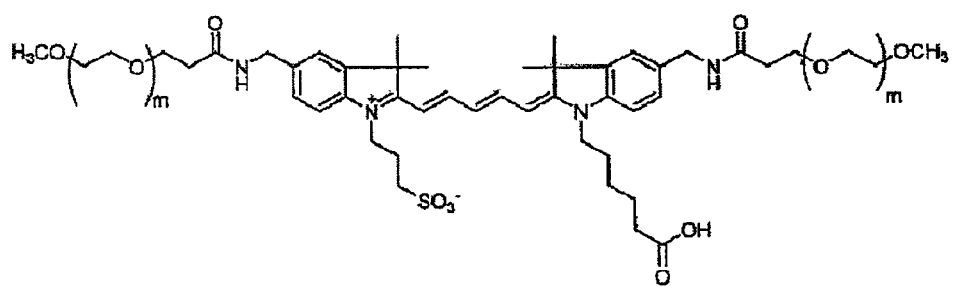
Figure 1B:
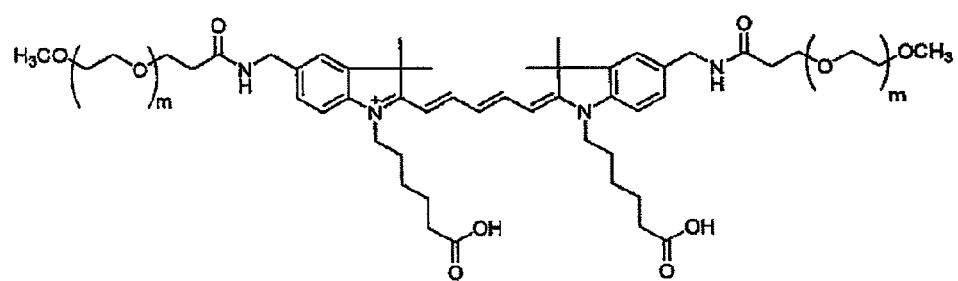
Figure 1B:
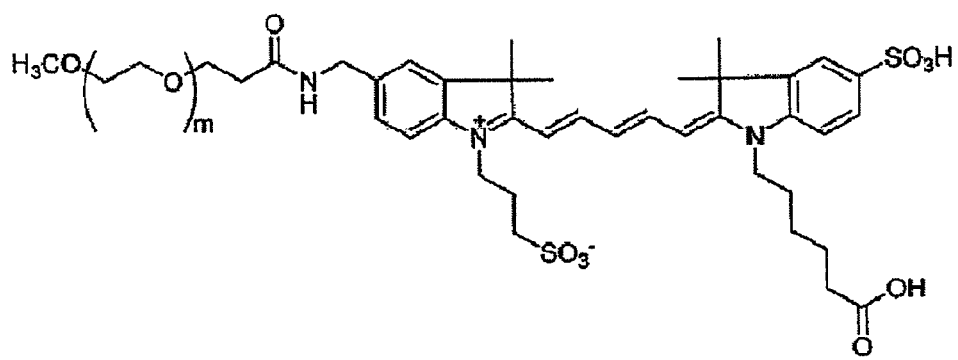
Figure 1C:
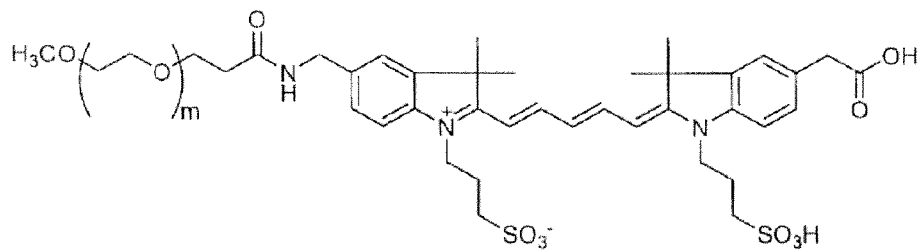
Figure 1C:
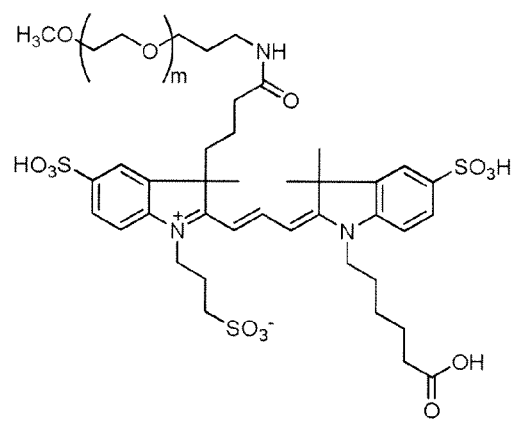
Figure 1C:
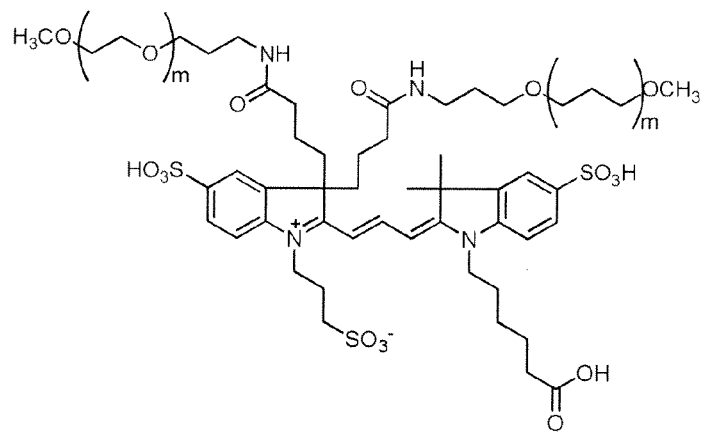
Figure 1D:
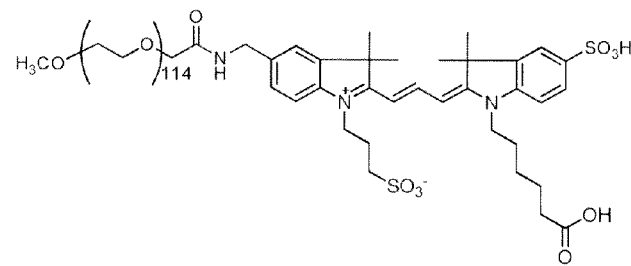
Figure 1D:
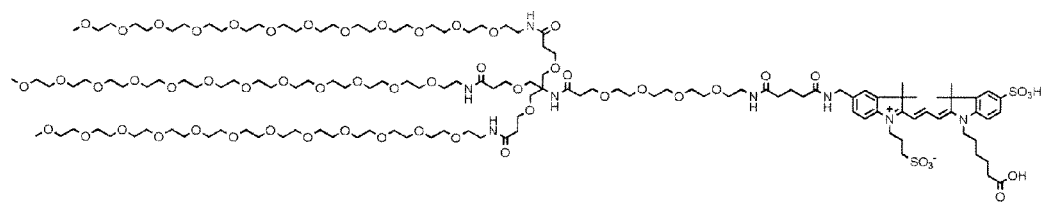
Figure 2A:
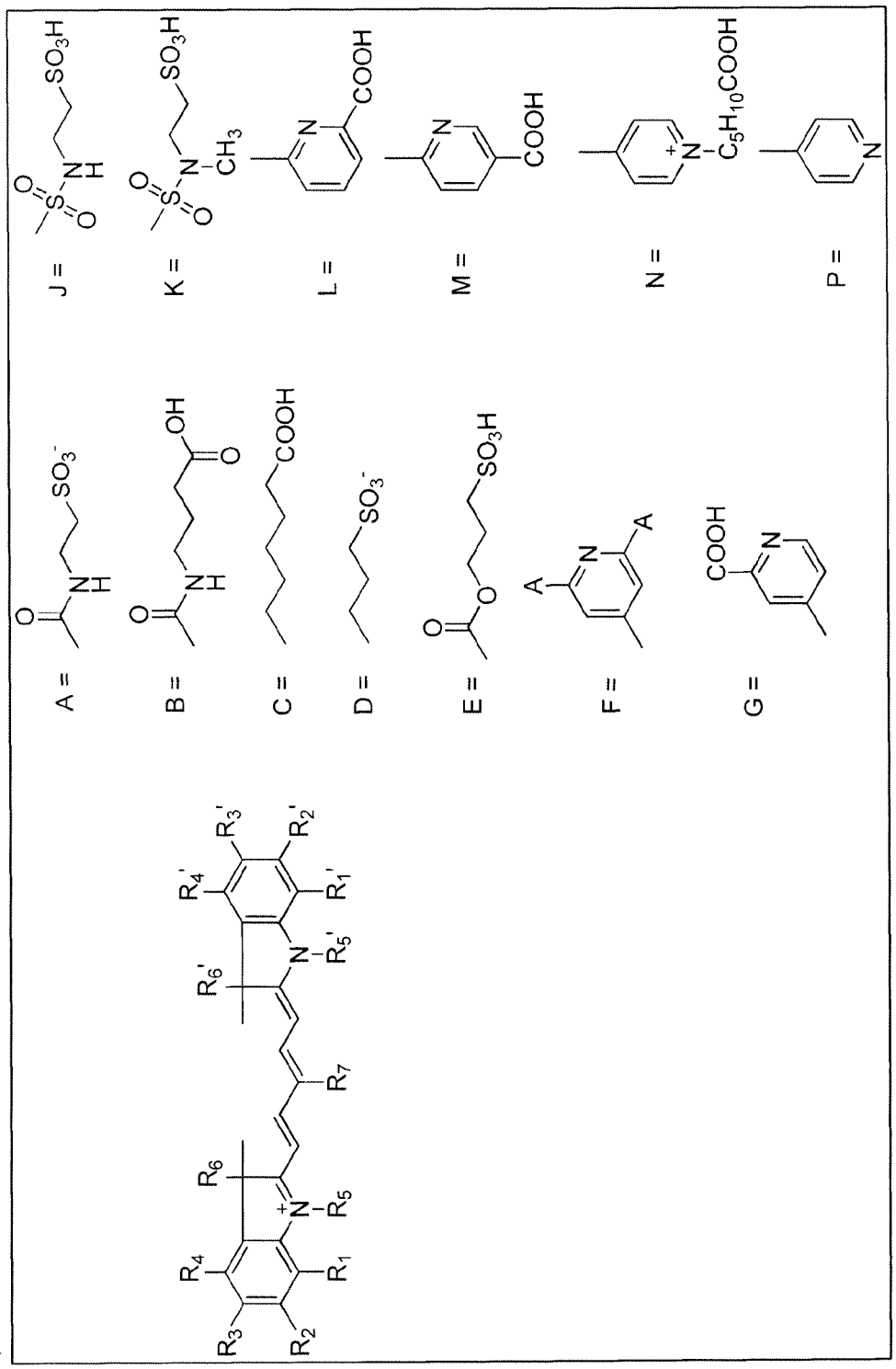
FIG. 2(a) is a generic structure of exemplary dyes of the invention and of substituents on these dyes. When incorporated into a conjugate of the invention, the conjugated dyes can be conjugated to one or more additional species, e.g., a polyvalent scaffold (e.g., into a FRET pair), conjugated to a nucleic acid or to a linker.
Figure 3A:
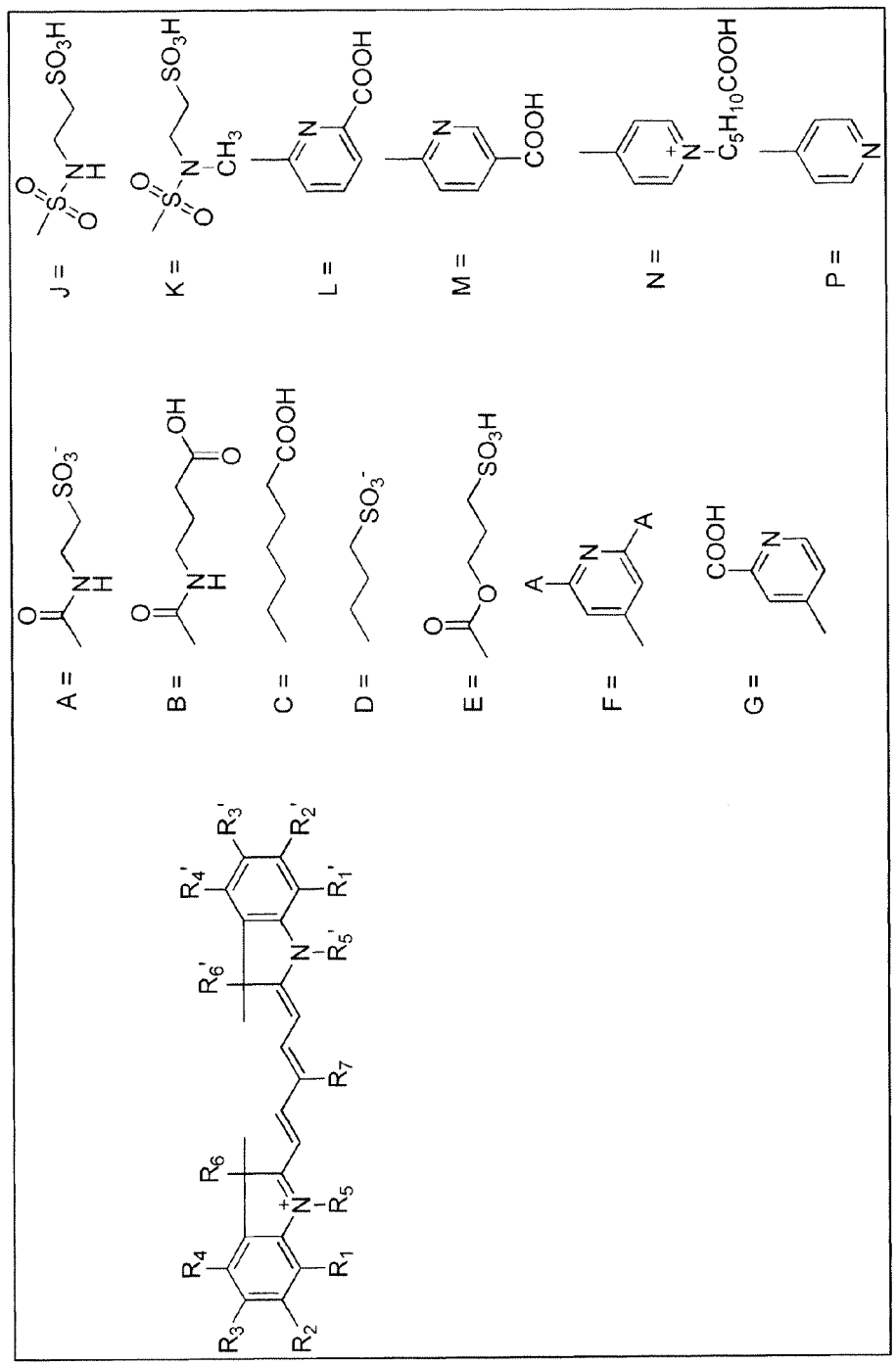
FIG. 3(a) is a generic structure of exemplary dyes of the invention and of substituents on these dyes. When incorporated into a conjugate of the invention, the conjugated dyes can be conjugated to one or more additional species, e.g., a polyvalent scaffold (e.g., into a FRET pair), conjugated to a nucleic acid or to a linker.

"FET", as used herein, refers to "Fluorescence Energy Transfer."

"FRET", as used herein, refers to "Fluorescence Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

Any of the dyes set forth herein can be a component of an FET or FRET pair as either the donor or acceptor. Conjugating a compound of the invention and a donor or acceptor fluorophore through reactive functional groups on the conjugation partners and an appropriate linker, adaptor, carrier molecule or a combination thereof is well within the abilities of those of skill in the art.

The symbol "R", as used herein, refers to moiety which is a member selected from the moieties defined in the following section, e.g., substituted or unsubstituted alkyl, substituted or unsubstituted heteroalkyl, substituted or unsubstituted aryl, substituted or unsubstituted heteroaryl, etc. as well as those groups set forth as substituents of these moieties.

DEFINITIONS

Where chemical moieties are specified by their conventional chemical formulae, written from left to right, they optionally equally encompass the moiety which would result from writing the structure from right to left, e.g., —$CH_2O$— is intended to also recite —$OCH_2$—; —$NHS(O)_2$— is also intended to optionally represent. —$S(O)_2HN$—, etc. Moreover, where compounds can be represented as free acids or free bases or salts thereof, the representation of a particular form, e.g., carboxylic or sulfonic acid, also discloses the other form, e.g., the deprotonated salt form, e.g., the carboxylate or sulfonate salt. Appropriate counterions for salts are well-known in the art, and the choice of a particular counterion for a salt of the invention is well within the abilities of those of skill in the art. Similarly, where the salt is disclosed, this structure also discloses the compound in a free acid or free base form. Methods of making salts and free acids and free bases are well-known in the art.

"Amino Acid," as used herein refers to the genus encompassing hydrophilic amino acids, acidic amino acids, basic amino acids, polar amino acids, hydrophobic amino acids, aromatic amino acids, non-polar amino acids and aliphatic amino acids, including the genus and the species therein. The peptide linkers of the invention are formed from such amino acids. Amino acids also encompass amino-carboxylic acid species other than α-amino acids, e.g., aminobutyric acid (aba), aminohexanoic acid (aha), aminomethylbenzoic acid (amb) etc.

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg I.

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg I and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gin (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (I), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_1$-$C_{21}$)) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

Peptide linkers in the compounds of the invention are formed from amino acids linked by one or more peptide bond. The linkers are formed from oligomers of the same amino acid or different amino acids.

An "Adaptor" is a moiety that is at least bivalent. Exemplary adaptors are bound to a nucleic acid and a fluorescent dye, either directly or through a linker. The adaptor can also be bound to a second fluorescent dye, to a polyvalent scaffold or to a second nucleic acid. When the adaptor is bound to a second dye, either directly or through a polyvalent scaffold, the resulting conjugate is optionally a FRET pair. The adaptor is preferably bound to the phosphorus atom of a phosphate, phosphate ester or polyphosphate moiety of a nucleic acid. In exemplary embodiments, the adaptor is bound through an amide moiety to the dye or to the linker of the linker-dye cassette. The amide moiety is formed between an amine on the adaptor and a carboxyl group on the dye or the linker precursor.

"Cyanine," as used herein, refers to aryl and heteroaryl polymethine dyes such as those based upon the cyanine, merocyanine, styryl and oxonol ring.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. Modifications include, but are not limited to, conjugation into a compound of the invention. Further modifications include those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids. Exemplary nucleic acids of the invention include one or more dye moiety of the invention bound thereto.

Exemplary modified nucleic acids include, but are not limited to, peptide nucleic acids (PNAs), those with phosphodiester group modifications (e.g., replacement of O$^-$ with OR, NR, or SR), 2'-, 3'- and 5'-position sugar modifications, modifications to the nucleobase moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of P(O)O$_3$ with another moiety, methylations, unusual base-pairing combinations such as the isobases, isocytidine and isoguanidine and the like. Nucleic acids can also include non-natural bases, e.g., nitroindole. Non-natural nucleobases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

The nucleic acid can comprise DNA, RNA or chimeric mixtures or derivatives or modified versions thereof. Both the probe and target nucleic acid can be present as a single strand, duplex, triplex, etc. Moreover, as discussed above, the nucleic acid can be modified at the nucleobase moiety, sugar moiety, or phosphate backbone with other groups such as radioactive labels, minor groove binders, intercalating agents, donor and/ or acceptor moieties and the like.

In addition to the naturally occurring "nucleobases," adenine, cytosine, guanine and thymine, nucleic acid components of the compounds of the invention optionally include modified bases. These components can also include modified sugars. For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, nitroindole, and 2,6-diaminopurine. The dye of the invention or another probe component can be attached to the modified base.

In another embodiment, the nucleic acid comprises at least one modified sugar moiety selected from the group including, but not limited to, arabinose, 2-fluoroarabinose, xylulose, and hexose. The dye or another probe component can be attached to the modified sugar moiety.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof. The dye or another probe component can be attached to the modified phosphate backbone.

"Nucleic acid" also includes a component of a conjugate with one or more modified phosphate bridges (e.g., $P(O)O_3$) by conjugating a linker-dye conjugate of the invention to the nucleic acid, e.g., replacing or derivatizing an oxygen of the bridge) with a compound of the invention or a species that includes a compound of the invention attached to an adaptor. For example, "nucleic acid" also refers to species in which, rather than the $P(O)(O^-)O_2$ moiety of a naturally occurring nucleic acid, includes the moiety ROP(O)(O—)O, in which R is a dye-linker conjugate of the invention, an adaptor, a linker-adaptor cassette or a fluorescent dye-linker-adaptor cassette. An exemplary linker is an amino acid or peptide linker of the invention. In various embodiments, one oxygen of this structure is bound to the phosphorus atom of a $P(O)(O^-)O_2$, such that the nucleic acid includes two or more phosphate moieties bound to each other.

Further exemplary nucleic acids of the invention include a nucleotide having a polyphosphate moiety, e.g., pyrophosphate or a higher homologue, such as the 3-mer, 4-mer, 5-mer, 6-mer, 7-mer, 8-mer and the like. Exemplary nucleic acids include such a polyphosphate moiety bonded to the 5'-oxygen of a nucleoside. In addition to the attached polyphosphate moiety can include a modified phosphate bridge, such as those exemplified herein. In an exemplary embodiment, the modified phosphate bridge is modified with an adaptor, a linker dye conjugate, a linker-adaptor cassette or a fluorescent dye-linker-adaptor cassette. In an exemplary embodiment, the linker is an amino acid or peptide linker such as those set forth herein. Examples of some nucleic acids finding use in the present invention are set forth in Published U.S. Patent Application Nos. 2003/0124576 and 2007/0072196 as well as U.S. Pat. Nos. 7,223,541 and 7,052,839, the full disclosures of which are incorporated herein by reference for all purposes.

Furthermore, "nucleic acid" includes those species in which one or more internucleotide bridge does not include phosphorus: the bridge being optionally modified with a compound of the invention or a linker-dye construct of the invention. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a linker-dye construct of the invention. The discussion above is not limited to moieties that include a carbon atom as the point of attachment; the locus can also be another appropriate linking atom, such as nitrogen or another atom.

Phosphodiester linked nucleic acids of the invention can be synthesized by standard methods known in the art, e.g. by use of an automated DNA synthesizer using commercially available amidite chemistries (Ozaki et al., *Nucleic Acids Research*, 20: 5205-5214 (1992); Agrawal et al., *Nucleic Acids Research*, 18: 5419-5423 (1990); Beaucage et al., *Tetrahedron*, 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

As used herein, "quenching group" refers to any fluorescence-modifying group of the invention that can attenuate, at least partly, the energy (e.g., light) emitted by a fluorescent dye. This attenuation is referred to herein as "quenching". Hence, irradiation of the fluorescent dye in the presence of the quenching group leads to an emission signal from the fluorescent dye that is less intense than expected, or even completely absent. Quenching typically occurs through energy transfer between the fluorescent dye and the quenching group.

"Carrier molecule," as used herein refers to any molecule to which a compound of the invention, or a conjugate incorporating a compound of the invention, is attached. Representative carrier molecules include a nucleic acid, protein (e.g., enzyme, antibody), glycoprotein, peptide, saccharide (e.g., mono-, oligo-, and poly-saccharides), hormone, receptor, antigen, substrate, metabolite, transition state analog, cofactor, inhibitor, drug, dye, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism. An exemplary carrier molecule of use in the present invention is a polyphosphate nucleic acid. Exemplary conjugates between a fluorescent dye and a polyphosphate nucleic acid are conjugated by covalent binding of the dye to the linker and hence to the nucleic acid, or covalent binding of the dye to a linker and the linker to the adaptor—the adaptor is conjugated to the nucleic acid. Alternatively, the dye is bound to a linker, which is bound to an adaptor, which is bound to the nucleic acid. In an exemplary embodiment, the adaptor is bound to the polyphosphate moiety through a phosphodiester bond. In an exemplary embodiment, the adaptor (or linker) is attached to the dye through a bond formed with an activated derivative of a carboxyl moiety on the dye. In various embodiments, the bond is an amide bond.

"Activated derivatives of carboxyl moieties," and equivalent species, refers to moiety on a precursor component of a conjugate of the invention (e.g., dye, adaptor, linker, polyvalent moiety) having an oxygen-containing, or other, leaving group, e.g., an active ester, acyl halide, acyl imidazolide, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and, optionally, those derivatives of alkyl defined in more detail below, such as "heteroalkyl."

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —$CH_2$—$CH_2$—O—$CH_3$, $CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multi-valent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', SO$_3$R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The substituents set forth in the paragraph above are referred to herein as "alkyl group substituents."

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", OC(O)NR'R", —NR"C(O)R', —NR'—C(O)NR'R'", —NR"C(O)$_2$R', —NR—C(NR'R")=NR"", —S(O)R', —S(O)$_2$R', SO$_3$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)$_2$—, or —S(O)$_2$NR'—. The substituents R, R', R" and R'" are preferably independently selected from hydrogen or substituted or unsubstituted (C$_1$-C$_6$)alkyl.

The substituents set forth in the two paragraphs above are referred to herein as "aryl group substituents."

"Analyte", "target", "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, antibodies, antibody fragments and other biomolecules, e.g., antigens, polypeptides, glycoproteins, polysaccharides, complex glycolipids, nucleic acids, effector molecules, receptor molecules, enzymes, inhibitors and the like and drugs, pesticides, herbicides, agents of war and other bioactive agents.

More illustratively, such substances include, but are not limited to, tumor markers such as α-fetoprotein, carcinoembryonic antigen (CEA), CA 125, CA 19-9 and the like; various proteins, glycoproteins and complex glycolipids such as β$_2$-microglobulin (β$_2$ m), ferritin and the like; various hormones such as estradiol (E$_2$), estriol (E$_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the analyte and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH).sub.m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The term PEG or poly(ethylene glycol) is intended to be inclusive and not exclusive. The term PEG includes poly (ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG with degradable linkages therein.

The PEG backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as $R(-PEG-OH)_m$ in which R represents the core, moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

An "Adaptor" is a moiety that is at least bivalent and which is bound to a linker bound to a dye or it is bound directly to the dye. The adaptor also forms a bond with a second dye, polyvalent scaffold or to a nucleic acid. When the adaptor is bound to another dye, either directly or through a polyvalent scaffold, the resulting conjugate is optionally a FRET pair. When the adaptor is bound to a nucleic acid, it is preferably bound to the phosphorus atom of a phosphate, phosphate ester or polyphosphate moiety. In exemplary embodiments, the adaptor is bound through an amide moiety to the dye. The amide moiety is formed between an amine on the adaptor and a carboxyl group on the dye.

"Readlength" is the number of bases the DNA polymerase enzyme at the bottom of the ZMW goes through during sequencing. A longer readlength is desirable. Readlength depends, inter alia, on how fast the enzyme can incorporate fluorescent nucleotides of different colors (monitored this by observing pulse widths and interpulse distances). Readlength also depends on how long the enzyme can incorporate analog without being photodamaged (damaged via undesired interactions with fluorescent nucleotides excited by light).

"Accuracy" is how precise a nucleotide with a base of a particular type can be identified as the polymerase enzyme goes through incorporation of fluorescent nucleotides. The base is identified by a pulse of a selected wavelength upon incorporation of the nucleotide incorporating that base. Robust applications include precise base calling. Accuracy can be diminished by one or more of extra pulses, missing pulses and miscalled pulses.

"Extra pulses"—when a pulse is called and there is no nucleotide incorporation event. Extra pulses may be caused by branching (when enzyme samples the fluorescent analog but does not incorporate), sticks (non-specific interactions of fluorescent nucleotides with enzyme outside of incorporating site and surface of ZMW), photophysical blinking (photophysically unstable behavior of fluorescent nucleotides during incorporation resulting in splitting of fluorescent signal).

"Missing pulses"—when a pulse is not called when there is in fact a nucletided incorporation event. Missing pulses may be caused by insufficient brightness of fluorescent nucleotides, low purity of fluorescent nucleotides, or polymerase going too fast to detect all pulses.

"Miscalled pulses"—when pulse of different kind is called instead of correct one. Miscalls may be caused by insufficient spectral separation between fluorescent nucleotides of different colors, photophysical instability of our fluorescent nucleotides, low intensity or high background of fluorescent nucleotide signal.

Introduction

The present invention provides a class of reactive fluorescent compounds based upon the cyanine-dye nucleus. Also provided is a wide variety of conjugates of the cyanine dyes with, polyphosphate nucleotides, nucleic acids and other carrier molecules, including biological, non-biological and biologically active species. Selected cyanine labels described herein include a functionalized linker arm that is readily converted into an array of reactive derivatives without requiring a modification of the cyanine nucleus. Accordingly, the compounds of the invention provide an, as yet, undisclosed advantage, allowing facile access to an array of conjugates between the linker arm-derivatized cyanine nucleus and carrier molecules.

Residing in the field of fluorescent labels, the present invention provides benefits of particular note. Fluorescent labels have the advantage of requiring few precautions in handling, and being amenable to high-throughput visualization techniques (optical analysis including digitization of the image for analysis in an integrated system comprising a computer). Exemplary labels exhibit one or more of the following characteristics: high sensitivity, high stability, low background, low environmental sensitivity, high specificity in labeling, and a broader range of excitation/emission spectra. Many fluorescent labels based upon the cyanine-nucleus are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate cyanine-based fluorophore for a particular application and, if not readily available commercially, will be able to synthesize the necessary fluorophore de novo or synthetically modify commercially available cyanine compounds to arrive at the desired fluorescent label.

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

The Embodiments

Exemplary cyanine dyes in the compounds of the invention have the formula:

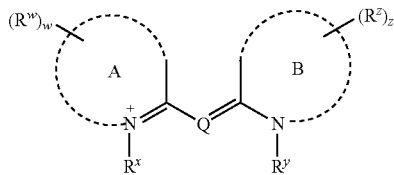

in which A and B are independently selected from substituted or unsubstituted aryl and substituted or unsubstituted heteroaryl such that the compound is a fluorescent dye. When A and/or B is a bicyclic polycyclic moiety, two or more of the rings are optionally fused. Exemplary polycyclic moieties include indole and benzoindole. Q is a substituted or unsubstituted methine moiety (e.g., —(CH=C(R))$_c$—CH=), in which c is an integer selected from 1, 2, 3, 4, or 5 and each R is independently H or an "alkyl group substituent" as defined herein). Each $R^w$, $R^x$, $R^y$ and $R^z$ is independently selected from those substituents set forth in the Definitions section herein as "alkyl group substituents" and "aryl group substituents" without limitation and in any combination. In various embodiments, one or more of $R^w$, $R^x$, $R^y$ and $R^z$ includes a poly(ethylene glycol)moiety. The indices w and z are independently selected from the integers from 0, 1, 2, 3, 4, 5, 6 or greater. In an exemplary embodiment, at least one of $R^w$, $R^x$, $R^y$ and $R^z$ is —(CH$_2$)$_h$G in which G is a ionizable group such as a member selected from SO$_3$H and CO$_2$H, and the index h is the integer 0, 1, 2, 3, 4, 5, 6, 7, 8, 9, 10, 11, 12, 13, 14, 15, 16, 17, 18, 19, 20 or greater. In exemplary embodiments, at least 1, 2, 3, 4, 5, or 6 of $R^x$, $R^y$, $R^w$ and $R^z$ are independently selected alkylsulfonic acid or heteroalkylsulfonic acid and at least one of these moieties is alkylcarboxylic acid, heteroalkylcaboxylic acid, alkylsulfonic acid, and/or heteroalkylsulfonic acid.

In various embodiments, at least one of $R^w$, $R^x$, $R^y$ and $R^z$ is functionalized with an additional dye moiety bonded to the cyanine dye core shown above. In an exemplary embodiment, the additional dye moiety is bonded to the dye core through a linker, a polyvalent scaffold, or a linker-polyvalent scaffold conjugate.

In various embodiments, the invention provides a compound having a formula selected from:

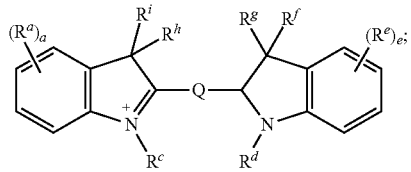

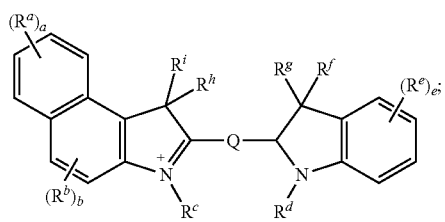

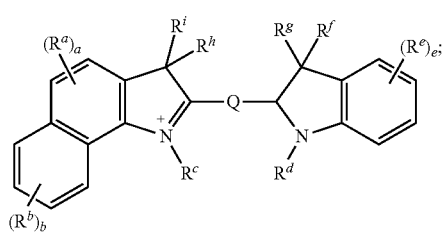

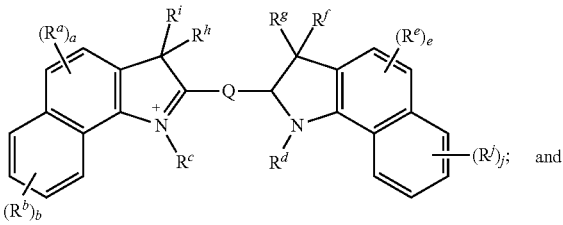

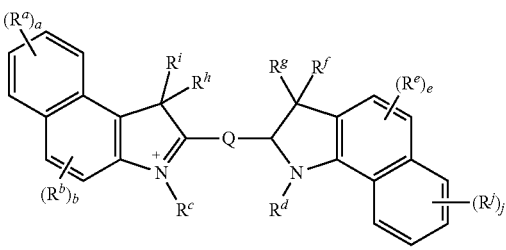

wherein Q is a methine moiety having a formula selected from:

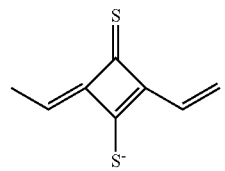

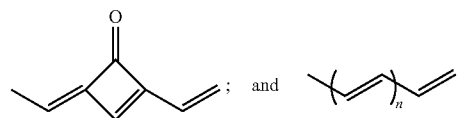

in which one or more of the positions 1, 2, and 3 of the methine moiety is optionally substituted with Ar (e.g., $R^m$). The index n is selected from the integers 1, 2, 3, 4, 5 and greater. The symbol Ar represents substituted or unsubstituted aryl or substituted or unsubstituted heteroaryl. Exemplary heteroaryl moieties are nitrogen containing heteroaryl moieties. An exemplary Ar moiety is a phenyl or pyridyl moiety substituted with one or more carboxylic acid, ester or amide. The indices a and b are integers independently selected from 0, 1, 2, 3, and 4.

In an exemplary embodiment, one or more of $R^a$, $R^e$, $R^j$, $R^f$, $R^g$, $R^h$, and $R^i$ includes a poly(ethylene glycol)moiety.

In an exemplary embodiment, the methine moiety has the formula:

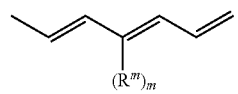

in which the index n is as discussed above. The index m is 0 or 1. $R^m$ is selected from substituted or unsubstituted aryl and substituted or unsubstitute heteroaryl In various embodiments, $R^m$ is selected from:

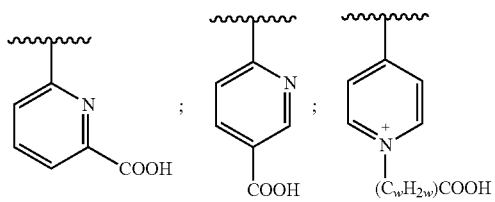

in which w is an integer selected from 1, 2, 3, 4, 5, 6, 7, 8, 9, 10 or greater.

The symbols $R^a$, $R^b$, $R^c$, $R^d$, $R^e$, $R^f$, $R^g$, $R^h$ and $R^i$ are independently selected from H, halogen, $SO_3H$, $CO_2H$, alkylsulfonic acid, alkylcarboxylic acid, sulfonamidoalkylsulfonic acid, amidoalkylsulfonic acid, amidoalkylcarboxylic acid, amidoalkylsulfonic acid, acyloxyalkylsulfonic acid, acyloxyalkylsulfonic acid, substituted or unsubstituted aryl, and substituted or unsubstituted heteroaryl (e.g., pyridyl), a moiety comprising poly(ethylene glycol), and a substituted or unsubstituted aryl ring. The indices a, b, e and j are independently selected from 1, 2, 3, and 4. When one of these indices is greater than 1, each corresponding R group is independently selected, e.g., each $R^a$ group in $(R^a)_2$ is independently selected.

An exemplary substituted or unsubstituted aryl or heteroaryl ring is one substituted by at least one $SO_3H$ or $CO_2H$ moiety, or other moiety referred to herein as an "aryl group substituent." When the compound of the invention includes a polycyclic fused ring (e.g., benzoindole or fused heterocyclylindole), an exemplary ring structure is formed by joining two or more of $R^a$, two or more of $R^e$, and/or two or more of $R^j$, together with the carbon atoms to which they are attached, to form the ring. In various embodiments, the ring structure is selected from substituted or unsubstituted aryl or substituted or unsubstituted heteroaryl. The invention contemplates the full range of permutations of substituents at the different ring positions as set forth above.

In various embodiments, the symbols $R^c$, $R^d$, $R^f$, $R^g$, $R^h$, and $R^i$ represent groups independently selected from unsubstituted alkyl, alkylsulfonic acid, and

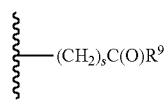

wherein s is selected from the integers 1, 2, 3, 4, 5, 6, 7, 8, 9, 10, 11, 12 or greater. $R^9$ is a member selected from OH, and

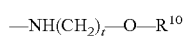

wherein t is selected from the integers from 1, 2, 3, 4, 5, 6, 7, 8, 9, 10, 11 or 12 or greater.

The symbol $R^{10}$ represents H, a moiety comprising poly(ethylene glycol), and

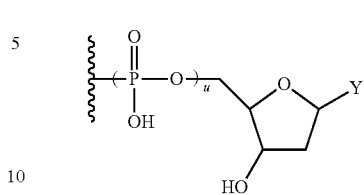

wherein u is selected from the integers from 1, 2, 3, 4, 5, 6, 7, 8, 9, 10 or greater; and Y is a nucleobase.

Exemplary compounds according to the invention include an $R^m$ moiety having a which is a member selected from:

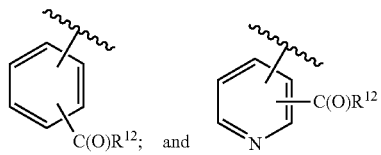

wherein $R^{12}$ is a member selected from OH, and $-NH(CH_2)_{t'}-O-R^{10'}$ wherein t' is selected from the integers 1, 2, 3, 4, 5, 6, 7, 8, 9, 10, 11, 12 or greater. The symbol $R^{10'}$ is a member selected from H, a moiety comprising poly(ethylene glycol), and

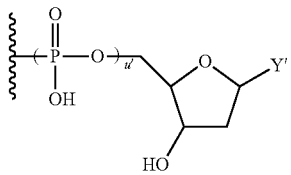

wherein u' is selected from the integers 1, 2, 3, 4, 5, 6, 7, 8 or greater; and Y is a nucleobase.

In various embodiments of the invention, $R^m$ has the formula:

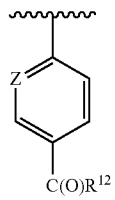

wherein Z is N or C, and $R^{12}$ is as discussed above.

In various embodiments of the invention, the compounds have a formula in which 1, 2, 3, or 4 of $R^a$, $R^e$, $R^j$, $R^c$, $R^d$, $R^f$, $R^g$, $R^h$ and $R^i$ is:

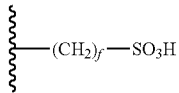

wherein f is an integer selected from 0, 1, 2, 3, 4, 5, 6, 7, 8, 9, 10, 11, 12, 13, 14, 15, 16 or greater. In exemplary embodiments, both $R^c$ and $R^d$ are an alkyl sulfonic acid as shown above.

In various embodiments, the invention provides compounds in which a member selected from $R^a$, $R^e$, $R^j$, $R^c$, $R^d$, $R^f$, $R^g$, $R^h$ and $R^i$ is:

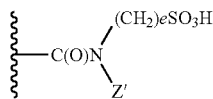

wherein Z' is H or $(CH_2)_fSO_3H$, and e and f are independently selected from the integers 1, 2, 3, 4, 5, 6, 7, 8, 9, 10, 11, 12, 13, 14, 15, 16, 17, 18 or greater. In exemplary embodiments, two or more of $R^a$ and $R^b$, $R^e$ and $R^j$ are each a moiety of this formula.

In various embodiments, the compound of the invention is selected from:

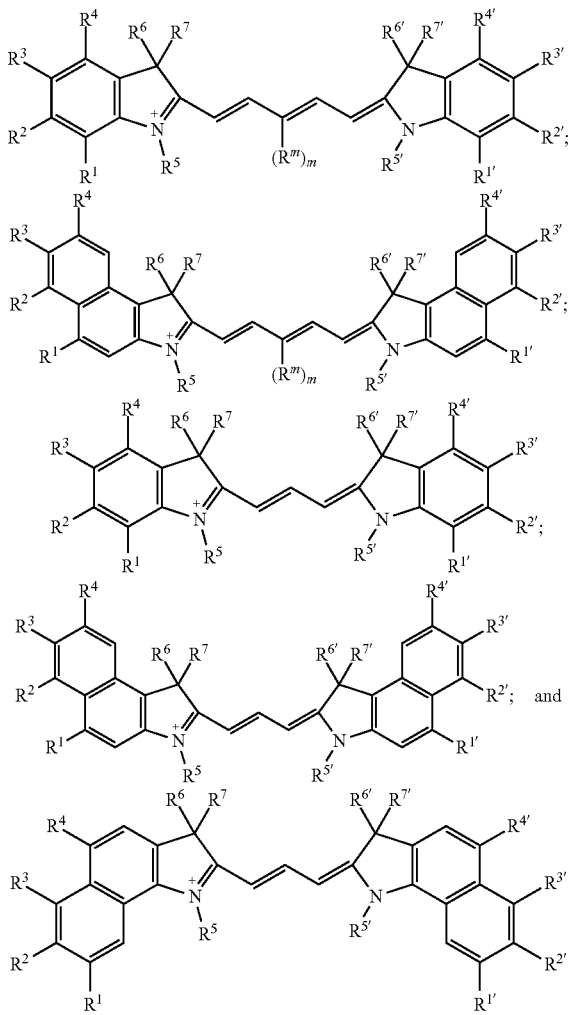

As will be appreciated by those of skill in the art, the preceding discussion regarding the substituents, $R^a$, $R^b$, $R^c$, $R^d$, $R^e$, $R^f$, $R^g$, $R^h$, $R^i$, $R^j$ is fully applicable with respect to the formulae above. For example $R^6$, $R^{6'}$, $R^7$ and $R^{7'}$ correspond to $R^f$, $R^g$, $R^h$ and $R^i$, respectively. Similarly, $R^5$ and $R^{5'}$ correspond to $R^c$ and $R^d$. Depending on the ring to which they are joined, $R^1$-$R^4$ and $R^{1'}$-$R^{4'}$ correspond to $R^a$, $R^e$ and $R^j$.

In various embodiments, $R^1$, $R^{1'}$, $R^2$, $R^{2'}$, $R^3$, $R^{3'}$, $R^4$ and $R^{4'}$ are independently selected from H, $SO_3H$, alkyl sulfonic acid, alkylcarboxylic acid, sulfonamidoalkylsulfonic acid, amidoalkylsulfonic acid, amidoalkylcarboxylic acid, amidoalkylsulfonic acid, acyloxyalkylsulfonic acid, acyloxyalkylsulfonic acid, and substituted or unsubstituted heteroaryl (e.g., pyridyl). Those substituents that include an alkyl subunit, in exemplary embodiments, include 1, 2, 3, 4, 5, 6, 7, 8, 9, 10, 11, 12 or more carbon atoms in the alkyl chain of the alkyl subunit.

In various embodiments, at least two, at least three, or four of $R^1$, $R^{1'}$, $R^2$, $R^{2'}$, $R^3$, $R^{3'}$, $R^4$ and $R^{4'}$ are alkylsulfonic acid. In exemplary embodiments, neither $R^5$ nor $R^{5'}$ is unsubstituted alkyl (e.g., not methyl). In various embodiments, one of $R^5$ and $R^{5'}$ is alkylcarboxylic acid and the other is alkylsulfonic acid. In various embodiments, at least one of $R^1$, $R^{1'}$, $R^2$, $R^{2'}$, $R^3$, $R^{3'}$, $R^4$ and $R^{4'}$ is $SO_3H$. In various embodiments, none of $R^6$, $R^{6'}$, $R^7$ and $R^{7'}$ is unsubstituted alkyl (e.g., none is $C_1$-$C_4$ unsubstituted alkyl, e.g., none is methyl).

In various embodiments, the invention provides compounds in which a member selected from $R^1$, $R^{1'}$, $R^2$, $R^{2'}$, $R^3$, $R^{3'}$, $R^4$ and $R^{4'}$ is:

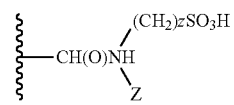

wherein the index z is selected from the integers 1, 2, 3, 4, 5, 6, 7, 8, 9, 10, 11, 12, 13, 14, 15, 16, 17, 18 or greater, and Z is a member selected from H, $C_1$-$C_4$ alkyl (e.g., methyl), and —$(CH_2)_yX$, in which X is $CO_2H$ or $SO_3H$ and the index y is selected from the integers 1, 2, 3, 4, 5, 6, 7, 8, 9, 10, 11, 12, 13, 14, 15, 16, 17, 18 or greater. In exemplary embodiments, two or more of R', $R^{1'}$, $R^2$, $R^{2'}$, $R^3$, $R^{3'}$, $R^4$ and $R^{4'}$ is a moiety of this formula.

In various embodiments, at least two of $R^6$, $R^{6'}$, $R^7$ and $R^{7'}$ are alkylsulfonic acid. In exemplary embodiments, at least one of $R^6$ and $R^{6'}$ is a group other than unsubstituted alkyl (e.g., not methyl). In various embodiments, none of $R^6$, $R^{6'}$, $R^7$ and $R^{7'}$ is unsubstituted alkyl (e.g., not methyl).

In various embodiments of the invention, the compounds have a formula in which 1, 2, 3, or 4 of $R^6$, $R^{6'}$, $R^7$ and $R^{7'}$ is:

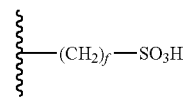

wherein each f is an integer independently selected from 0, 1, 2, 3, 4, 5, 6, 7, 8, 9, 10, 11, 12, 13, 14, 15, 16 or greater.

In exemplary embodiments, both $R^5$ and $R^{5'}$ are alkylsulfonic acid. In exemplary embodiments, one of $R^5$ and $R^{5'}$ is alkylsulfonic acid and the other is alkylcarboxylic acid. In various embodiments, the alkyl moiety is $C_1$, $C_2$, $C_3$, $C_4$, $C_5$, $C_6$, $C_7$, $C_8$, $C_9$, $C_{10}$ or longer.

In various embodiments, $R^m$ is as set forth above an the index m is 0 or 1. In exemplary embodiments, in which $R^m$ (i.e., m=0) is not present, the compound of the invention is substituted with a poly(ethylene glycol)moiety.

In the formulae above, each $R^1$, $R^2$, $R^3$, $R^4$, $R^5$, $R^6$, $R^{1'}$, $R^{2'}$, $R^{3'}$, $R^{4'}$, $R^{5'}$, independently selected from: H, $OCH_3$, $SO_3H$, COOH, TABLE A
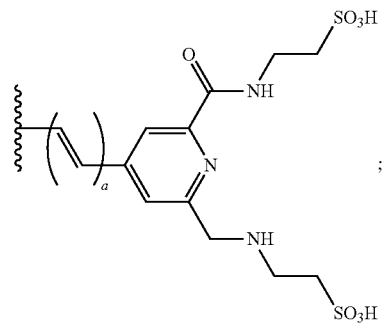
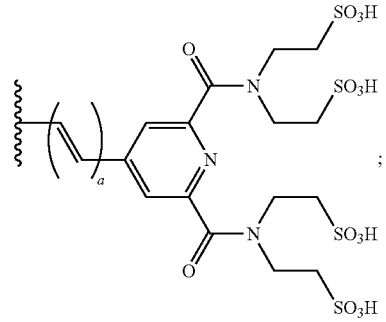
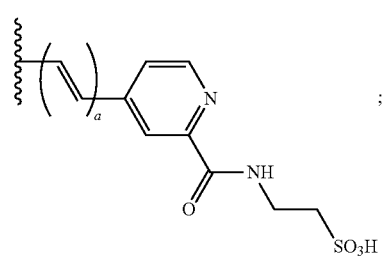
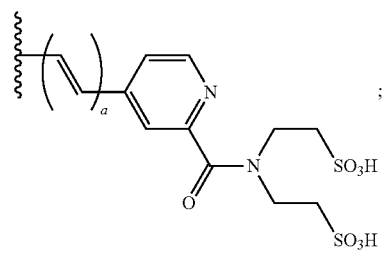
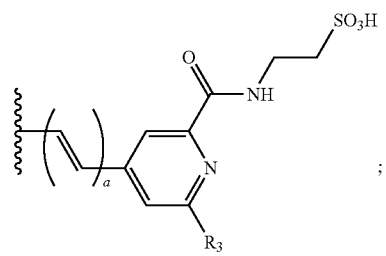
TABLE A-continued
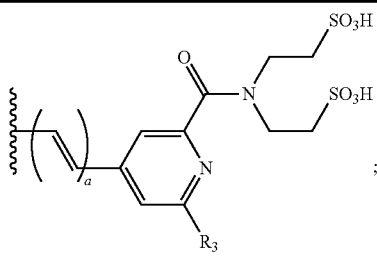
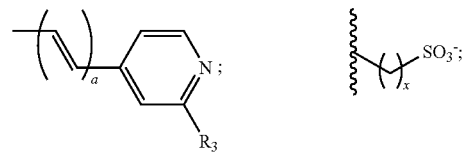
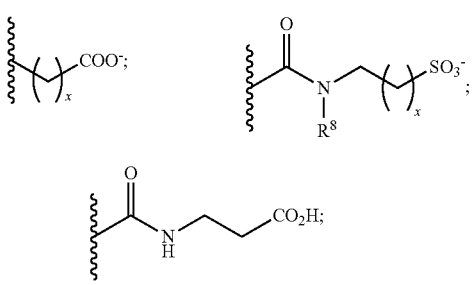
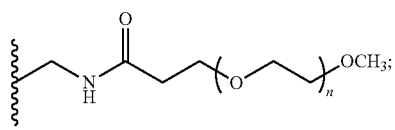
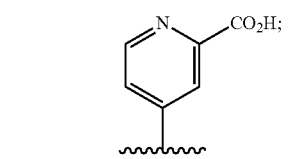
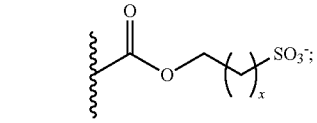
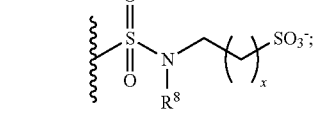
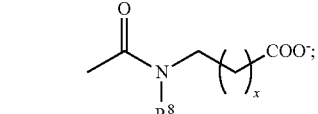
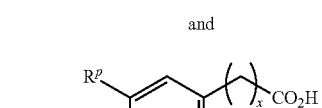
and
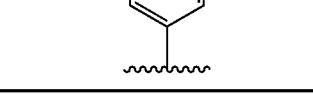

in which the index a is 0 or 1; the index x represents the integer 0, 1, 2, 3, 4, 5, 6, 7, 8, 9, 10 or greater. When a structure includes more than one x, the value of each x is independently selected. The index m is an integer which provides a polyethylene glycol moiety of molecular weight at least about 100, at least about 300, at least about 500, at least about 1000, or at least about 5000 daltons. $R^p$ is H, substituted or unsubstituted alkyl or substituted or unsubstituted heteroalkyl. $R^8$ is a member selected from H, substituted or unsubstituted alkyl and substituted or unsubstituted heteroalkyl. The position of substitution on the pyridyl ring can vary and the point of attachment to the cyanine nucleus can be ortho, meta or para to the endocyclic nitrogen atom.

In an exemplary embodiment, at least one, preferably two or more of $R^a$, $R^b$, $R^e$ or $R^j$ is:

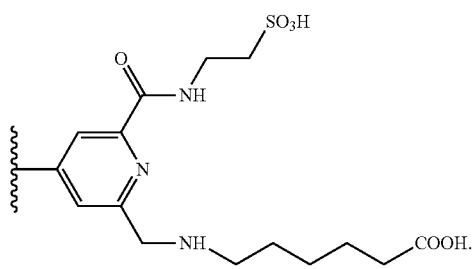 [SMILES: *c1cc(CNCCCCCC(=O)O)nc(C(=O)NCCS(=O)(=O)O)c1]

As will be appreciated by those of skill in the art the alkyl alkyl moieties attached to COOH and $SO_3H$ can be either shorter or longer than shown (e.g., independently 1, 2, 3, 4, 5, 6, 7, 8 9, 10, 11 or 12), or can be replaced with a water-soluble polymer moiety, e.g., poly(ethylene glycol). This moiety can be used as a locus for attachment of another dye or a cassette including another dye, such as a linker-dye cassette. In an exemplary embodiment, the carboxylic acid is converted to an amide component of the multidye construct:

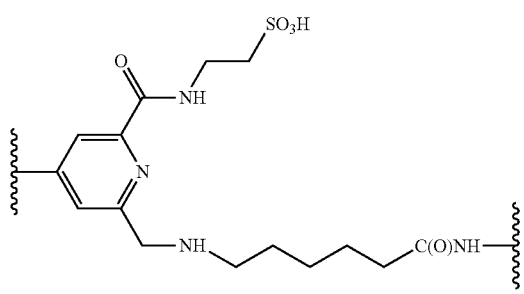

In an exemplary embodiment, the amide is a component of a polyvalent scaffold to which the other dye is or dyes are attached. For example:

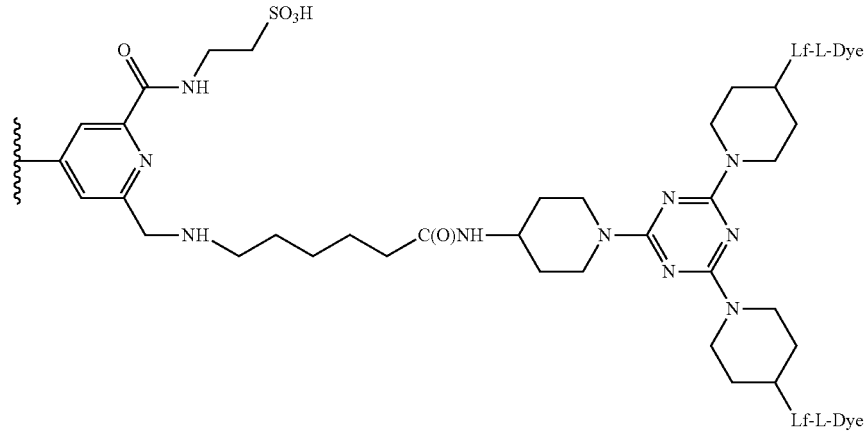

in which $L^f$ is a linkage fragment, for example, S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. An exemplary "Dye" moiety is a cyanine dye, e.g., those disclosed or referenced herein. Similarly, a dye to which the pyridyl substituent attached is a cyanine dye disclosed or referenced herein.

In various embodiments, at least two, at least three or all four of $R^6$, $R^{6'}$, $R^7$ and $R^{7'}$ are alkylsulfonic acid. In exemplary embodiments, at least one of $R^5$ and $R^{5'}$ is other than unsubstituted alkyl (e.g., not methyl). In various embodiments, none of $R^5$, $R^{5'}$, $R^6$, $R^{6'}$, $R^7$, or $R^{7'}$ is unsubstituted alkyl (e.g., not methyl).

In various embodiments of the invention, the compounds have a formula in which 1, 2, 3, 4, 5 or all 6 of $R^5$, $R^{5'}$, $R^6$, $R^{6'}$, $R^7$, or $R^{7'}$ is:

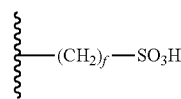

wherein f is an integer selected from 0, 1, 2, 3, 4, 5, 6, 7, 8, 9, 10, 11, 12, 13, 14, 15, 16 or greater.

In exemplary embodiments, both $R^5$ and $R^{5'}$ are alkylsulfonic acid. In exemplary embodiments, one of $R^5$ and $R^{5'}$ is alkylsulfonic acid and the other is alkylcarboxylic acid. In an exemplary embodiment, one or both of $R^5$ and $R^{5'}$ is substituted or unsubstituted aryl or substituted or unsubstituted heteroaryl. An exemplary substituted aryl is a phenyl moiety substituted with a carboxylic acid.

These and additional cyanine dyes of use in practicing the instant invention are set forth in commonly owned U.S. Provisional Patent Application Nos. 61/377,038, titled "Assymetric Cyanine Dyes", 61/377,031, titled "Phospholinked Dye Analogs with an Amino Acid Linker," 61/377,022, titled, "Scaffold-Based Dyes" and 61/377,004, titled, "Molecular Adaptors for Dye Conjugates". The disclosure of each of these applications is incorporated herein by reference in its entirety for all purposes.

Water-Soluble Polymer Conjugates

The hydrophilicity of a selected dyes is enhanced by conjugation with polar moieties such as amine-, ester-, hydroxyl- and polyhydroxyl-containing molecules. Representative examples include, but are not limited to, polylysine, polyethyleneimine, and polyethers, e.g., poly(ethyleneglycol), m-poly(ethylene glycol), poly(propyleneglycol), m-poly(ethylene glycol), and other O-alkyl poly(alkylene glycol) moieties. Preferred water-soluble polymers are essentially non-fluorescent, or emit such a minimal amount of fluorescence that they are inappropriate for use as a fluorescent marker in an assay.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTALS AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), haemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly (amino acids); nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached.

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) or monomethoxy-poly(ethylene glycol) (m-PEG) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie*, 57:5-29 (2002).

The poly(ethylene glycol) useful in forming the conjugate of the invention is either linear or branched. PEG of any molecular weight, e.g., 1 kDa, 2 kDa, 5 kDa, 10 kDa, 15 kDa, 20 kDa, 30 kDa and 40 kDa is of use in the present invention.

The interaction between the water-soluble polymer modified dye and a protein (e.g., DNA polymerase) can also be modulated with water-soluble polymers such as polyethylene glycol (PEG, m-PEG) and polypropylene glycol (PPG). For example, chemical modification of dyes with PEG (PEGylation, m-PEG-ylation) increases their molecular size and decreases their ability to interact with and "stick" to a protein.

In an exemplary embodiment, poly(ethylene glycol) molecules of use in the invention include, but are not limited to, those species set forth below.

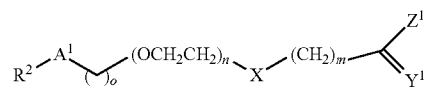

in which $R^2$ is H, substituted or unsubstituted alkyl, substituted or unsubstituted aryl, substituted or unsubstituted heteroaryl, substituted or unsubstituted heterocycloalkyl, substituted or unsubstituted heteroalkyl. The index n represents an integer from 1 to 2500. The indeces m, o, and q independently represent integers from 0 to 20. The symbol $Z^1$ represents OH, $NH_2$, halogen, S—$R^3$, the alcohol portion of activated esters, —$(CH_2)_pC(Y^2)V$, —$(CH_2)_pU(CH_2)_sC(Y^2)_v$, and leaving groups, e.g., imidazole, p-nitrophenyl, HOBT, tetrazole, halide. The symbols X, $Y^1$, and $A^1$ independently represent the moieties O, S, N—$R^4$. The symbol V represents OH, $NH_2$, halogen, S—$R^5$, the alcohol component of activated esters, the amine component of activated amides, sugar-nucleotides, and proteins. The indeces p, and s are independently selected from the integers from 0 to 20. The symbols $R^3$, $R^4$ and $R^5$ independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

In other exemplary embodiments, the poly(ethylene glycol) molecule is selected from the following:

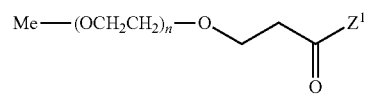

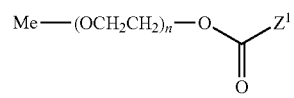

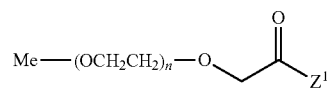

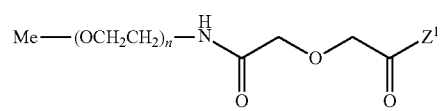

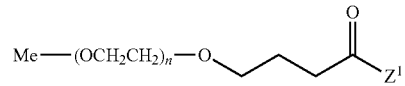

-continued

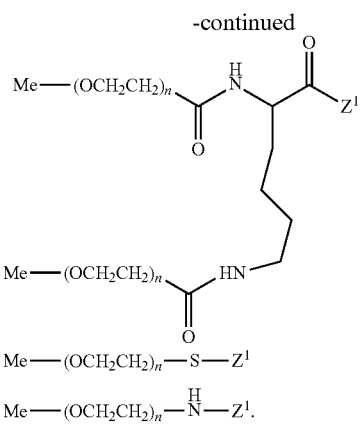

As discussed herein, the PEG of use in the conjugates of the invention can be linear or branched. An exemplary precursor of use to form the branched conjugates according to this embodiment of the invention has the formula:

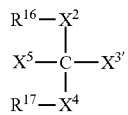

$X^{3'}$ is a moiety that includes reactive functional group, e.g., infra. C is carbon. $X^5$ is preferably a non-reactive group (e.g., H, unsubstituted alkyl, unsubstituted heteroalkyl), and can be a polymeric arm. $R^{16}$ and $R^{17}$ are independently selected polymeric arms, e.g., nonpeptidic, nonreactive polymeric arms (e.g., PEG)). $X^2$ and $X^4$ are linkage fragments that are preferably essentially non-reactive under physiological conditions, which may be the same or different. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join polymeric arms $R^{16}$ and $R^{17}$ to C. When $X^{3'}$ is reacted with a reactive functional group of complementary reactivity on a linker, dye or linker-dye cassette, $X^{3'}$ is converted to a component of linkage fragment $X^3$.

Exemplary linkage fragments for $X^2$, $X^3$ and $X^4$ are independently selected and include S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

In an exemplary embodiment, at least one of $R^a$, $R^b$, $R^e$, $R^f$, $R^g$, $R^h$ and $R^i$ comprises a poly(ethylene glycol)moiety.

In exemplary embodiments, the invention provides compounds that are functionalized with a poly(ethylene glycol) moiety. Exemplary compounds according to this embodiment include a poly(ethylene glycol)moiety having the formula:

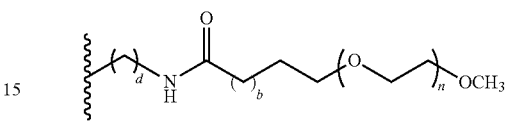

wherein b and d are integers independently selected from 0, 1, 2, 3, 4, 5, 6, 7, 8, 9, 10, 11, 12, 13, 14, 15, 16, 17, and 18; n is an integer from 2 to 10,000. Exemplary values for n include those corresponding to a PEG moiety of molecular weight about 100, about 500, about 1,000, about 3,000 about 5,000, about 10,000 or greater. In an exemplary embodiment, n is about 45. In another exemplary embodiment, n is about 114.

In various embodiments, the poly(ethylene glycol) is a branched poly(ethylene glycol), e.g.:

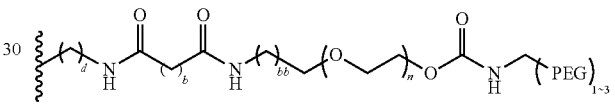

wherein b, bb and d are integers independently selected from 0, 1, 2, 3, 4, 5, 6, 7, 8, 9, 10, 11, 12, 13, 14, 15, 16, 17, and 18; n is an integer from 2 to 10,000. Exemplary values for n include those corresponding to a PEG moiety of molecular weight about 100, about 500, about 1,000, about 3,000 about 5,000, about 10,000 or greater. In an exemplary embodiment, n is about 45. In another exemplary embodiment, n is about 114.

In various embodiments, the poly(ethylene glycol)moiety is located at one or more of $R^a$, $R^b$, $R^e$ and $R^j$. In various embodiments, the poly(ethylene glycol) is located at one or more of $R^f$, $R^g$, $R^h$ and W. In various embodiments, two of $R^f$, $R^g$, $R^h$ and $R^i$ are the poly(ethylene glycol)moiety. In various embodiments two of $R^a$, $R^b$, $R^c$ and $R^j$ are the poly(ethylene glycol)moiety.

In an exemplary embodiment, the compound includes the substructure:

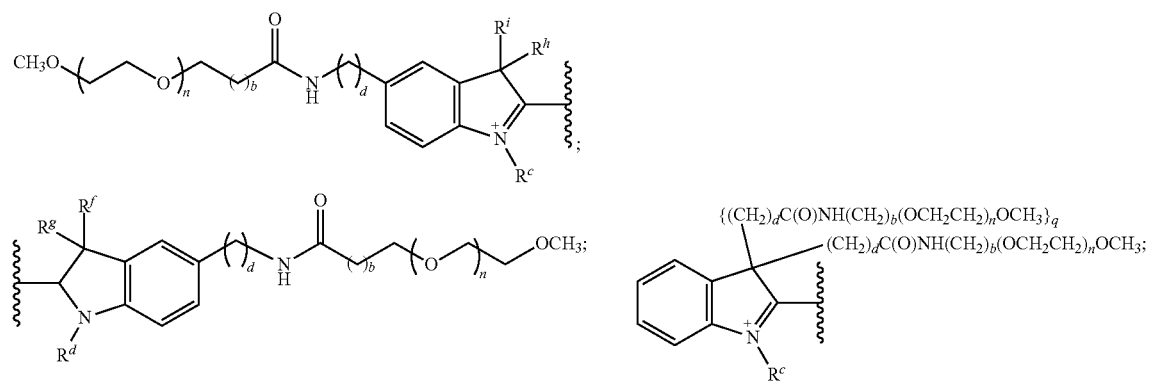

-continued

CH₃O(CH₂CH₂O)ₙ(CH₂)ᵦC(O)NH(CH₂)ₐ {(CH₂)ₐC(O)NH(CH₂)ᵦ(OCH₂CH₂)ₙOCH₃}ᵩ

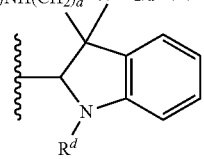

10 or any combination thereof. In the structures above, each q is independently selected from 0 and 1. The other indices are as discussed herein.

Synthesis

An exemplary synthetic route to sulfonated cyanine dyes of the invention is set forth in Scheme 1. Starting keto-ethyl ester 1 is converted to sulfonate 2, which is decarboxylated to sulfonic acid 3. The sulfonic acid is annulated with hydrazine 5 to form the sulfonic acid substituted indolenine 6. At this stage, the indolenine nitrogen can be alkylated with, for example, an activated alkyl carboxylic acid or an activated sulfonic acid to form compound 8 and 9, respectively. The methine group is placed on the indolenine ring by the action of (E)-N-((E)-3-(phenylamino)allylidene)aniline, 10, to form 11. Compound 11 is condensed with compound 8 in acetic anhydride/pyridine to provide cyanine 12.

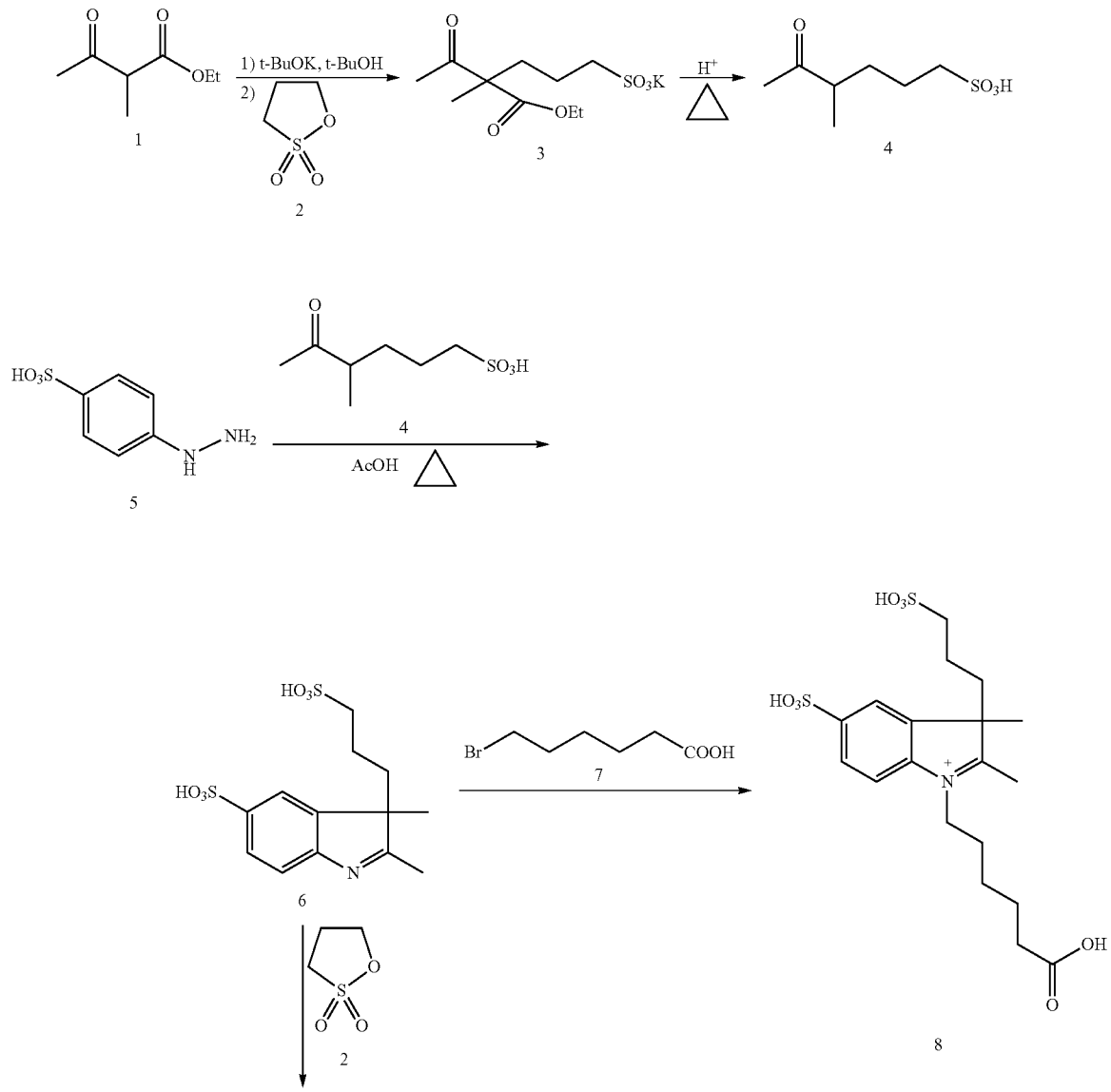

Scheme 1. Synthesis of Pentasulfonated Cyanine Dyes

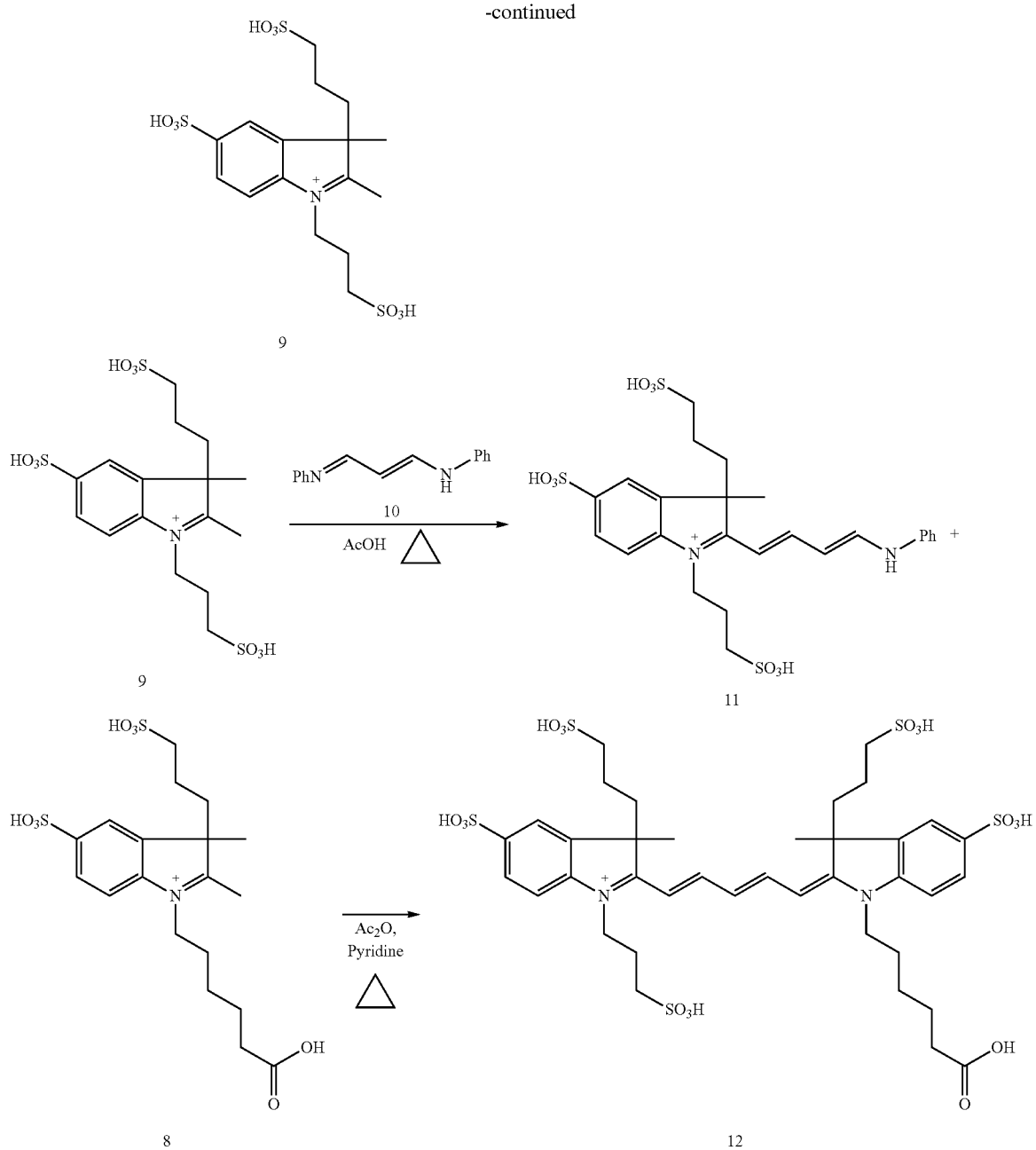

The compounds of the invention can be prepared as a single isomer or a mixture of isomers, including, for example cis-isomers, trans-isomers, diastereomers and stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single isomer. Techniques for inverting or leaving unchanged a particular stereocenter, and those for resolving mixtures of stereoisomers are well known in the art and it is well within the ability of one of skill in the art to choose an appropriate resolution or synthetic method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

Reactive Functional Groups

The compounds of the invention are assembled from covalent bonding reactions between precursors bearing a reactive functional group, which is a locus for formation of a covalent bond between the precursors. The precursors of compounds of the invention bear a reactive functional group, which can be located at any position on the compound. The finished dye conjugates can include a further reactive functional group at any point on the molecule.

Exemplary species include a reactive functional group attached directly to a cyanine nucleus (e.g., aryl ring or methine bridge) or to a linker attached to a component (e.g., aryl ring or methine bridge) of the dye moiety. Other molecules include a reactive functional group attached to a polyvalent moiety. An exemplary reactive functional group is attached to an alkyl or heteroalkyl moiety on the dye. When the reactive group is attached a substituted or unsubstituted alkyl or substituted or unsubstituted heteroalkyl linker moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with reactive dye-based compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New. York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and derivatives thereof including, but not limited to activated esters, e.g., N-hydroxysuccinimide esters, N-hydroxyphthalimide, N-hydroxybenzotriazole esters, acid halides, acyl imidazoles, thioesters, p-nitrophenyl esters, alkyl, alkenyl, alkynyl and aromatic esters, activating groups used in peptide synthesis and acid halides;
(b) hydroxyl groups, which can be converted to esters, sulfonates, phosphoramidates, ethers, aldehydes, etc.
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, allowing derivatization via formation of carbonyl derivatives, e.g., imines, hydrazones, semicarbazones or oximes, or via such mechanisms as Grignard addition or alkyllithium addition;
(f) sulfonyl halide groups for reaction with amines, for example, to form sulfonamides;
(g) thiol groups, which can be converted to disulfides or reacted with acyl halides, for example;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds; and
(k) phosphoramidites and other standard functional groups useful in nucleic acid synthesis.

The reactive functional groups can be chosen such that they do not participate in, or interfere with, the reactions necessary to assemble or utilize the reactive dye analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In addition to those embodiments in which a compound of the invention is attached directly to a carrier molecule, the fluorophores can also be attached by indirect means. In various embodiments, a ligand molecule (e.g., biotin) is covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, and peroxidases.

Polyphosphate Analogues

In an exemplary embodiment, the present invention is generally directed to compositions that comprise compounds analogous to nucleotides, and which, in various aspects are readily processible by nucleic acid processing enzymes, such as polymerases. In addition to the unexpectedly advantageous features imparted to the compounds by incorporation of dyes of novel structure, the compounds of the invention generally benefit from one or more advantages of greater stability to undesired enzymatic or other cleavage or non-specific degradation, as well as incorporation efficiencies that are better than or at least comparable to triphosphate, tetraphosphate or pentaphosphate analogs. Exemplary polyphosphates and their uses are set forth in commonly owned U.S. Pat. No. 7,405,281.

In various embodiments, the invention provides polyphosphate analogs of the cyanine dyes of the invention. In various embodiments, the polyphosphate analogs are polyphosphate analogue of a nucleic acid. An exemplary compound according to this motif has the general structure:

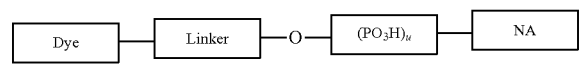

in which NA is the nucleic acid. The index u is an integer selected from 1, 2, 3, 4, 5, 6, 7, 8, 9 or 10.

In an exemplary embodiment, the polyphosphate analogue of the invention has the general structure:

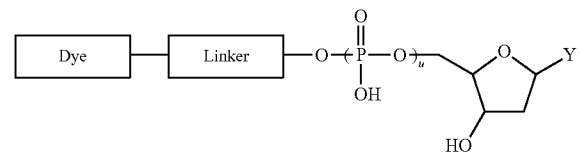

in which Y is a naturally occurring or non-natural nucleobase.

In various embodiments, the polyphosphate analogue of the invention has the general structure:

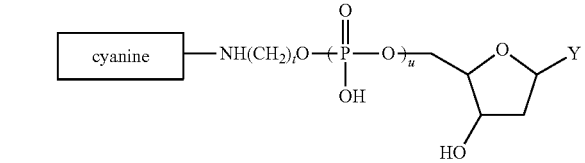

in which t is an integer selected from 1-40, more particularly, 1, 2, 3, 4, 5, 6, 7, 8, 9, 10, 11, 12, 13, 14, 15, 16, 17, 18, 19, 20 or higher.

In an exemplary embodiment, the polyphosphate analogue of the invention has the general structure:

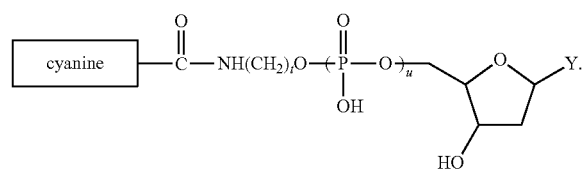

As will be apparent to those of skill in the art, the component labeled "cyanine" refers to the cyanine dyes of the invention set forth herein as well as known cyanines not known to have been conjugated into the structures set forth herein.

In an exemplary embodiment, the cyanine dye component comprises multiple cyanine dyes bound to a common polyvalent scaffold or amplifier. Examples of such scaffold-based cyanine dyes are described in commonly owned U.S. Provisional Patent Application No. 61/377,022, the disclosure of which is incorporated in its entirety herein by reference for all purposes. Examples of dyes that can be incorporated with the dyes of the instant invention into a scaffold-based dye are set forth in U.S. Provisional Patent Application No. 61/377,048, the disclosure of which is incorporated in its entirety herein by reference for all purposes. The scaffold-based dyes of the invention can include FET or FRET pairs. In an exemplary embodiment, the scaffold-based dye composition includes a Cy3 and a Cy5 dye attached to a common polyvalent scaffold or amplifier. In various embodiments, the linker component includes a peptide component. Exemplary peptide components are set forth in commonly owned U.S. Provisional Patent Application No. 61/377,031, the disclosure of which is incorporated in its entirety herein by reference for all purposes. In various embodiments, the linker or cyanine dye component includes an adaptor moiety as set forth in commonly owned U.S. Provisional Patent Application No. 61/377,004, the disclosure of which is incorporated in its entirety herein by reference for all purposes.

Probes

The invention provides probes having a dye of the invention conjugated to a carrier molecule, for example, a target species (e.g., receptor, enzyme, etc.) a ligand for a target species (e.g., nucleic acid, peptide, etc.), a small molecule (e.g., drug, pesticide, etc.), a solid support and the like. The probes can be used for in vitro and in vivo applications. Exemplary probes are those in which the dye is conjugated to the carrier molecule through an adaptor or through a linker-adaptor cassette.

Small Molecule Probes

The dyes of the invention can be used as components of small molecule probes. In an exemplary design, a small molecule probe includes a dye of the invention and a second species that alters the luminescent properties of the dyes, e.g., a quencher of fluorescence. In an exemplary embodiment, an agent, such as an enzyme cleaves the dye of the invention, the quencher or both from the small molecule generating fluorescence in the system under investigation (see, for example, Zlokarnik et al., *Science* 279: 84-88 (1998)).

Nucleic Acid Capture Probes

In one embodiment, an immobilized nucleic acid comprising a dye of the invention is used as a capture probe. The nucleic acid probe can be used in solution phase or it can be attached to a solid support. The immobilized probes can be attached directly to the solid support or through a linker arm between the support and the dye or between the support and a nucleic acid residue. Preferably, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length. Exemplary attachment points include the 3'- or 5'-terminal nucleotide of the probe as well as other accessible sites discussed herein.

Chemical synthesis of nucleic acid probes containing a dye of the invention is optionally automated and is performed by coupling nucleosides through phosphorus-containing covalent linkages. The most commonly used oligonucleotide synthesis method involves reacting a nucleoside with a protected cyanoethyl phosphoramidite monomer in the presence of a weak acid. The coupling step is followed by oxidation of the resulting phosphite linkage. Finally, the cyanoethyl protecting group is removed and the nucleic acid is cleaved from the solid support on which it was synthesized. The labels of the present invention can be incorporated during oligonucleotide synthesis using a mono- or bis-phosphoramidite derivative of the fluorescent compound of the invention. Alternatively, the label can be introduced by combining a compound of the invention that includes a reactive functional group with the nucleic acid under appropriate conditions to couple the compound to the nucleic acid. In yet another embodiment, the fluorescent compound is attached to a solid support through a linker arm, such as a substituted or unsubstituted alkyl, substituted or unsubstituted heteroalkyl or a nucleic acid residue. Synthesis proceeds with the fluorescent moiety already in place on the growing nucleic acid chain.

Enzymatic methods of synthesis involve the use of fluorescent-labeled nucleic acids in conjunction with a nucleic acid template, a primer and an enzyme. Efficient enzymatic incorporation of a fluorescent-labeled nucleic acid is facilitated by selection of reaction partners that do not adversely affect the enzymes ability to couple the partners.

In those embodiments of the invention in which the dye-based fluorescent compound of the invention is attached to a nucleic acid, the carrier molecule is produced by either synthetic (solid phase, liquid phase or a combination) or enzymatically or by a combination of these processes.

Another synthetic strategy for the preparation of oligonucleotides is the H-phosphonate method (B. Froehler and M. Matteucci, *Tetrahedron Lett.*, vol 27, p 469-472, 1986). This method utilizes activated nucleoside H-phosphonate monomers rather than phosphoramidites to create the phosphate internucleotide linkage. In contrast to the phosphoramidite method, the resulting phosphonate linkage does not require oxidation every cycle but instead only a single oxidation step at the end of chain assembly. The H-phosphonate method may also be used to conjugate reporters and dyes to synthetic oligonucleotide chains (N. Sinha and R. Cook, *Nucleic Acids Research*, Vol 16, p. 2659, 1988).

In an exemplary embodiment, the synthesis and purification of the nucleic acid conjugates of compounds of the invention results in a highly pure conjugate, which, if it is a mixture, less than about 30% of the nucleic acid is unlabeled with a dye of the invention, preferably less than about 20% are unlabeled, more preferably less than about 10%, still more preferably less than about 5%, more preferably less than about 1%, more preferably less than about 0.5%, or more preferably less than about 0.1% and even more preferably less than 0.01% of the nucleic acid is unlabeled with a dye of the invention. In certain embodiments, the nucleic acid (e.g., nucleotides and/or nucleotide analogs) is incorporatable by a polymerase enzyme in a template-dependent polymerization reaction.

Dual Labeled Probes

The present invention also provides dual labeled probes that include both a dye of the invention and another label. Exemplary dual labeled probes include nucleic acid probes that include a nucleic acid with a dye of the invention attached thereto, typically, through an adaptor or adaptor-linker cassette. Exemplary probes include both a dye of the invention and a quencher. The probes are of use in a variety of assay formats. For example, when a nucleic acid singly labeled with a dye of the invention is the probe, the interaction between the first and second nucleic acids can be detected by observing the interaction between the dye of the invention and the nucleic acid. Alternatively, the interaction is the quenching by a quencher attached to the second nucleic acid of the fluorescence from a dye of the invention.

The dyes of the invention are useful in conjunction with nucleic-acid probes in a variety of nucleic acid amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the dye of the invention-derivatized nucleic acids can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., *J. Chem. Physics*, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to *nature genetics*, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G., et al., *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al., *Science*, 279:1228-1229 (1998); Matsuo, T., *Biochemica et Biophysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., *Nature*, 350:91-92 (1991).

In view of the well-developed body of literature concerning the conjugation of small molecules to nucleic acids, many other methods of attaching donor/acceptor pairs to nucleic acids will be apparent to those of skill in the art.

More specifically, there are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink™ II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Exemplary fluorophores that can be combined in a probe or scaffold-based dye with a dye of the invention include those set forth in Table 1.

TABLE 1

Exemplary Donors or Acceptors for Compounds of the Invention 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate TABLE 1-continued Exemplary Donors or Acceptors for Compounds of the Invention 4-methylumbelliferone
ortho cresolphthalein
nitrotyrosine
pararosaniline
Phenol Red
B-phycoerythrin
o-phthaldialdehyde
pyrene and derivatives:
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
terbium chelate derivatives
Black Hole Quenchers ™

There is a great deal of practical guidance available in the literature for functionalizing fluorophores and selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

As will be apparent to those of skill in the art the methods set forth above are equally applicable to the coupling to a nucleic acid of groups other than the fluorescent compounds of the invention, e.g., quenchers, intercalating agents, hybridization enhancing moieties, minor groove binders, alkylating agents, cleaving agents, etc.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the quencher moiety is preferably separated from the dye of the invention by at least about 10 nucleotides, and more preferably by at least about 15 nucleotides. The quencher moiety is preferably attached to either the 3'- or 5'-terminal nucleotides of the probe. The dye of the invention moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine: water 1:3, 8 hours, 70° C.). Deprotection under these conditions is facilitated by the use of quick deprotect amidites (e.g., dC-acetyl, dG-dmf).

Peptide Probes

Peptides, proteins and peptide nucleic acids that are labeled with a quencher and a dye of the invention, typically, through an adaptor or linker-adaptor cassette can be used in both in vivo and in vitro enzymatic assays.

Peptide constructs useful in practicing the invention include those with the following features: i) a quencher; ii) a dye of the invention; and iii) a cleavage or assembly recognition site for the enzyme. Moreover, the peptide construct is preferably exists in at least one conformation that allows donor-acceptor energy transfer between the dye of the invention and the quencher when the fluorophore is excited.

In the dual labeled probes of the invention, the donor and acceptor moieties are connected through an intervening linker moiety. The linker moiety, preferably, includes a peptide moiety, but can be or can include another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the dye and the quencher. The separation is measurable as a change in donor-acceptor energy transfer. Alternatively, peptide assembly can be detected by an increase in donor-acceptor energy transfer between a peptide fragment bearing a fluorescent dye and a peptide fragment bearing a donor moiety.

When the cleavage agent of interest is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other protease cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615

(1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

Solid Support Immobilized Dye Analogues

The amino acid or peptide linked dyes of the invention can be immobilized on substantially any polymer, biomolecule, or solid or semi-solid material having any useful configuration. Moreover, any conjugate comprising one or more dye of the invention can be similarly immobilized. In an exemplary embodiment, the dye includes an adaptor or a linker-adaptor casetted and it may be conjugated to the solid support through the adaptor or linker. Alternatively, the dye is attached to another conjugation component through the adaptor or linker-adaptor cassette. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

According to the present invention, the surface of a solid support is functionalized with a dye of the invention or a species to which a dye of the invention is conjugated. For clarity of illustration, the following discussion focuses on attaching a reactive dye of the invention to a solid support. The following discussion is also broadly relevant to attaching to a solid support a species that includes within its structure a dye of the invention.

The dyes of the invention are preferably attached to a solid support by forming a bond between a reactive group on the dye of the invention (e.g., on an amino acid or peptide linker), an adaptor, or a linker-adaptor cassette and a reactive group on the surface of the solid support, thereby derivatizing the solid support with one or more dye of the invention. Alternatively, the reactive group on the dye of the invention is coupled with a reactive group on a linker arm attached to the solid support. The bond between the solid support and the dye of the invention is preferably a covalent bond, although ionic, dative and other such bonds are useful as well. Reactive groups which can be used in practicing the present invention are discussed in detail above and include, for example, amines, hydroxyl groups, carboxylic acids, carboxylic acid derivatives, alkenes, sulfhydryls, siloxanes, etc.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., —COOH membranes; Asahi Chemical Co., Asahi Glass Co., and Tokuyama Soda Co.), and the like.

Microarrays

The present invention also provides microarrays including immobilized dye of the invention and compounds (e.g., peptides, nucleic acids, bioactive agents, etc.) functionalized with a dye of the invention. Moreover, the invention provides methods of interrogating microarrays using probes that are functionalized with a dye of the invention. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics,* 21:48-50 (1999). The discussion that follows focuses on the use of a dye of the invention in conjunction with nucleic acid microarrays. This focus is intended to be illustrative and does not limit the scope of materials with which this aspect of the present invention can be practiced. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990), Pirrung et al. (U.S. Pat. No. 5,143,854, issued 1992), and also by Fodor et al., (*Science,* 251: 767-773 (1991), Southern et al. (*Genomics,* 13: 1008-1017 (1992), Khrapko, et al., *DNA Sequence,* 1: 375-388 (1991), Kleinfield et al., *J. Neurosci.* 8:4098-120 (1998)), Kumar et al., *Langmuir* 10:1498-511 (1994), Xia, Y., *J. Am. Chem. Soc.* 117:3274-75 (1995), Hickman et al., *J. Vac. Sci. Technol.* 12:607-16 (1994), Mrkish et al. *Ann. Rev. Biophys. Biomol. Struct.* 25:55-78 (1996).

Probes of Enzymatic Reactions

In various embodiments, the invention provides a composition which is a substrate for an enzyme, the substrate comprising a component reacted upon by the enzyme, a fluorescent label component and an amino acid or peptide linker component conjugating these two components. The adaptor component is of use to control the interaction of the dye with the enzyme.

In various embodiments, the adaptor serves to control the interaction between a conjugate of the invention and a protein, such as a DNA polymerase. The adaptor can alter the interaction between the conjugate and the protein through electrostatic, hydrophobic, or steric interactions. In an exemplary embodiment in which the conjugate is utilized in a single molecule nucleic acid sequencing technique, the adaptor reduces photobleaching of the dye, photodamage to the enzyme and/or the strength of the interaction between the dye and the enzyme.

The Methods

In addition to the compounds of the invention, there is also provided an array of methods utilizing the compounds. The following discussion is intended to be illustrative of the type and scope of methods with which the compounds of the invention can be practiced and should not be interpreted as being either exhaustive or limiting.

Monitoring Enzymatic Reactions

Peptides, proteins and peptide nucleic acids that, are labeled with a quencher and a dye of the invention can be used in both in vivo and in vitro enzymatic assays. In an exemplary embodiment, the dye is attached to the carrier molecule through an adaptor or a linker-adaptor cassette.

Thus, in another aspect, the present invention provides a method for determining whether a sample contains an enzyme. The method comprises: (a) contacting the sample with a peptide construct that includes a dye of the invention; (b) exciting the fluorophore; and (c) determining a fluorescence property of the sample, wherein the presence of the enzyme in the sample results in a change in the fluorescence property.

Peptide constructs useful in practicing the invention include those with the following features: i) a quencher; ii) a dye of the invention; and iii) a cleavage or assembly recognition site for the enzyme. Moreover, the peptide construct preferably exists in at least one conformation that allows donor-acceptor energy transfer between the dye of the invention and the quencher when the fluorophore is excited.

The assay is useful for determining the presence or amount of enzyme in a sample. For example, by determining the degree of donor-acceptor energy transfer at a first and second time after contact between the enzyme and the tandem construct, and determining the difference in the degree of donor-acceptor energy transfer. The difference in the degree of donor-acceptor energy transfer reflects the amount of enzyme in the sample.

The assay methods also can also be used to determine whether a compound alters the activity of an enzyme, i.e., screening assays. Thus, in a further aspect, the invention provides methods of determining the amount of activity of an enzyme in a sample from an organism. The method includes: (a) contacting a sample comprising the enzyme and the compound with a peptide construct that includes a dye of the invention; (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a preferred embodiment, the amount of enzyme activity in the sample is determined as a function of the degree of donor-acceptor energy transfer in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, nucleotide polymerases (e.g., DNA polymerase), trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

An exemplary assay for proteases are based on donor-acceptor energy transfer from a donor fluorophore to a quencher placed at opposite ends of a short peptide chain containing the potential cleavage site (see, Knight C. G., *Methods in Enzymol.* 248:18-34 (1995)). Proteolysis separates the fluorophore and quencher, resulting in increased intensity in the emission of the donor fluorophore. Existing protease assays use short peptide substrates incorporating unnatural chromophoric amino acids, assembled by solid phase peptide synthesis.

In a further aspect, the invention provides a method of monitoring an enzyme reaction. The method generally comprises providing a reaction mixture comprising die enzyme and at least a first reactant composition, the reactant composition comprising a compound having a reactant component, which is a substrate for the enzyme, a fluorescent label component, and a linker component joining the reactant component to the label component. In various embodiments, the linker component increases the affinity of the conjugate for the enzyme. In various embodiments, the increased affinity reduces the $K_m$ of the reaction, e.g., by 10%, at least 20%, at least 30%, at least 40% or at least 50% relative to the $K_m$ of the reaction with an analogous conjugate without the linker component. The reaction mixture is illuminated to excite the fluorescent label component, and a fluorescent signal from the reaction mixture characteristic of the enzyme reaction is detected.

In an exemplary embodiment, the enzymatic reaction is the reaction of a polymerase with a nucleic acid.

Nucleic Acid Sequencing

In various embodiments, the present invention provides a method for nucleic acid sequencing using one or more compounds of the invention. An exemplary sequencing method is single molecule nucleic acid sequencing. Exemplary dyes used in sequencing include those in which a nucleic acid is bound to the dye through an adaptor or a dye is bound to a nucleic acid through a linker-adaptor cassette.

Significant interest in the sequencing of single DNA molecules dates to 1989 when Keller and colleagues began experimenting with "sequencing by degradation." In their experiments, isolated fully-labeled DNA molecules are degraded by an exonuclease, and individual labeled bases are detected as they are sequentially cleaved from the DNA (Jett, J. H. et al., *J. Biomol. Struct. Dynamics,* 7, 301-309 (1989); Stephan, J. et al., *J. Biotechnol.,* 86, 255-267 (2001); Werner, J. H. et al., *J. Biotechnol.,* 102, 1-14 (2003)). This approach was ultimately compromised by poor DNA solubility caused by the densely-packed dye labels. More recently, alternative single-molecule approaches have been investigated, including "sequencing by synthesis," where bases are detected one at a time as they are sequentially incorporated into DNA by a polymerase (Braslaysky, I. et al., *Proc. Natl. Acad. Sci. USA,* 100, 3960-3964 (2003); Levene, M. J. et al., *Science,* 299, 682-686 (2003); Metzker, M. L., *Genome Res.,* 15, 1767-1776 (2005)); and nanopore sequencing where electrical signals are detected while single DNA molecules pass through protein or solid-state nanopores (Akeson, M. et al., *Biophys. J.,* 77, 3227-3233 (1999); Lagerqvist, J. et al., *Nano Lett.,* 6, 779-782 (2006); Rhee, K. J. et al., Annals of emergency medicine, 13, 916-923 (1984)). So far, only sequencing by synthesis has been successful. In the method of Quake and colleagues (Braslaysky, I. et al., *Proc. Natl. Acad. Sci. USA,* 100, 3960-3964 (2003)), base-labeled nucleotide triphosphates (dNTPs) are incorporated into DNA immobilized on a microscope coverglass. Each type of dNTP is applied separately in a fluidics cycle, and incorporated bases are imaged on the surface after washing away the excess of free nucleotides. While the obtained sequence reads are short, high sequencing rates can potentially be achieved by analyzing billions of different, individual molecules in parallel with applications in re-sequencing and gene expression profiling.

To obtain long single-molecule reads, potentially tens of kilobases, sequencing-by-synthesis approaches using phosphate-labeled nucleotides have been developed (Levene, M. J. et al., *Science,* 299, 682-686 (2003)). These nucleotides are labeled with a fluorophore on the terminal phosphate instead of on the base. Labeled nucleotides are detected while bound to polymerase during the catalytic reaction. The label is released with pyrophosphate as the nucleotide is incorporated into DNA. An advantage is that the DNA remains label-free and fully soluble. Individual polymerase enzymes immobilized on a microscope coverglass are monitored in real time to detect the sequence of incorporated nucleotides. In order to achieve long reads, the polymerase, but not the DNA, can be attached to the coverglass. Polymerase attachment facilitates detection because it keeps the active site at a single position on the coverglass surface. In the alternative format, with the polymerase in solution and the DNA attached, the enzyme active site would be a moving target for detection, diffusing up to several microns from the DNA attachment point as the primer strand is extended from long templates.

U.S. Pat. No. 6,255,083, issued to Williams and incorporated herein by reference, discloses a single molecule sequencing method on a solid support. The solid support is optionally housed in a flow chamber having an inlet and outlet to allow for renewal of reactants that flow past the immobilized polymerases. The flow chamber can be made of plastic or glass and should either be open or transparent in the plane viewed by the microscope or optical reader.

Accordingly, it is within the scope of the present invention to utilize the compounds set forth herein in single molecule DNA sequencing.

In accordance with one embodiment of the methods of invention, the compounds described herein are used in analyzing nucleic acid sequences using a template dependent polymerization reaction to monitor the template dependent incorporation of specific analogs into a synthesized nucleic acid strand, and thus determine the sequence of nucleotides present in the template nucleic acid strand. In particular, a polymerase enzyme is complexed with the template strand in the presence of one or more nucleotides and/or one or more nucleotide analogs of the invention. In preferred aspects, only the labeled analogs of the invention are present representing analogous compounds to each of the four natural nucleotides, A, T, G and C. When a particular base in the template strand is encountered by the polymerase during the polymerization reaction, it complexes with an available analog that is complementary to such nucleotide, and incorporates that analog into the nascent and growing nucleic acid strand, cleaving between the $\alpha$ and $\beta$ phosphorus atoms in the analog, and consequently releasing the labeling group (or a portion thereof). The incorporation event is detected, either by virtue of a longer presence of the analog in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. In addition to their use in sequencing, the analogs of the invention are also equally useful in a variety of other genotyping analyses, e.g., SNP genotyping use single base extension methods, real time monitoring of amplification, e.g., RT-PCR methods, and the like. See, for example, U.S. Pat. Nos. 7,056,661, 7,052,847, 7,033,764, 7,056,676, 6,917,726, 7,013,054, 7,181,122, 7,292,742 and 7,170,050 and 7,302,146, the full disclosures of which are incorporated herein by reference in their entirety for all purposes.

The present invention also provides methods of using the compounds described herein in performing nucleic acid analyses, and particularly nucleic acid sequence analyses. The methods of the invention typically comprise providing a template nucleic acid complexed with a polymerase enzyme in a template dependent polymerization reaction to produce a nascent nucleic acid strand, contacting the polymerase and template nucleic acid with a compound of the invention, and detecting whether or not a synthon derived from the compound (e.g., monophosphate nucleic acid subunit) was incorporated into the nascent strand during the polymerization reaction, and identifying a base in the template strand based upon incorporation of the compound. Preferably, the foregoing process is carried out so as to permit observation of individual nucleotide incorporation reactions, through the use of, for example, an optical confinement, that allows observation of an individual polymerase enzyme, or through the use of a heterogeneous assay system, where label groups released from incorporated analogs are detected.

The invention also provides methods of monitoring nucleic acid synthesis reactions. The methods comprise contacting a polymerase/template/primer complex with a fluorescently labeled nucleotide or nucleotide analog having a nucleotide or nucleotide analog component, a fluorescent label component, and a linker-adaptor component joining the nucleotide or nucleotide analog component to the label component. A characteristic signal from the fluorescent dye is then detected that is indicative of incorporation of the nucleotide or nucleotide analog into a primer extension reaction.

The adaptor linked fluorophores of the invention are of use in single molecule or single molecule real time (SMRT) DNA sequencing assays. Of particular note in this context is the ability provided by the invention to design fluorophores with selected absorbance and emission properties including wavelength and intensity. The compounds of the invention provide for very versatile assay design. For example, according to the present invention a series of fluorophores of use in an assay are readily designed to have selected absorbance and emission wavelengths and emission intensities, allowing multiple fluorophores to be utilized and distinguished in an assay. In exemplary embodiments, use of compounds of the invention in a multifluorophore assay, e.g., single molecule DNA sequencing, enhances assay performance by at least about 10%, at least about 20% or at least about 30% over a similar assay using currently available fluorophores.

Polymerase Chain Reaction

In another aspect, the invention provides a method for detecting amplification by PCR of a target sequence. Methods of monitoring PCR using dual labeled nucleic acid probes are known in the art. See, *Expert Rev. Mol. Diagn.*, 5(2), 209-219 (2005). Exemplary dyes used in PCR probes include those in which a nucleic acid is bound to the dye through an adaptor or a dye is bound to a nucleic acid through a linker-adaptor cassette.

The dyes and their conjugates described herein can be used in substantially any nucleic acid probe format for PCR. For example, the dyes of the invention can be incorporated into probe motifs, such as Taqman™ probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature Biotechnology* 14:303-308 (1996), Jayasena et al., U.S. Pat. No. 5,989,823, issued Nov. 23, 1999)) scorpion probes (Whitcomb et al., *Nature Biotechnology* 17: 804-807, (1999)), sunrise probes (Nazarenko et al., *Nucleic Acids Res.* 25: 2516-2521 (1997)), conformationally assisted probes (Cook, R., copending and commonly assigned U.S. patent application Ser. No. 09/591,185), peptide nucleic acid (PNA)-based light up probes (Kubista et al., WO 97/45539, December 1997), double-strand specific DNA dyes (Higuchi et al, *Bio/Technology* 10: 413-417 (1992), Wittwer et al, *BioTechniques* 22: 130-138 (1997)) and the like. These and other probe motifs with which the present dyes can be used are reviewed in NONISOTOPIC DNA PROBE TECHNIQUES, Academic Press, Inc. 1992.

Nucleic Acid Detection

In another embodiment, the invention provides a method of detecting a target nucleic acid in an assay mixture or other sample. The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art. Exemplary dyes used in sequencing include those in which a nucleic acid is bound to the dye through an adaptor or a dye is bound to a nucleic acid through a linker-adaptor cassette.

An exemplary method uses a dye of the invention or a conjugate thereof to detect a nucleic acid target sequence. The method includes: (a) contacting the target sequence with a detector nucleic acid that includes a dye of the invention and a quencher; (b) hybridizing the detector nucleic acid to the target sequence, thereby altering the conformation of the detector nucleic acid, causing a change in a fluorescence parameter; and (c) detecting the change in the fluorescence parameter, thereby detecting the nucleic acid target sequence.

In various embodiments, the detector nucleic acid includes a single-stranded target binding sequence. The binding sequence has linked thereto: i) a quencher; and ii) a dye of the invention. Moreover, prior to its hybridization to a complementary sequence, the detector nucleic acid is preferably in a conformation that allows donor-acceptor energy transfer between the quencher and the dye of the invention when the fluorophore is excited. Furthermore, in the methods described in this section, a change in fluorescence is detected as an indication of the presence of the target sequence. The change in fluorescence is preferably detected in real time.

Kits

In another aspect, the present invention provides kits containing one or more dye of the invention or a conjugate thereof. In one embodiment, a kit includes a reactive dye of the invention and directions for attaching this derivative to another molecule. In another embodiment, the kit includes a dye-labeled polyphosphate nucleic acid in which an adaptor is present between the dye (or dye linker cassette) and the polyphosphate nucleic acid. The kit further includes one or more component selected from buffers or other compounds or solutions of use in practicing the method, an enzyme (e.g., a DNA polymerase), cofactors necessary for enzyme reactions, and directions for performing the assay.

The materials and methods of the present invention are further illustrated by the examples that follow. These examples are offered to illustrate, but not to limit the claimed invention.

The following examples are provided by way of illustration only and not by way of limitation. Those of skill in the art will readily recognize a variety of non-critical parameters that could be changed or modified to yield essentially similar results.

EXAMPLES

Example 1

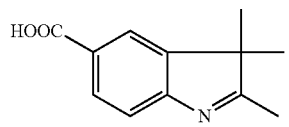

1.1 2,3,3-Trimethyl-5-carboxy-3H-indole

A solution of 4-hydrazinobenzoic acid (10.0 g, 65.7 mmol), isopropylmethylketone (21.1 mL, 197 mmol) in acetic acid (35 mL) was heated under reflux in an oil bath for 20 h. After cooling to ambient temperature the solvent was evaporated off under reduced pressure and to it was added a saturated aqueous solution of NaHCO3 (50 mL) and washed with $CH_2Cl_2$ (3×40 mL). The pH of the aqueous solution was adjusted with 1 M aqueous HCl to ca. 2, and then extracted with $CH_2Cl_2$ (3×50 mL). The combined organic solution was then dried with $Na_2SO_4$, filtered and concentrated to dryness under reduced pressure to yield the desired product (10.7 g, 80%) as a brownish solid.

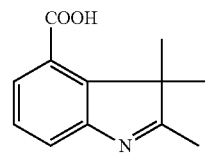

1.2 2,3,3-Trimethyl-4-carboxy-3H-indole

A solution of 3-hydrazinobenzoic acid (30.0 g, 197 mmol), isopropylmethylketone (31.7 mL, 296 mmol) in ethanol (500 mL) and sulfuric acid (5 mL) was heated under reflux in an oil bath for 20 h. After cooling to ambient temperature the solvent was evaporated off under reduced pressure to a small volume of ~200 mL. Collected the solid with a filter funnel, washed with iPrOH (3×30 mL) and ethyl ether (3×30 mL) and dried. Further drying of the solid in an oven at 45° C. under high vacuum for 18 h provided 32.59 g (81.3%) of the product.

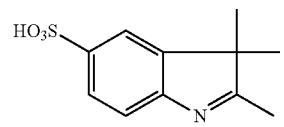 [SMILES: CC1=Nc2ccc(S(=O)(=O)O)cc2C1(C)C]

1.3 2,3,3,-Trimethylindoleninium-5-sulfonate

To an oven dried 500-mL round bottomed flask equipped with a stirring bar, a reflux condenser and a nitrogen balloon was add p-hydrazinobenzenesulfonic acid hemihydrate (50.0 g, 0.253 mol), acetic acid (150 mL), and 3-methyl-2-butanone (84 mL, 0.785 mol). Heated the reaction mixture with stirring in an oil bath at 115° C. for 4 h. Monitored the reaction with TLC (2:1 $CH_2Cl_2$:MeOH; starting material $R_f$=0.42, product $R_f$=0.69) until all starting material was consumed. Removed oil bath and cooled the reaction solution to ambient temperature. Slowly added EtOAc (~200 mL) and the resultant pink solid were collected via filtration with the aid of EtOAc (2×50 mL). After brief drying the solid was dissolved in MeOH (700 mL). Added KOH (15 g) in iPrOH (200 mL) to the above solution and stirred. Collected the resultant yellow solid via filtration. Washed the solid with iPrOH (2×100 mL), EtOAc (3×100 mL) and air dried. Placed the solid in two amber bottles and dried in a desiccator under high vacuum overnight. There was obtained 48.8 g (69.5%) of the desired product as a potassium salt.

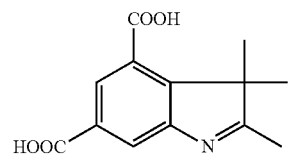

1.4 2,3,3-Trimethyl-4,6-dicarboxy-3H-indole

A solution of 5-hydrazinylbenzene-1,3-dicarboxylic acid (30.0 g, 129 mmol), isopropylmethylketone (22.0 mL, 205 mmol) in acetic acid (300 mL) and was heated under reflux in an oil bath for 18 h. After cooling to ambient temperature the solvent was evaporated off under reduced pressure to a small volume of ~100 mL. To the crude mixture was added iPrOH (200 mL) and the solid was collected with a filter funnel, washed with EtOAc (3×200 mL) and ethyl ether (2×200 mL) and dried. Further drying of the solid in an oven at 50° C. under high vacuum for 18 h provided 30.44 g (95.5%) of the product.

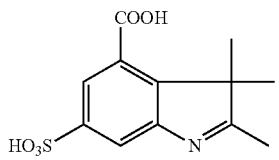

1.5 2,3,3,-Trimethylindoleninium-4-carboxy-6-sulfonate

To a solid of 2,3,3-trimethyl-4-carboxy-3H-indole (5.20 g, 25.6 mmol) was added oleum (30%, 8 mL, 45.3 mmol) at ambient temperature and heated to 100° C. for 18 h. After cooling to ambient temperature the acid was poured into ethyl ether (400 mL). Filtered to collect the solid and washed the solid with CH3CN (3×50 mL). Re-dissolved the solid in D.I. water (20 mL) and neutralized with KOH to basic (~pH 10). The aqueous solvent was evaporated off under reduced pressure to give a solid, which was then extracted with MeOH (3×100 mL). After filtering through a pad of filter paper the organic extracts were combined and concentrated to dryness to give a solid product. Further drying in an oven at 45° C. under high vacuum gave 5.44 g (75.0%) of the off-white solid product.

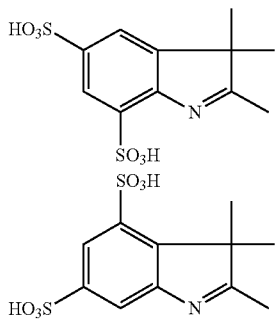

1.6 2,3,3,-Trimethylindoleninium-5,7-disulfonate and 2,3,3,-Trimethylindoleninium-4,6-disulfonate To a solution of 2,3,3-trimethylindoleninium (2.00 mL, 12.5 mmol) was added oleum (30%, 11 mL, 62.3 mmol) and stirred at ambient temperature for 48 h followed by heating to 160° C. for 18 h. After cooling to ambient temperature the acid was poured into ice water (50 mL) and neutralized with KOH to basic. The aqueous solvent was evaporated off under reduced pressure to give a solid, which was then extracted with MeOH (3×100 mL). After filtering through a pad of filter paper the organic extracts were combined and concentrated to dryness. Triturated the solid with iPrOH 950 mL) and the solid was collected through filtration, washed with EtOAc (3×20 mL) and dried. Further drying in an oven at 45° C. under high vacuum gave a mixture of the titled compound (~6:4) as an off-white solid (quantitative yield).

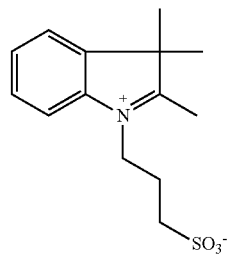

1.7 1-(3-Sulfonatopropyl)-2,3,3-trimethylindoleninium

To an oven dried 50-mL round bottom flask equipped with a stir bar, condenser, and an argon balloon in an oil bath was added 2,3,3-trimethylindolenine (1.60 mL, 10.0 mmol), 1,3-propanesultone (1.32 mL, 15.0 mmol) and 1,2-dichlorobenzene (20 mL). Heated the oil bath to 140° C. for 18 h. Removed the oil bath and cooled the mixture to ambient temperature. Decanted the solvent and triturated the solid with EtOAc (40 mL). Collected the solid using filtration funnel. Re-dissolved the solid in hot MeOH (20 mL) and concentrated to dryness to give the solid product. Further drying in an oven at 45° C. under high vacuum overnight gave 1.96 g (70.0%) of product.

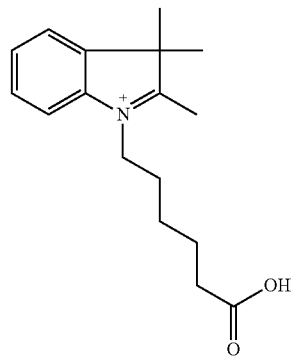

1.8 1-Carboxypentyl-2,3,3-trimethylindoleninium

To an oven dried 250-mL round bottom flask equipped with a stir bar, condenser, and an argon balloon in an oil bath was added 2,3,3-trimethylindolenine (5.00 g, 31.4 mmol), bromohexanoic acid (6.74 g, 34.5 mmol) and 1,2-dichlorobenzene (250 mL). Heated the oil bath to 110° C. for 30 h. Removed the oil bath and cooled the mixture to ambient temperature. Decanted the solvent and triturated the solid with EtOAc (40 mL). Collected the solid using filtration funnel. Re-dissolved the solid in MeOH (30 mL) and added EtOAc (100 mL) and Et2O (400 mL) to precipitate the solid. The resultant solid was collected, washed with 1:1 EtOAc:

Hexanes (3×40 mL), Et₂O (3×30 mL) and air dried. Further drying in an oven at 45° C. under high vacuum gave the off-white solid (4.00 g, 36% yield) product. Filtrate still contain lot of product and was discarded without attempt to isolate more of the product.

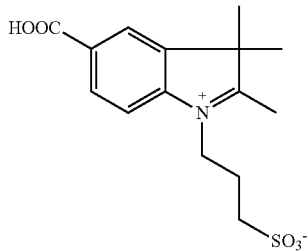

1.9 1-(3-Sulfonatopropyl)-2,3,3-trimethylindole-ninium-5-carboxylate

A solution of 2,3,3-trimethyl-5-carboxy-3H-indole (193 mg, 0.950 mmol) in 1,3-propanesultone (1 mL) was heated to 145° C. in a sealed tube for 20 h. Cooled the tube to ambient temperature and to it was added ethyl acetate (20 mL), stirred and the organic solvent was decanted. Repeated the process two more times with ethyl acetate (2×20 mL) and the oily product was dried under reduced pressure. Added 6 M HCl (10 mL) to the tube and heated to 60° C. for 4 h. After cooling to ambient temperature the solvent was evaporated off under reduced pressure. The crude product was then purified by reverse-phase HPLC (acetonitrile/0.1 M TEAB gradient) to give 300 mg of a solid product (97% yield) after evaporation of solvent.

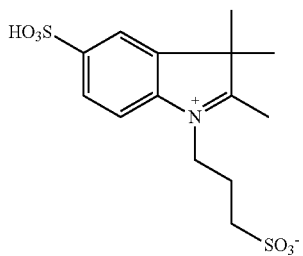

1.10 1-(3-Sulfonatopropyl)-2,3,3-trimethylindole-ninium-5-sulfonate

To an oven dried 50-mL round bottom flask equipped with a stir bar, condenser, and an argon balloon in an oil bath was added 2,3,3-trimethylindoleninium-5-sulfonate (1.50 g, 5.40 mmol), 1,3-propanesultone (0.62 mL, 7.0 mmol) and 1,2-dichlorobenzene (15 mL). Heated the oil bath to 140° C. for 48 h. The progress of the reaction was monitored with analytical HPLC for the disappearance of the starting material, and the formation of the product. Removed oil bath and cooled the mixture to ambient temperature. Decanted the solvent and triturated the solid with EtOAc (40 mL). Collected the solid using filtration funnel. Re-dissolved the solid in hot MeOH (40 mL) and added iPrOH (200 mL) to precipitate the solid. The resultant solid was collected, washed with iPrOH (2×50 mL), EtOAc (2×50 mL), ether (2×50 mL) and air dried. The solid was placed in an amber bottle and dried in an oven under high vacuum overnight. There was obtained a total of 1.28 g (59.2%) of product.

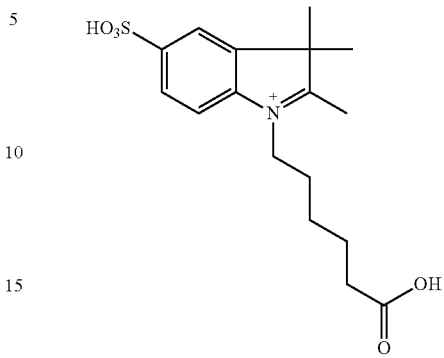

1.11 1-Carboxypentyl-2,3,3-trimethylindoleninium-5-sulfonate

To an oven dried 250-mL round bottom flask equipped with a stir bar, condenser, and an argon balloon in an oil bath was added 2,3,3-trimethylindolenine-5-sulfonate (10 g, 36.05 mmol), bromohexanoic acid (8.78 g, 45.0 mmol) and 1,2-dichlorobenzene (100 mL). Heated the oil bath to 110° C. for 24 h. Monitored the reaction with TLC (2:1 CH₂Cl₂: MeOH) for the disappearance of starting material ($R_f$=0.69) and the formation of product ($R_f$=0.22). Removed oil bath and cooled the mixture to room temperature. Decanted the solvent and triturated the solid with iPrOH (100 mL). Collected the solid using filtration funnel. Re-dissolved the solid in MeOH (300 mL) and added iPrOH (700 mL) to precipitate the solid. The resultant solid was collected, washed with iPrOH (2×50 mL), EtOAc (2×50 mL), ether (2×50 mL) and air dried. The solid was placed in an amber bottle and dried in a desiccator under high vacuum overnight. There was obtained a total of 8.02 g (62%) of product.

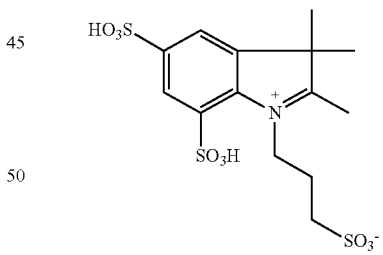

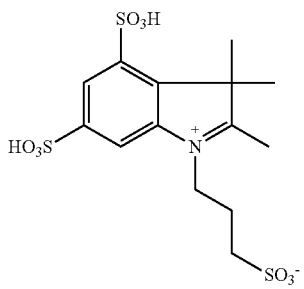

1.12 1-(3-Sulfonatopropyl)-2,3,3-trimethylindoleninium-5,7-disulfonate and 1-(3-Sulfonatopropyl)-2,3,3-trimethylindoleninium-4,6-disulfonate To a 6:4 mixture of 2,3,3,-trimethylindoleninium-5,7-disulfonate and 2,3,3,-trimethylindoleninium-4,6-disulfonate (803.2 mg, 2.515 mmol) was added 1,3-propanesultone (1.99 mL, 22.6 mmol) in a seal vial. Heated the vial in an oil bath at 140° C. for 72 h. After cooling to ambient temperature added ethyl acetate (20 mL) to triturate the solid. Decanted the organic solvent and continue to triturate the solid with EtOAc (3×20 mL). Collected the solid using filtration funnel. Re-dissolved the solid in hot MeOH (40 mL) and added iPrOH (200 mL) to precipitate the solid. The resultant solid was collected, washed with iPrOH (2×50 mL), EtOAc (2×50 mL), ether (2×50 mL) and air dried. The solid was placed in an amber bottle and dried in an oven under high vacuum overnight. There was obtained 660 mg (60%) of product.

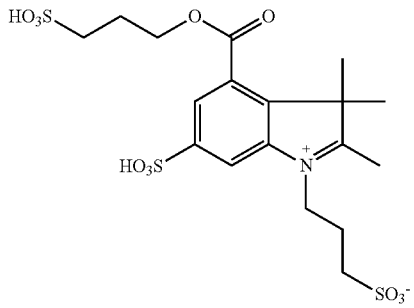

1.13 1-(3-Sulfonatopropyl)-2,3,3-trimethylindoleninium-4-(sulfonatopropylcarboxylate)-6-sulfonate A mixture of 2,3,3-trimethylindoleninium-4-carboxy-6-sulfonate (218 mg, 0.769 mmol) and 1,3-propanesultone (1.5 mL, 17 mmol) in a sealed tube was heated to 140° C. for 60 h. Cooled the mixture to ambient temperature and to it was added ethyl acetate (20 mL), stirred and the organic solvent was decanted. Repeated the process two more times with ethyl acetate (2×20 mL) and the oily product was dried under reduced pressure. Added 1 M HCl (15 mL) to the tube and heated to 80° C. for 4 h. After cooling to ambient temperature the solvent was evaporated off under reduced pressure. The crude product was then purified by reverse-phase HPLC (acetonitrile/0.1 M TEAB gradient) to give 263.2 mg of the solid product (64.8% yield).

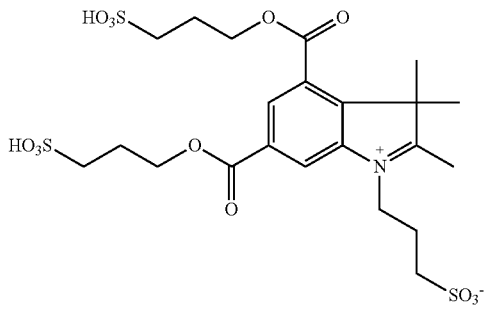

1.14 1-(3-Sulfonatopropyl)-2,3,3-trimethylindoleninium-4,6-di(sulfonatopropylcarboxylate)

A mixture of 2,3,3-trimethyl-4,6-dicarboxy-3H-indole (600 mg, 2.43 mmol), 1,3-propanesultone (5 mL, 57 mmol) and sofolane (3 mL) in a sealed tube was heated to 125° C. for 36 h. Cooled the mixture to ambient temperature and to it was added ethyl acetate (20 mL), stirred and the organic solvent was decanted. Repeated the process two more times with ethyl acetate (2×20 mL) and the oily product was dried under reduced pressure. Added 1 M HCl (10 mL) to the tube and heated to 60° C. for 10 h. After cooling to ambient temperature the solvent was evaporated off under reduced pressure. The crude product was then purified by reverse-phase HPLC (acetonitrile/0.1 M TEAB gradient) to give 283 mg (18%) of the solid product and 605 mg (51% yield) of a monoacid ester, presumably the 4-carboxy derivative.

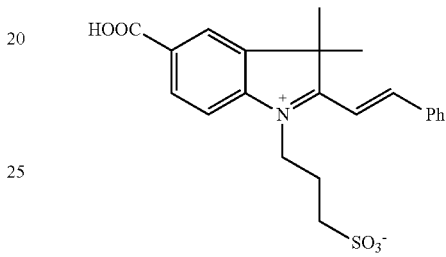

1.15 2-[(1E)-2-Anilinoethenyl]-3,3-dimethyl-1-(3-sulfonatopropyl)-3H-indoleninium-5-carboxylate A mixture of 1-(3-sulfonatopropyl)-2,3,3-trimethylindoleninium-5-carboxylate (108 mg, 0.27 mmol) and N,N'-diphenylformamidine (66 mg, 0.34 mmol) in acetic acid (5 mL) was heated to reflux for 18 h. The progress of the reaction was monitored with analytical HPLC for the disappearance of starting material, and the formation of product. Extended heating may be needed to completely consume the starting material, however, some of the symmetrical dye can also be produced. Acetic acid was removed under reduced pressure and the residual dark solid was washed with ethyl acetate (3×20 mL). The dried solid was used without further purification in the next reaction for carbocyanine dye synthesis.

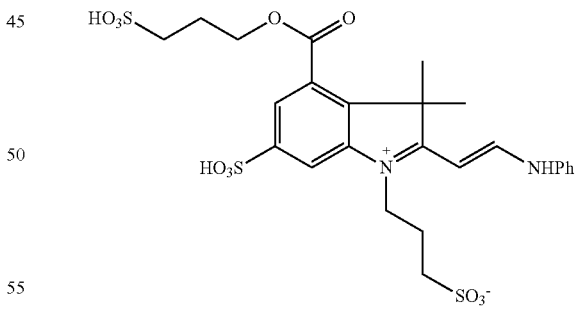

1.16 2-[(1E)-2-Anilinoethenyl]-3,3-dimethyl-1-(3-sulfonatopropyl)-4-(sulfonatopropylcarboxylate)indoleninium-6-sulfonate A mixture of 1-(3-sulfonatopropyl)-2,3,3-trimethylindoleninium-4-(sulfonatopropylcarboxylate)-6-sulfonate (50.0 mg, 0.0948 mmol) and N,N'-diphenylformamidine (121 mg, 0.616 mmol) in acetic acid (3 mL) was heated to reflux for 18 h. The progress of the reaction was monitored with analytical HPLC for the disappearance of starting material, and the formation of product. Extended heating may be needed to completely consume the starting material, however, some of the symmetrical dye can also be produced. Acetic acid was removed under reduced pressure and the residual dark solid was washed with ethyl acetate (3×20 mL), dried and purified by reverse-phase HPLC (acetonitrile/0.1 M TEAB gradient) to give 41 mg of the solid product (70% yield).

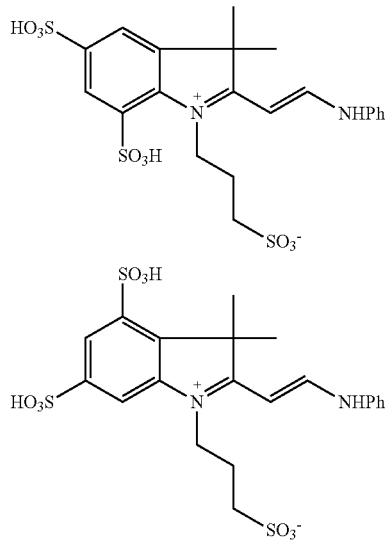

1.17 2-[(1E)-2-Anilinoethenyl]-3,3-dimethyl-1-(3-sulfonatopropyl)-3H-indoleninium-5,7-disulfonate and 2-[(1E)-2-Anilinoethenyl]-3,3-dimethyl-1-(3-sulfonatopropyl)-3H-indoleninium-4,6-disulfonate A mixture of 1-(3-sulfonatopropyl)-2,3,3-trimethylindoleninium-5,7-disulfonate and 1-(3-sulfonatopropyl)-2,3,3-trimethylindoleninium-4,6-disulfonate (~6:4, 161.2 mg, 0.366 mmol) and N,N'-diphenylformamidine (86 mg, 0.44 mmol) in acetic acid (2 mL) and acetic anhydride (2 mL) was heated to reflux for 18 h. The progress of the reaction was monitored with analytical HPLC for the disappearance of the starting material, and the formation of the product. Extended heating may be needed to completely consume the starting material, however, some of the symmetrical dye can also be produced. Solvent was removed under reduced pressure and the residual dark solid was washed with ethyl acetate (3×20 mL). The dried solid was used without further purification in the next reaction for carbocyanine dye synthesis.

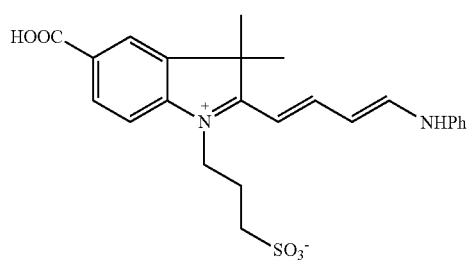

1.18 2-[(1E,3E)-4-Anilinobuta-1,3-dienyl]-3,3-dimethyl-1-(3-sulfonatopropyl)-3H-indoleninium-5-carboxylate A mixture of 1-(3-sulfonatopropyl)-2,3,3-trimethylindoleninium-5-carboxylate (300 mg, 0.922 mmol) and malonaldehyde dianil hydrochloride (310 mg, 1.20 mmol) in acetic acid (10 mL) was heated to reflux for 16 h. The progress of the reaction was monitored with analytical HPLC for the disappearance of the starting material, and the formation of the product. Acetic acid was removed under reduced pressure and the residual dark solid was washed with ethyl acetate (3×20 mL). The dried solid was used without further purification in the next reaction for dicarbocyanine dye synthesis.

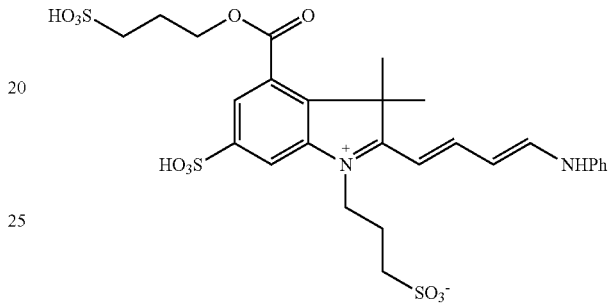

1.19 2-[(1E,3E)-4-Anilinobuta-1,3-dienyl]-3,3-dimethyl-1-(3-sulfonatopropyl)-3H-indoleninium-4-(sulfonatopropylcarboxylate)-6-sulfonate A mixture of 1-(3-sulfonatopropyl)-2,3,3-trimethylindoleninium-4-(sulfonatopropylcarboxylate)-6-sulfonate (50.0 mg, 0.0948 mmol) and malonaldehyde dianil hydrochloride (48.0 mg, 0.185 mmol) in acetic acid (3 mL) was heated to reflux for 18 h. The progress of the reaction was monitored with analytical HPLC for the disappearance of the starting material, and the formation of the product. Acetic acid was removed under reduced pressure and the residual dark solid was washed with ethyl acetate (3×20 mL), dried and purified by reverse-phase HPLC (acetonitrile/0.1 M TEAB gradient) to give 35 mg of the solid product (56.3% yield).

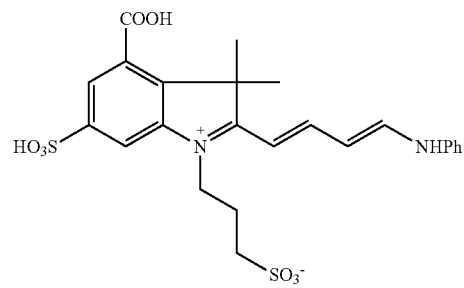

1.20 2-[(1E,3E)-4-Anilinobuta-1,3-dienyl]-3,3-dimethyl-1-(3-sulfonatopropyl)-3H-indoleninium-4-carboxy-6-sulfonate A solution of 1-(3-sulfonatopropyl)-2,3,3-trimethylindoleninium-4-carboxy-6-sulfonate (72.9 mg, 0.180 mmol) and malonaldehyde dianil hydrochloride (56.0 mg, 0.216 mmol)

in acetic anhydride (2 mL) and acetic acid (3 mL) was heated to reflux for 26 h. The progress of the reaction was monitored with analytical HPLC for the disappearance of the starting material, and the formation of the product. Solvent was removed under reduced pressure and the residual dark solid was washed with ethyl acetate (3×20 mL). The dried solid was used without further purification in the next reaction for dicarbocyanine dye synthesis.

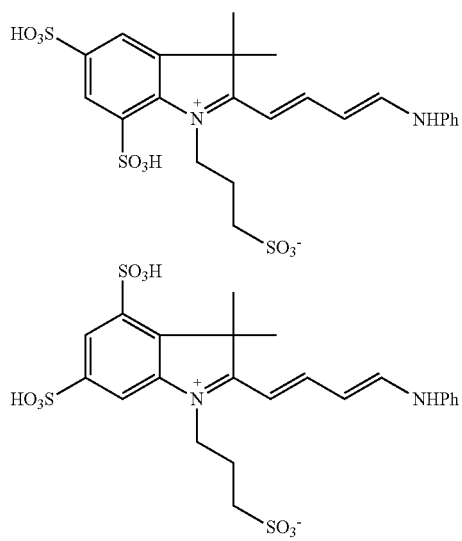

1.21 2-[(1E,3E)-4-Anilinobuta-1,3-dienyl]-3,3-dimethyl-1-(3-sulfonatopropyl)-3H-indoleninium-5,7-disulfonate and 2-[(1E,3E)-4-Anilinobuta-1,3-dienyl]-3,3-dimethyl-1-(3-sulfonatopropyl)-3H-indoleninium-4,6-disulfonate A mixture of 1-(3-sulfonatopropyl)-2,3,3-trimethylindoleninium-5,7-disulfonate and 1-(3-sulfonatopropyl)-2,3,3-trimethylindoleninium-4,6-disulfonate (~6:4, 195 mg, 0.442 mmol) and malonaldehyde dianil hydrochloride (126 mg, 0.487 mmol) in acetic acid (2.4 mL) and acetic anhydride (2.4 mL) was heated to reflux for 4 h. Solvent was removed under reduced pressure and the residual dark solid was washed with ethyl acetate (3×20 mL). The dried solid was used without further purification in the next reaction for dicarbocyanine dye synthesis.

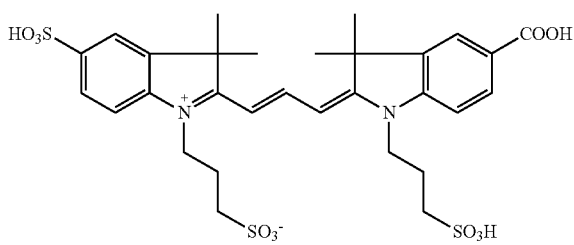

1.22 Preparation of 1.22

To a solution of 2-[(1E)-2-anilinoethenyl]-3,3-dimethyl-1-(3-sulfonatopropyl)-3H-indoleninium-5-carboxylate (37.7 mg, 0.088 mmol) and 1-(3-sulfonatopropyl)-2,3,3-trimethylindoleninium-5-sulfonate (38.7 mg, 0.097 mmol) in N,N-dimethylformamide (5 mL) was added Ac$_2$O (2 mL), pyridine (2 mL) and stirred at ambient temperature for 24 h. Solvent was evaporated off under reduced pressure to give a dark red residue, which was then purified by reverse-phase HPLC (acetonitrile/0.1 M TEAB gradient) to give 41.7 umole of the product (47% yield). λmax (553 nm).

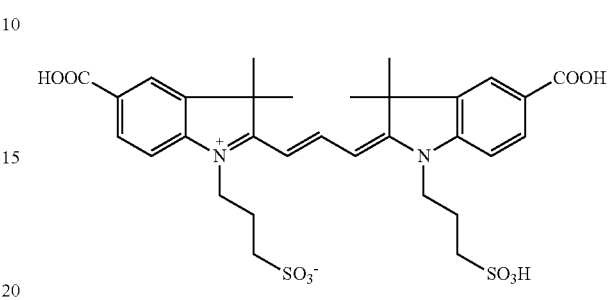

1.23 Preparation of 1.23

A solution of 1-(3-sulfonatopropyl)-2,3,3-trimethylindoleninium-5-carboxylate (473 mg, 1.45 mmol) and triethyl orthoformate (166 uL, 1.6 mmol) in pyridine (5 mL) was heated to reflux for 2 h. Solvent was evaporated off under reduced pressure to give a dark red residue, which was then purified by reverse-phase HPLC (acetonitrile/0.1 M TEAB gradient) to give 0.181 mmol of the product (25% yield). λmax (556 nm).

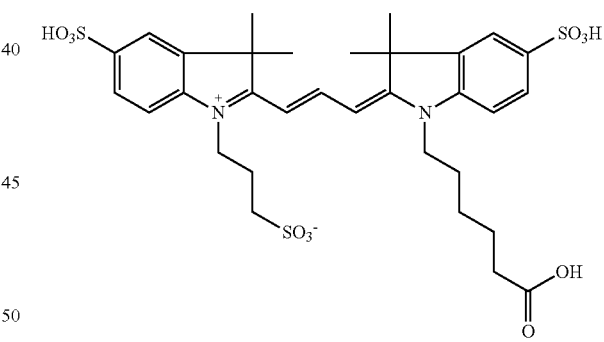

1.24 Preparation of 1.24

A solution of 1-(3-sulfonatopropyl)-2,3,3-trimethylindoleninium-5-sulfonate (46.6 mg, 0.117 mmol), 1-carboxypentyl-2,3,3-trimethylindoleninium-5-sulfonate (41.2 mg, 0.117 mmol) and triethyl orthoformate (20 uL, 0.12 mmol) in pyridine (3 mL) was heated to reflux for 48 h. Solvent was evaporated off under reduced pressure to give a dark red residue, which was then purified by reverse-phase HPLC (acetonitrile/0.1 M TEAB gradient) to give 1.71 umol of the product (3% yield). λmax (551 nm)

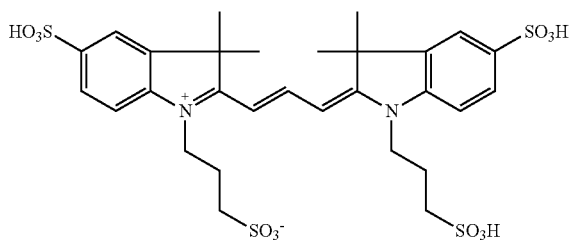

1.25 Preparation of 1.25

A solution of 1-(3-sulfonatopropyl)-2,3,3-trimethylindoleninium-5-sulfonate (97.9 mg, 0.245 mmol) and N,N'-diphenylformamidine (24.0 mg, 0.122 mmol) in acetic anhydride (3 mL) and pyridine (5 mL) was heated to reflux for 18 h. Solvent was evaporated off under reduced pressure to give a dark red residue, which was then purified by reverse-phase HPLC (acetonitrile/0.1 M TEAB gradient) to give the product. λmax (550 nm).

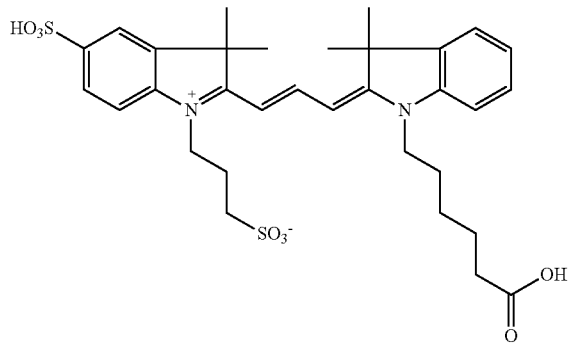

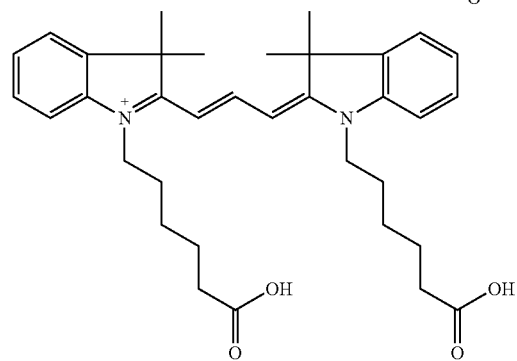

1.26 Preparation of 1.26B and 1.26C

A solution of 1-(3-sulfonatopropyl)-2,3,3-trimethylindoleninium-5-sulfonate (85.5 mg, 0.214 mmol), 1-carboxypentyl-2,3,3-trimethylindolenine (75.8 mg, 0.214 mmol) and triethyl orthoformate (40 uL, 0.24 mmol) in pyridine (3 mL) and MeOH (3 mL) was heated to reflux for 24 h. Solvent was evaporated off under reduced pressure to give a dark red residue, which was then purified by reverse-phase HPLC (acetonitrile/0.1 M TEAB gradient) to give 3 carbocyanine dyes, 1.26A ((λmax, 550 nm), 1.26B (λmax, 549 nm) and diacid symmetrical dye 1.26C (λmax, 549 nm).

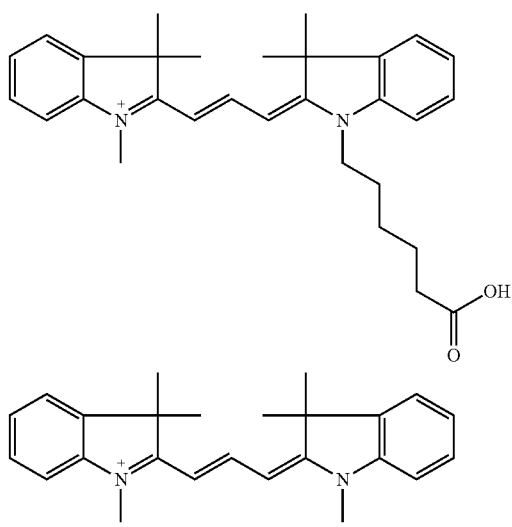

1.27 Preparation of 1.27B and 1.27C

A solution of 1,2,3,3-tetramethylindoleninium (79.0 mg, 0.262 mmol), 1-carboxypentyl-2,3,3-trimethylindoleninium (92.9 mg, 0.262 mmol) and triethyl orthoformate (45 uL, 0.27 mmol) in pyridine (3 mL) and MeOH (3 mL) was heated to reflux for 2 h. Additional triethyl orthoformate (45 uL, 0.27 mmol) was added and continue to reflux for 3 h. Solvent was evaporated off under reduced pressure to give a dark red residue, which was then purified by reverse-phase HPLC (acetonitrile/0.1 M TEAB gradient) to give 3 carbocyanine dyes, 1.27A (λmax, 549 nm), 1.27B (λmax, 545 nm) and dimethyl symmetrical dye 1.27C (λmax, 543 nm).

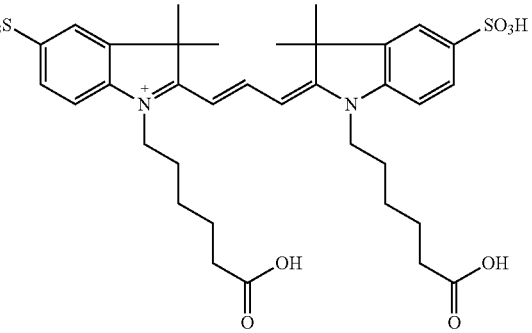

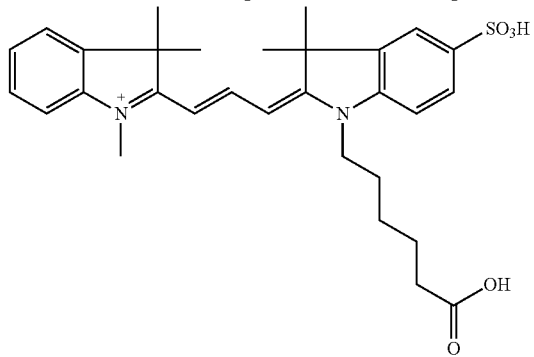

1.28 Preparation of 1.28A and 1.28B

A solution of 1,2,3,3-tetramethylindoleninium (91.3 mg, 0.303 mmol), 1-carboxypentyl-2,3,3-trimethylindoleninium-5-sulfonate (107.1 mg, 0.303 mmol) and triethyl orthoformate (55 uL, 0.33 mmol) in pyridine (3 mL) and MeOH (1 mL) was heated to reflux for 2 h. Additional triethyl orthoformate (55 uL, 0.33 mmol) was added and continue to reflux for 3 h. Solvent was evaporated off under reduced pressure to give a dark red residue, which was then purified by reverse-phase HPLC (acetonitrile/0.1 M TEAB gradient) to give 3 carbocyanine dyes, 1.28A (λmax, 553 nm), 1.28B (λmax, 548 nm) and dimethyl symmetrical dye 1.28C (λmax, 543 nm).

1.29 Preparation of 1.29A and 1.29B

A solution of 2-[(1E)-2-anilinoethenyl]-3,3-dimethyl-1-(3-sulfonatopropyl)-3H-indoleninium-5,7-disulfonate and 2-[(1E)-2-anilinoethenyl]-3,3-dimethyl-1-(3-sulfonatopropyl)-3H-indoleninium-4,6-disulfonate (~6:4, 66 mg, 0.122 mmol), 1-carboxypentyl-2,3,3-trimethylindoleninium-5-sulfonate (43.1 mg, 0.122 mmol) in N,N-dimethylformamide (2 mL) and acetic anhydride (1 mL) and pyridine (1 mL) was stirred a ambient temperature for 24 h. Solvent was evaporated off under reduced pressure to give a dark red residue, which was then purified by reverse-phase HPLC (acetonitrile/0.1 M TEAB gradient) to give 1.8 umol of the two products in ~6:4. λmax (560 nm, 1.29A); λmax (558 nm, 1.29B).

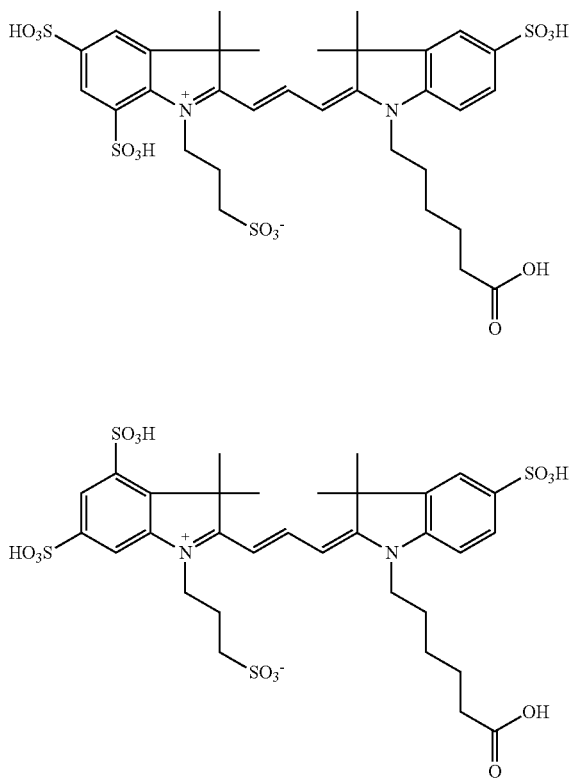

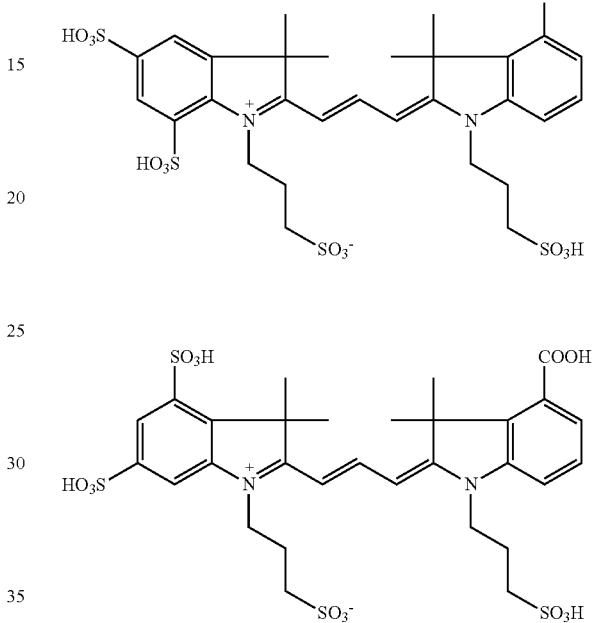

1.30 Preparation of 1.30A and 1.30B

A solution of 2-[(1E)-2-anilinoethenyl]-3,3-dimethyl-1-(3-sulfonatopropyl)-3H-indoleninium-5,7-disulfonate and 2-[(1E)-2-anilinoethenyl]-3,3-dimethyl-1-(3-sulfonatopropyl)-3H-indoleninium-4,6-disulfonate (~6:4, 148 mg, 0.272 mmol), 1-(3-sulfonatopropyl)-2,3,3-trimethylindoleninium-4-carboxylate (70.0 mg, 0.215 mmol) in N,N-dimethylformamide (3 mL) and acetic anhydride (1 mL) and pyridine (1 mL) was stirred at ambient temperature for 24 h. Solvent was evaporated off under reduced pressure to give a dark red residue, which was then purified by reverse-phase HPLC (acetonitrile/0.1 M TEAB gradient) to give 2.1 umol of the two products in ~6:4. λmax (554 nm, 1.30A); λmax (550 nm, 1.30B).

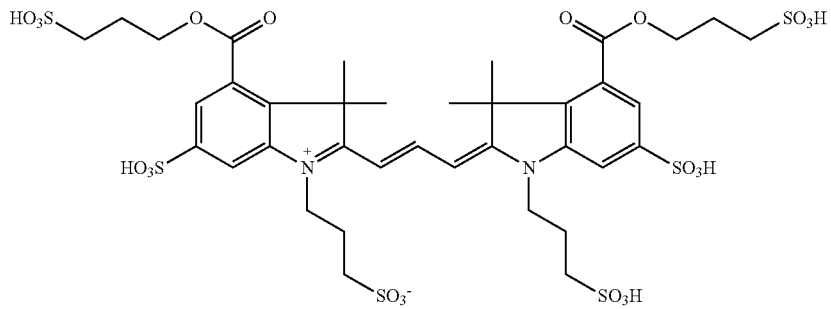

1.31 Preparation of 1.31

A solution of 1-(3-sulfonatopropyl)-2,3,3-trimethylindoleninium-4-(sulfonatopropylcarboxylate)-6-sulfonate (25 mg, 0.062 mmol) and triethyl orthoformate (30 uL, 0.18 mmol) in pyridine (2 mL) was heated to reflux inside a sealed vial for 2.5 h. Solvent was evaporated off under reduced pressure to give a dark red residue, which was then purified by reverse-phase HPLC (acetonitrile/0.1 M TEAB gradient) to give 0.0154 mmol of the product (25% yield). λmax (540 nm).

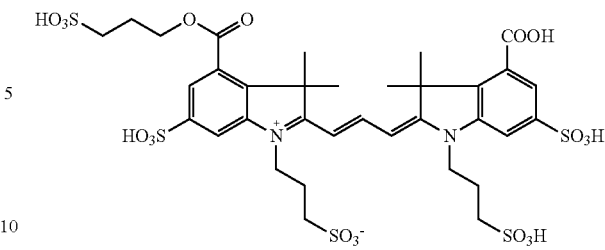

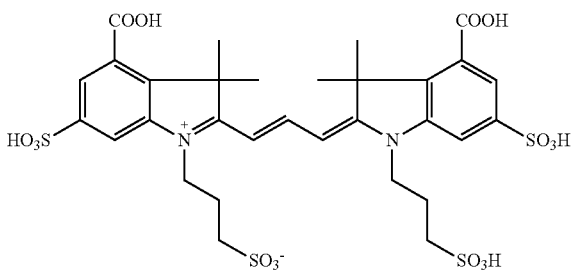

1.32 Preparation of 1.32A and 1.32B

A solution of 1.31 (35 umol) in 6N HCl (4 mL) was heated in a sealed vial for 5. After cooling to ambient temperature the solvent was evaporated off under reduced pressure and residual solid was purified by reverse-phase HPLC (acetonitrile/0.1 M TEAB gradient) to give 1.32A (22.6 umol, λmax 543 nm, 64.5% yield), 1.32B (11.2 umol, λmax 543 nm, 32% yield) and a small amount of starting material.

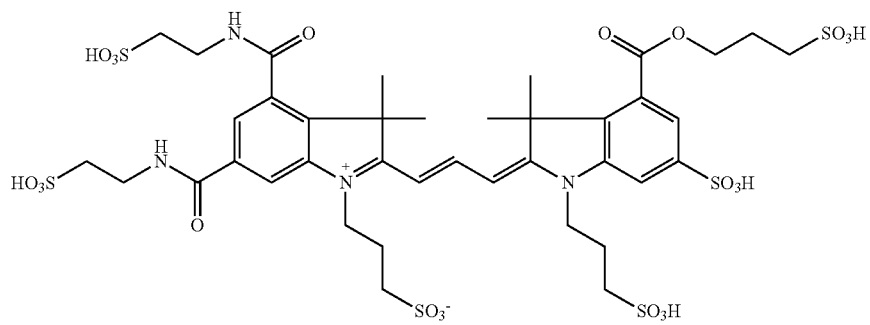

1.33 Preparation of 1.33

To a solution of 2-[(1E)-2-anilinoethenyl]-3,3-dimethyl-1-(3-sulfonatopropyl)-4-(sulfonatopropylcarboxylate)indoleninium-6-sulfonate (3.6 mg, 7.1 umol), 1-(3-sulfonatopropyl)-2,3,3-trimethylindoleninium-4,6-di (sulfonatoethylcarboxyamide) (5 mg, 8.5 umol) in N,N-dimethyl formamide (2 mL) was added acetic anhydride (50 uL) and triethylamine (50 uL) and stirred at ambient temperature for 18 h. Solvent was evaporated off under reduced pressure to give a dark red residue, which was then purified by reverse-phase HPLC (acetonitrile/0.1 M TEAB gradient) to give 0.19 umol of the product (3% yield). λmax (543 nm).

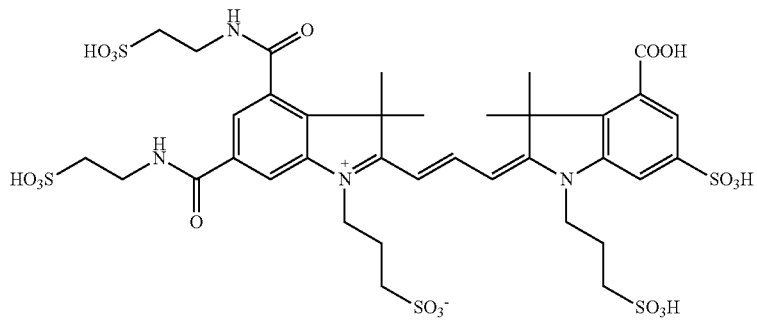

1.34 Preparation of 1.34B

A solution of 1-(3-sulfonatopropyl)-2,3,3-trimethylindoleninium-4,6-di(sulfonatoethylcarboxyamide) (12 mg, 30 umol), 1-(3-sulfonatopropyl)-2,3,3-trimethylindoleninium-4-carboxy-6-sulfonate (10 mg, 17 umol) and triethyl orthoformate (30 uL, 0.18 mmol) in pyridine (1 mL) was heated to reflux for 2 h. Solvent was evaporated off under reduced pressure to give a dark red residue, which was then purified by reverse-phase HPLC (acetonitrile/0.1 M TEAB gradient) to give 3 carbocyanine dyes, 1.34A (λmax, 543 nm), 1.34B (λmax, 544 nm) and a small amount of the tetraamide symmetrical dye.

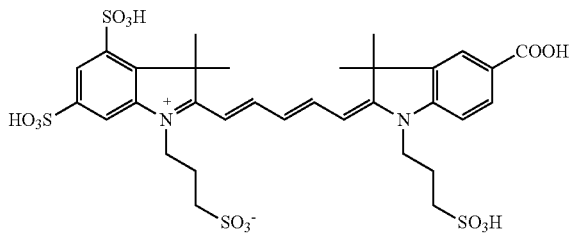

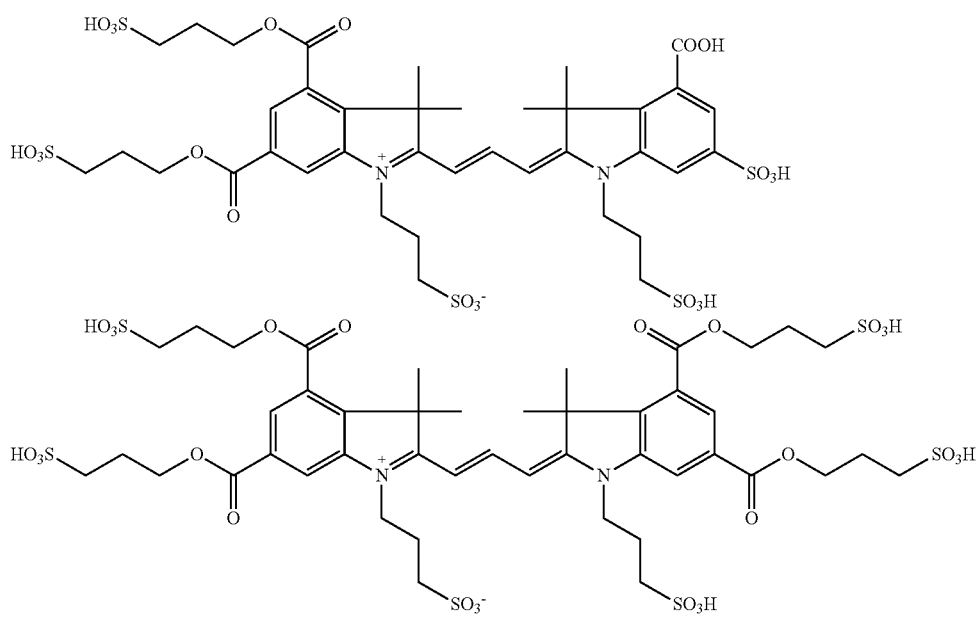

1.35 Preparation of 1.35B and 1.35C

A solution of 1-(3-sulfonatopropyl)-2,3,3-trimethylindoleninium-4,6-di(sulfonatopropylcarboxylate) (25.6 mg, 41.7 umol), 1-(3-sulfonatopropyl)-2,3,3-trimethylindoleninium-4-carboxy-6-sulfonate (16.9 mg, 41.7 umol), KOAc (12.5 mg) and triethyl orthoformate (30 uL, 0.18 mmol) in $H_2O$ (250 uL) and MeOH (1 mL) was heated to reflux for 2 h. Solvent was evaporated off under reduced pressure to give a dark red residue, which was then purified by reverse-phase HPLC (acetonitrile/0.1 M TEAB gradient) to give 3 carbocyanine dyes, 1.35A (λmax, 543 nm), 1.35B (λmax, 542 nm) and the tetra-ester symmetrical dye 1.35C (λmax, 540 nm).

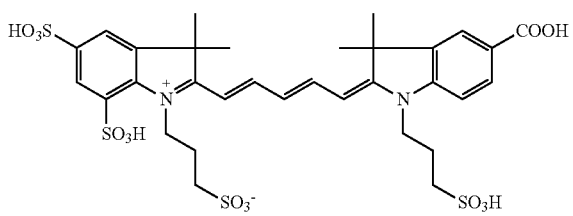

1.36 Preparation of 1.36A and 1.36B

A solution of 2-[(1E,3E)-4-anilinobuta-1,3-dienyl]-3,3-dimethyl-1-(3-sulfonatopropyl)-3H-indoleninium-5,7-disulfonate and 2-[(1E,3E)-4-anilinobuta-1,3-dienyl]-3,3-dimethyl-1-(3-sulfonatopropyl)-3H-indoleninium-4,6-disulfonate (~6:4, 126 mg, 0.220 mmol), 1-(3-sulfonatopropyl)-2,3,3-trimethylindoleninium-5-carboxylate (71.6 mg, 0.220 mmol) in N,N-dimethylformamide (3 mL) and acetic anhydride (1 mL) and pyridine (1 mL) was stirred at ambient temperature for 24 h. Solvent was evaporated off under reduced pressure to give a dark blue residue, which was then purified by reverse-phase HPLC (acetonitrile/0.1 M TEAB gradient) to give 1.36A (λmax 658 nm) and 1.36B (λmax 653 nm).

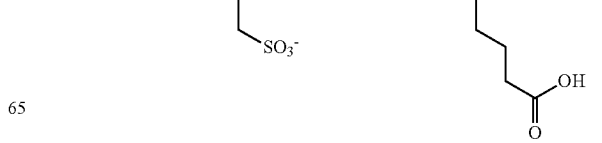

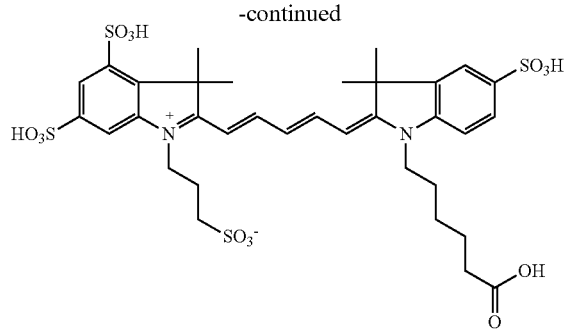

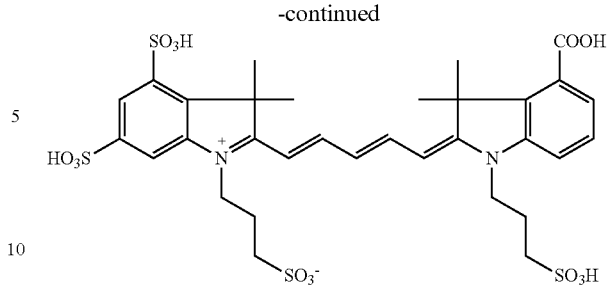

1.37 Preparation of 1.37A and 1.37B

A solution of 2-[(1E,3E)-4-anilinobuta-1,3-dienyl]-3,3-dimethyl-1-(3-sulfonatopropyl)-3H-indoleninium-5,7-disulfonate and 2-[(1E,3E)-4-anilinobuta-1,3-dienyl]-3,3-dimethyl-1-(3-sulfonatopropyl)-3H-indoleninium-4,6-disulfonate (~6:4, 126 mg, 0.220 mmol), 1-carboxypentyl-2,3,3-trimethylindoleninium-5-sulfonate (77.8 mg, 0.220 mmol) in N,N-dimethylformamide (3 mL) and acetic anhydride (1 mL) and pyridine (1 mL) was stirred at ambient temperature for 24 h. Solvent was evaporated off under reduced pressure to give a dark blue residue, which was then purified by reverse-phase HPLC (acetonitrile/0.1 M TEAB gradient) to give 1.37A (λmax 653 nm) and 1.37B (λmax 651 nm).

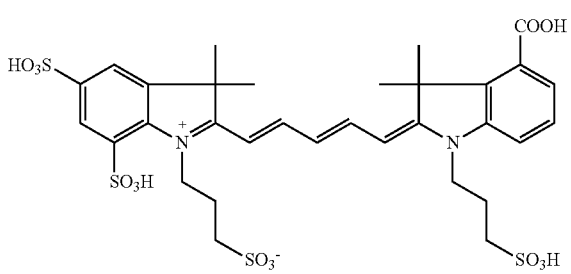

1.38 Preparation of 1.38A and 1.38B

A solution of 2-[(1E,3E)-4-anilinobuta-1,3-dienyl]-3,3-dimethyl-1-(3-sulfonatopropyl)-3H-indoleninium-5,7-disulfonate and 2-[(1E,3E)-4-anilinobuta-1,3-dienyl]-3,3-dimethyl-1-(3-sulfonatopropyl)-3H-indoleninium-4,6-disulfonate (~6:4, 161 mg, 0.282 mmol), 1-(3-sulfonatopropyl)-2,3,3-trimethylindoleninium-4-carboxylate (70.0 mg, 0.214 mmol) in N,N-dimethylformamide (3 mL) and acetic anhydride (1 mL) and pyridine (1 mL) was stirred at ambient temperature for 24 h. Solvent was evaporated off under reduced pressure to give a dark blue residue, which was then purified by reverse-phase HPLC (acetonitrile/0.1 M TEAB gradient) to give 8.4 umol of a mixture of 1.38A (λmax 650 nm) and 1.38B (λmax 648 nm).

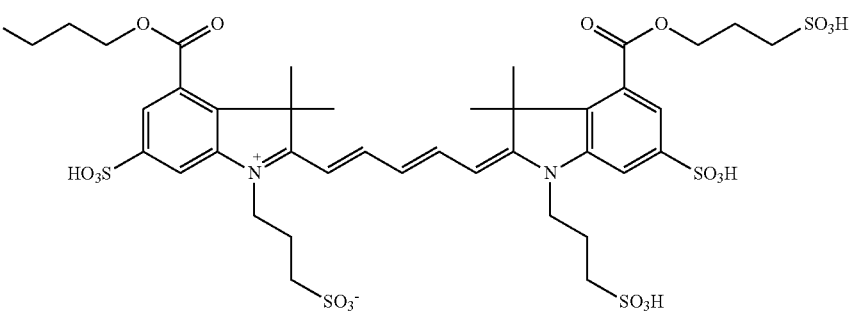

1.39 Preparation of 1.39

A solution of 1-(3-sulfonatopropyl)-2,3,3-trimethylindoleninium-4-(sulfonatopropylcarboxylate)-6-sulfonate (25 mg, 0.062 mmol) and 1,1,3,3-tetraethoxypropane (40 uL, 0.243 mmol) in pyridine (2 mL) was heated to reflux inside a sealed vial for 2 h. Solvent was evaporated off under reduced pressure to give a dark blue residue, which was then purified by reverse-phase HPLC (acetonitrile/0.1 M TEAB gradient) to give the product (λmax 640 nm).

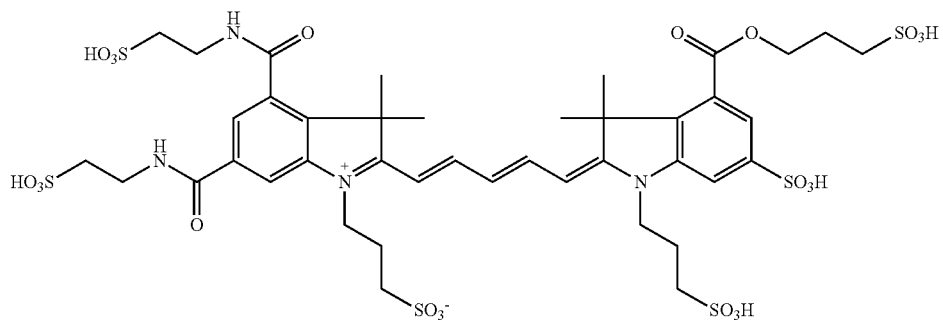

1.40 Preparation of 1.40

To a solution of 2-[(1E,3E)-4-anilinobuta-1,3-dienyl]-3,3-dimethyl-1-(3-sulfonatopropyl)-3H-indoleninium-4-(sulfonatopropylcarboxylate)-6-sulfonate (6.3 mg, 12 umol) and 1-(3-sulfonatopropyl)-2,3,3-trimethylindoleninium-4,6-di (sulfonatoethyllcarboxyamide (7.6 mg, 13 umol) in N,N-dimethylformamide (2 mL) was added acetic anhydride (50 uL), triethylamine (50 uL) and stirred at ambient temperature for 18 h. Solvent was evaporated off under reduced pressure to give a dark blue residue, which was then purified by reverse-phase HPLC (acetonitrile/0.1 M TEAB gradient) to give 3 umol of the product (25% yield). λmax (640 nm).

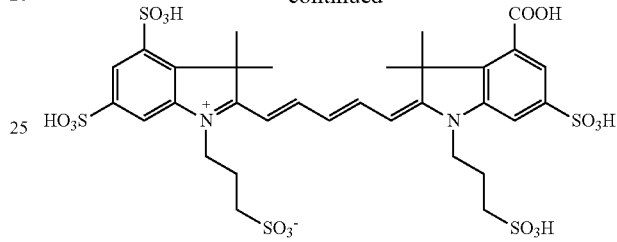

-continued

1.41 Preparation of 1.41A and 1.41B

To a solution of 2-[(1E,3E)-4-anilinobuta-1,3-dienyl]-3,3-dimethyl-1-(3-sulfonatopropyl)-3H-indoleninium-4-carboxy-6-sulfonate (9.3 mg, 16 umol), a 6:4 mixture of 1-(3-sulfonatopropyl)-2,3,3-trimethylindoleninium-5,7-disulfonate and 1-(3-sulfonatopropyl)-2,3,3-trimethylindoleninium-4,6-disulfonate (8.5 mg, 19 umol) in N,N-dimethylformamide (1 mL) was added acetic anhydride (100 uL) and triethylamine (100 uL) and stirred at ambient temperature for 18 h. Solvent was evaporated off under reduced pressure to give a dark blue residue, which was then purified by reverse-phase HPLC (acetonitrile/0.1 M TEAB gradient) to give a mixture of the product (8.5%), 1.41A (λmax 650 nm) and 1.41B (λmax 648 nm).

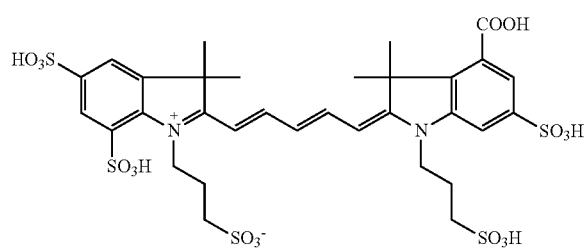

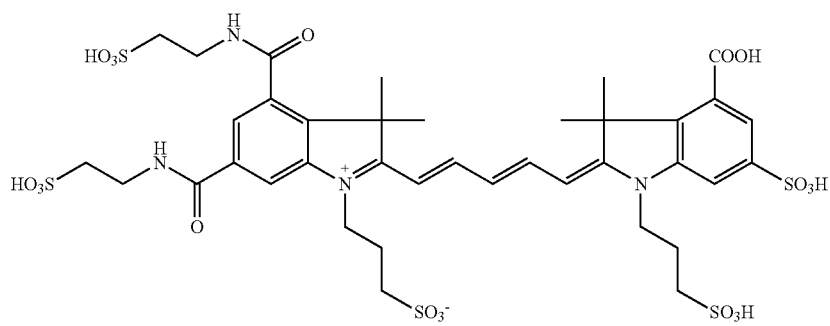

1.42 Preparation of 1.42

To a solution of 2-[(1E,3E)-4-anilinobuta-1,3-dienyl]-3,3-dimethyl-1-(3-sulfonatopropyl)-3H-indoleninium-4-carboxy-6-sulfonate (26.6 mg, 46 umol), 1-(3-sulfonatopropyl)-2,3,3-trimethylindoleninium-4,6-di(sulfonatoethyl)carboxyamide (27 mg, 46 umol) in N,N-dimethylformamide (1 mL) was added acetic anhydride (100 uL) and triethylamine (100 uL) and stirred at ambient temperature for 18 h. Solvent was evaporated off under reduced pressure to give a dark blue residue, which was then purified by reverse-phase HPLC (acetonitrile/0.1 M TEAB gradient) to give the product (9.6 umol, 21%), (λmax 641 nm).

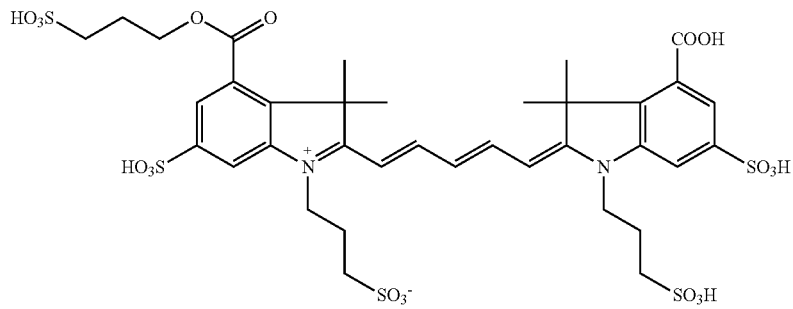

31.43 Preparation of 1.43

To a solution of 2-[(1E,3E)-4-anilinobuta-1,3-dienyl]-3,3-dimethyl-1-(3-sulfonatopropyl)-3H-indoleninium-4-carboxy-6-sulfonate (11 mg, 19 umol), 1-(3-sulfonatopropyl)-2,3,3-trimethylindoleninium-4-(sulfonatopropylcarboxylate)-6-sulfonate (10 mg, 19 umol) in N,N-dimethylformamide (1 mL) was added acetic anhydride (100 uL) and triethylamine (100 uL) and stirred at ambient temperature for 18 h. Solvent was evaporated off under reduced pressure to give a dark blue residue, which was then purified by reverse-phase HPLC (acetonitrile/0.1 M TEAB gradient) to give the product (3.8 umol, 20%), (λmax 640 nm).

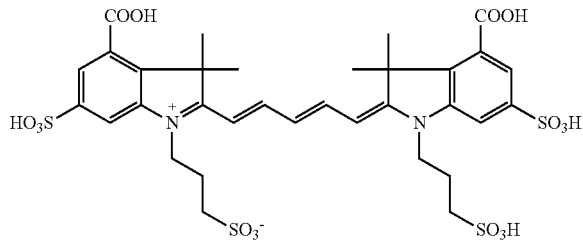

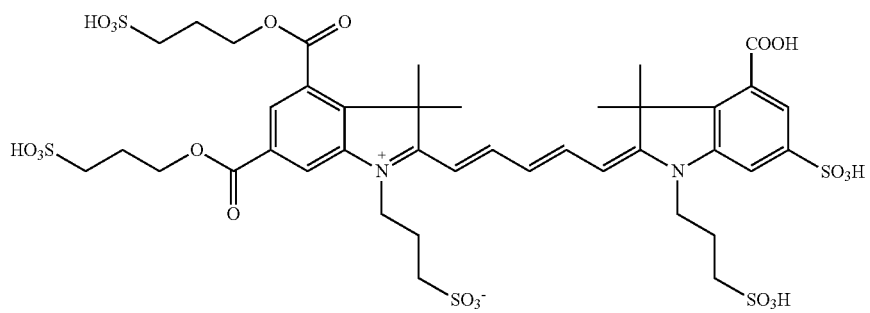

1.44 Preparation of 1.44

To a solution of 2-[(1E,3E)-4-anilinobuta-1,3-dienyl]-3,3-dimethyl-1-(3-sulfonatopropyl)-3H-indoleninium-4-carboxy-6-sulfonate (6.4 mg, 10 umol), 1-(3-sulfonatopropyl)-2,3,3-trimethylindoleninium-4,6-di(sulfonatopropylcarboxylate) (6.0 mg, 10 umol) in N,N-dimethylformamide (1 mL) was added acetic anhydride (100 uL) and triethylamine (100 uL) and stirred at ambient temperature for 18 h. Solvent was evaporated off under reduced pressure to give a dark blue residue, which was then purified by reverse-phase HPLC (acetonitrile/0.1 M TEAB gradient) to give the product (1.9 umol, 19%), (λmax 640 nm).

1.45 Preparation of 1.45

A solution of 1-(3-sulfonatopropyl)-2,3,3-trimethylindoleninium-4-carboxy-6-sulfonate (65.2 mg, 0.161 mmol) and 1,1,3,3-tetraethoxypropane (100 uL, 0.61 mmol) in pyridine (2 mL) was heated to reflux inside a sealed vial for 2 h. Solvent was evaporated off under reduced pressure to give a dark blue residue, which was then purified by reverse-phase HPLC (acetonitrile/0.1 M TEAB gradient) to give 15.4 umol (10%) the product (λmax 641 nm).

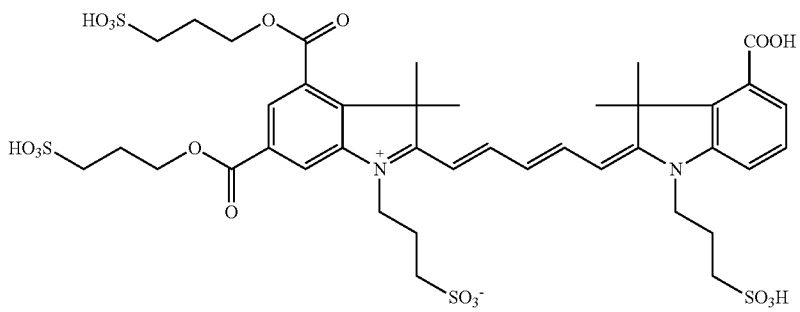

1.46 Preparation of 1.46

To a solution of 2-[(1E,3E)-4-anilinobuta-1,3-dienyl]-3,3-dimethyl-1-(3-sulfonatopropyl)-3H-indoleninium-4-carboxylate (11.2 mg, 24.6 umol), 1-(3-sulfonatopropyl)-2,3,3-trimethylindoleninium-4,6-di(sulfonatopropylcarboxylate) (12.0 mg, 19.5 umol) in N,N-dimethylformamide (0.5 mL) was added acetic anhydride (40 uL) and triethylamine (40 uL) and stirred at ambient temperature for 18 h. Solvent was evaporated off under reduced pressure to give a dark blue residue, which was then purified by reverse-phase HPLC (acetonitrile/0.1 M TEAB gradient) to give the product (6.79 umol, 34.8%), (λmax 638 nm).

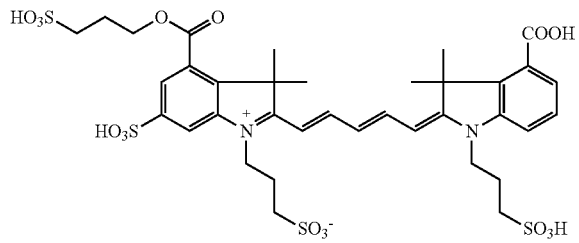

1.47 Preparation of 1.47

To a solution of 2-[(1E,3E)-4-anilinobuta-1,3-dienyl]-3,3-dimethyl-1-(3-sulfonatopropyl)-3H-indoleninium-4-carboxylate (8.6 mg, 19 umol), 1-(3-sulfonatopropyl)-2,3,3-trimethylindoleninium-4-sulfonatopropylcarboxylate-6-sulfonate (10.0 mg, 18.9 umol) in N,N-dimethylformamide (0.5 mL) was added acetic anhydride (40 uL) and triethylamine (40 uL) and stirred at ambient temperature for 18 h. Solvent was evaporated off under reduced pressure to give a dark blue residue, which was then purified by reverse-phase HPLC (acetonitrile/0.1 M TEAB gradient) to give the product (4.3 umol, 23%), (λmax 637 nm).

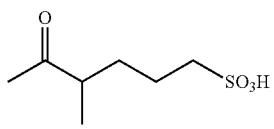

1.48 4-Methyl-5-oxo-1-hexanesulfonate

To a solution of ethyl 2-methylacetoacetate (30.0 mL, 208 mmol) was added 1M t-BuOK in t-BuOH (229 mL, 229 mmol) and 1,3-propanesultone (20.2 mL, 229 mmol) and heated in an oil bath to reflux for 24 h. After cooling to ambient temperature a solid was formed which was triturated with EtOAc (200 mL) and the resultant solid was collected through filtration, washed with ethyl acetate (2×20 mL) and dried. To the dried solid was added 50% HCl (100 mL) and the solution was heated at 110° C. for 24 h. Solvent was evaporated off under reduced pressure and co-evaporated with acetonitrile (2×30 mL) to give 38.3 g (95%) of an oily product. The crude residue was used without further purification.

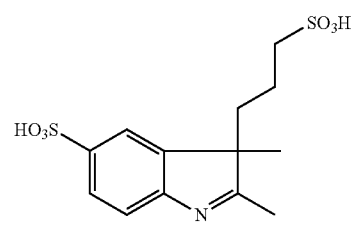 [SMILES: CC1=Nc2ccc(S(=O)(=O)O)cc2C1(C)CCCS(=O)(=O)O]

1.49 2,3-Dimethyl-3-(3-sulfopropyl)indoleninium-5-sulfonate

To an oven dried 100-mL round bottomed flask equipped with a stirring bar, a reflux condenser and a nitrogen balloon was add p-hydrazinobenzenesulfonic acid hemihydrate (2.0 g, 0.010 mol), acetic acid (25 mL), and 4-methyl-5-oxo-1-hexanesulfonate (5.5 g, 0.028 mol). Heated the reaction mixture to reflux with stirring in an oil bath at 115° C. for 30 h. Removed the oil bath and cooled the reaction solution to ambient temperature. Solvent was evaporated off under reduced pressure to dryness. The residual crude product was triturated with MeOH/iPrOH (1:5, 100 mL) and filtered. The solid was then dissolved in MeOH (400 mL) and filtered to remove the undissolved solid (starting material). The filtrate was poured into a beaker and to it was added KOH (1.19 g, 0.021 mol) in iPrOH (400 mL) and stirred. The resultant solid was collected, washed with iPrOH (2×20 mL), EtOAc (2×20 mL) and dried. Placed the solid in an amber bottle and dried in an oven at 50° C. under high vacuum for 18 h. There was obtained 2.94 g (68.4%) of the desired product as a potassium salt.

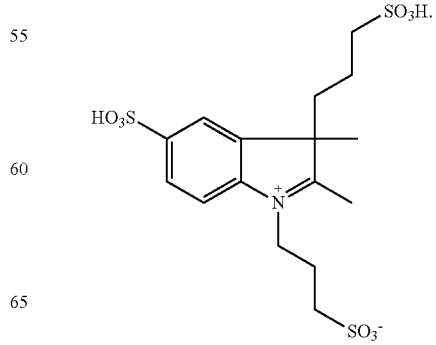

1.50 2,3-Dimethyl-1,3-bis(3-sulfonatopropyl)indoleninium-5-sulfonate

To an oven dried 50-mL round bottom flask equipped with a stir bar, condenser, and an argon balloon in an oil bath was added 2,3-dimethyl-3-(3-sulfopropyl)indoleninium-5-sulfonate (530 mg, 1.25 mmol), 1,3-propanesultone (0.554 mL, 626 mmol) and 1,2-dichlorobenzene (5 mL). Heated the oil bath to 135° C. for 24 h. Removed oil bath and cooled the mixture to ambient temperature. Decanted the solvent and triturated the solid with iPrOH (40 mL). The resultant solid was collected, washed with iPrOH (2×50 mL), EtOAc (2×50 mL), ether (2×50 mL) and air dried. The solid was placed in an amber bottle and dried in an oven under high vacuum overnight. The solid product was used without further purification.

Example 2

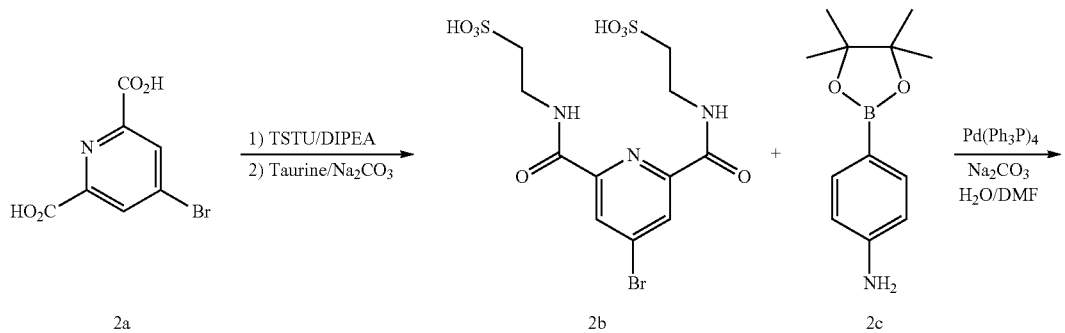

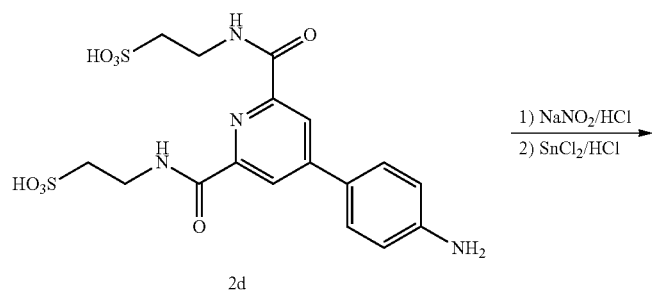

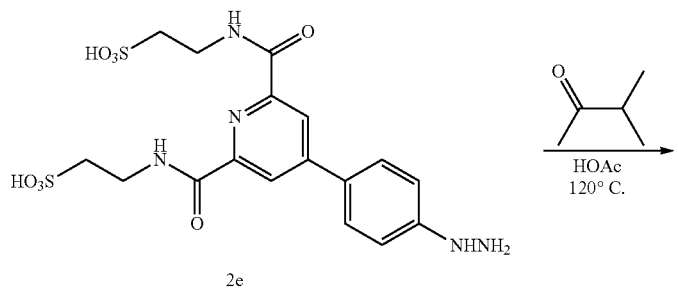

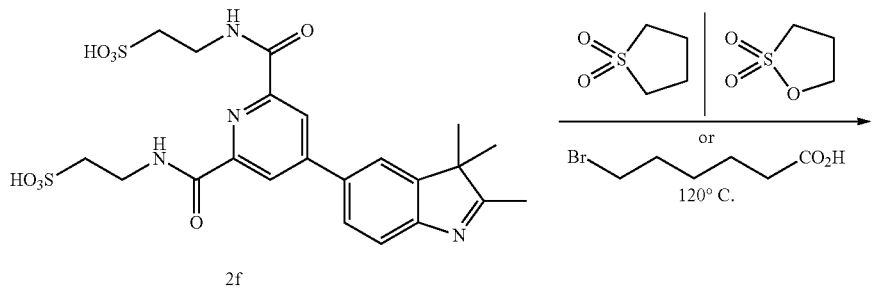

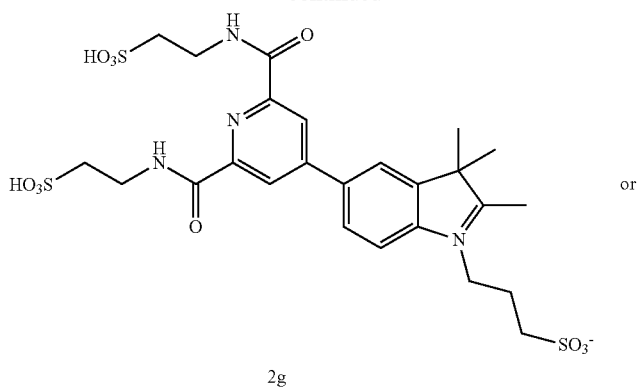
2g
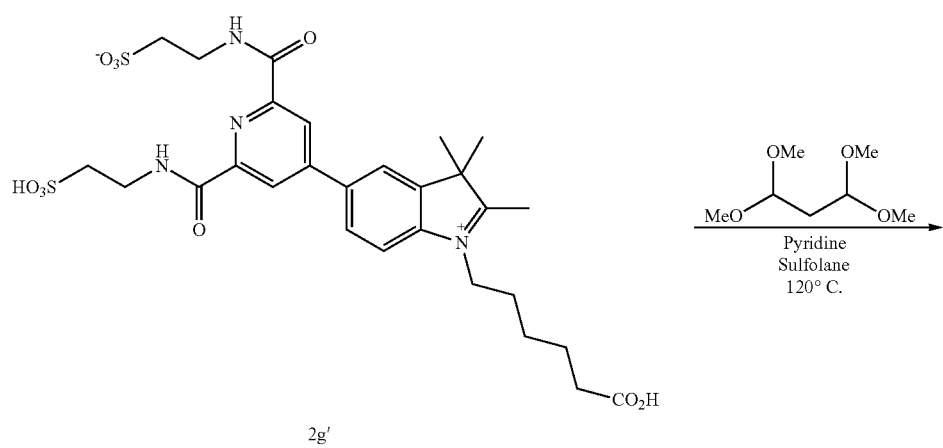
2g'
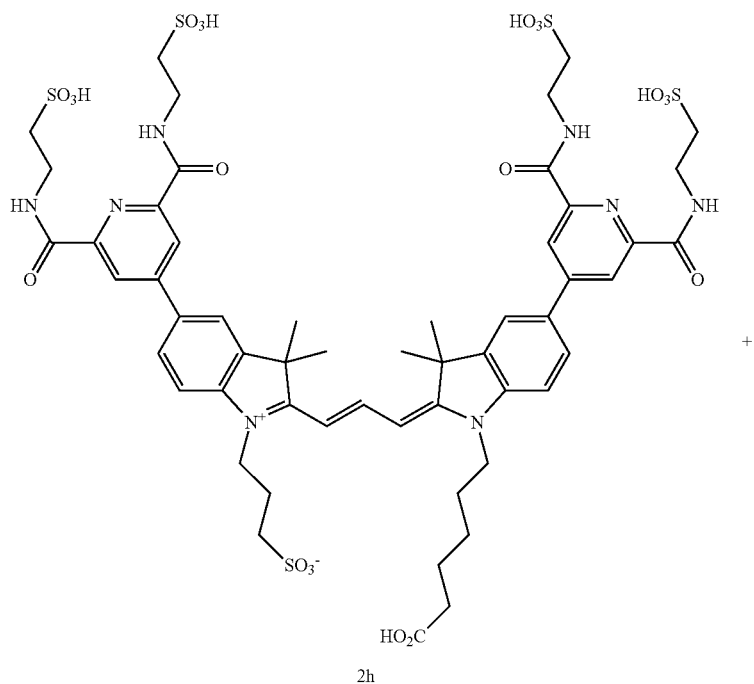
2h

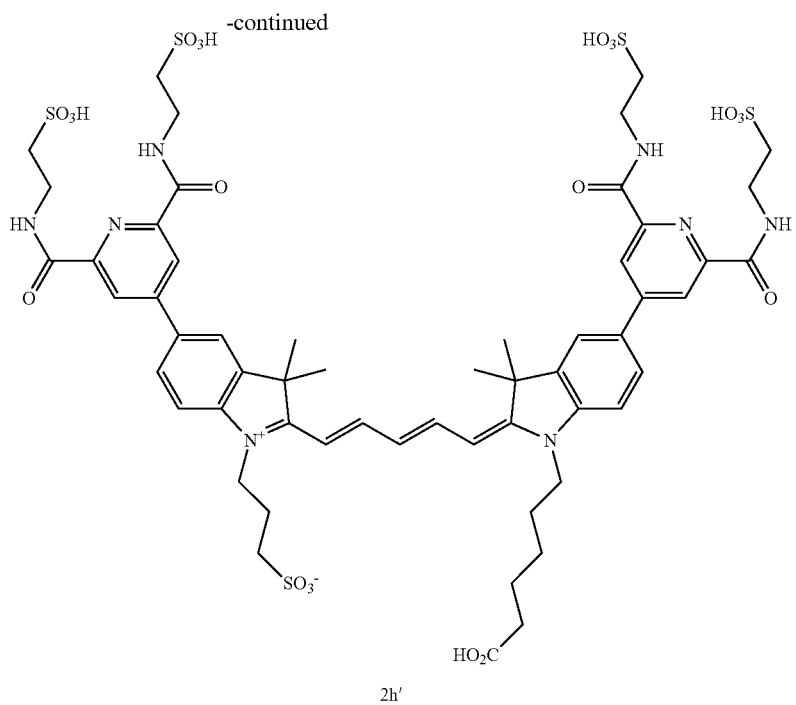

2h′

2.1 Synthesis of 2b

TSTU (3.76 g, 12.54 mmole), in 4 portions, was added to a solution of 4-bromo-2,6-pyridinedicarboxylic acid (2a, 1.03 g, 4.12 mmole) and diisopropylethylamine (1.68 g, 13.0 mmole) in 20 mL DMF at 4° C. over 3 min. The reaction was stirred for 10 min, the cooling bath was removed, and stirred for another 1 hr. This DMF solution was added to a solution of taurine (12.0 g, 95.8 mmole) and Na₂CO₃ (16.2 g, 152.8 mmole) in 300 mL of DMF/H₂O (1:10) over 20 min at room temperature. The reaction was stirred for another 30 min after the addition was completed. The product was purified by reverse phase HPLC eluted with a gradient of CH₃CN over 0.1 N triethylammonium bicarbonate (TEAB) buffer (pH 7). The yield of the desired product (2b) was 1.09 g, also isolated was the mono-taurine amide 0.58 g.

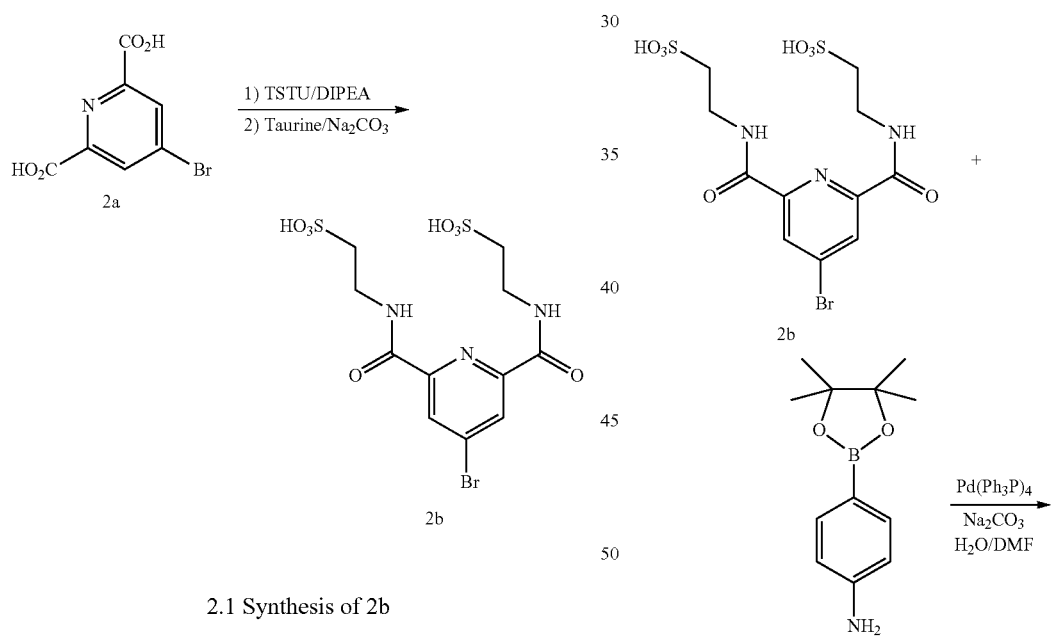

2.2 Synthesis of 2d

A solution of Na$_2$CO$_3$ (214 mg, 2 mmole) in 2.5 mL H$_2$O was added dropwise to a solution of 2b (270 mg, 0.40 mmole) and 2c (100 mg, 0.43 mmole) in 5 mL DMF with stirring. Argon was bubbled through the result mixture for 1 hr, Pd(PPh$_3$)$_4$ (29 mg, 0.025 mmole) was added to the mixture after bubbling for 30 min. The result mixture was heated at 100° C. for 4 hr under a slight positive pressure of argon. After cooling down, the solvents were removed in vacuo, the residue was redissolved in 10 mL 0.1 N TEAB buffer, filtered and purified by reverse phase HPLC eluted with a gradient of CH$_3$CN over 0.1 N TEAB buffer. The yield of the desired product (2.2) was 220 mg.

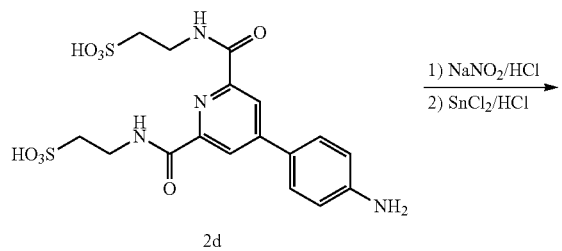

2.3 Synthesis of 2e

A solution NaNO$_2$ (33 mg, 0.47 mmole) in 0.5 mL H$_2$O was added to a solution of 2d (220 mg, 0.32 mmole) in 6 mL 4 N HCl at −5~−10° C. over 5 min. During the course of addition the temperature was kept below −5° C. The reaction was stirred for another 15 min after the addition was completed. SnCl$_2$.2H$_2$O (300 mg, 1.33 mmole) in 1 mL 6N HCl, pre-cooled at −5° C., was added dropwise to the reaction at −5° C. over 5 min. The reaction was stirred for 4 hr as the cooling bath gradually warmed to room temperature. The reaction was diluted with 10 mL H$_2$O, filtered, neutralized with 1 M NaOH to pH 9, and purified by reverse phase HPLC eluted with a gradient of CH$_3$CN over 0.1 N TEAB buffer. The yield of the product (DS374-28) was 172 mg.

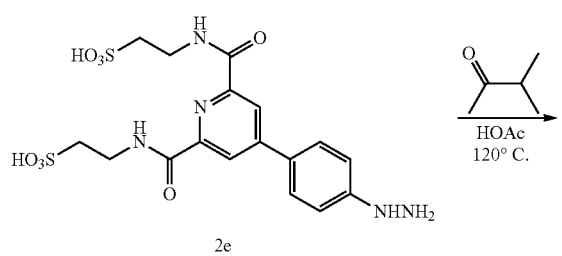

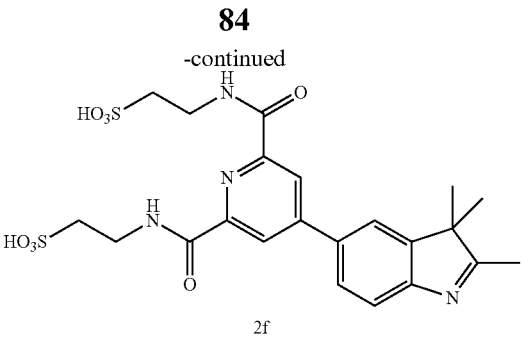

2.4 Synthesis of 2f

A solution of 2e (172 mg, 0.25 mmole) and methyl isopropyl ketone (130 mg, 1.5 mmole) in 5 mL of HOAc was heated at 120° C. for 6 hr. HOAc was removed in vacuo, the residue redissolved in 0.1 N TEAB, filtered, and purified by reverse phase HPLC eluted with a gradient of CH3CN over 0.1 N TEAB buffer. The yield of the product was 101 mg.

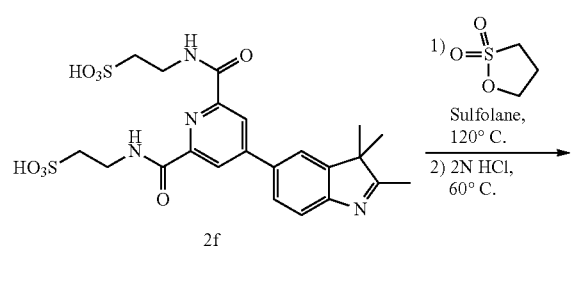

2.5 Synthesis of 2g 2f (40 mg, 0.054 mmole) dissolved in 0.5 mL of sulfolane at 80° C. was added 1,3-Propanesultone (67 mg, 0.54 mmole) with stirring. The reaction was heated to 120° C. for 1.5 hr. After cooling down the reaction was diluted with 10 mL 0.1 N TEAB, filtered, and purified by reverse phase HPLC eluted with a gradient of CH$_3$CN over 0.1 N TEAB buffer. The yield of the product was 36 mg.

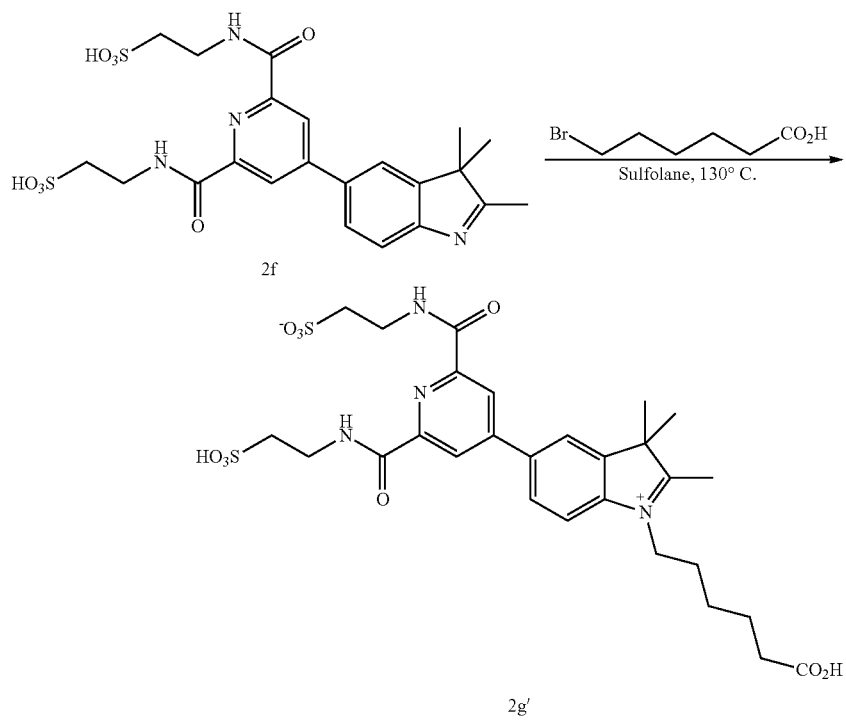
2.6 Synthesis of 2g'
2f (60 mg, 0.081 mmole) dissolved in 0.6 mL of sulfolane at 80° C. was added 6-bromohexanoic acid (222 mg, 1.13 mmole) with stirring. The reaction was heated to 130° C. for 3 hr. After cooling down the reaction was diluted with 10 mL 0.1 N TEAB, filtered, and purified by reverse phase HPLC eluted with a gradient of CH3CN over 0.1 N TEAB buffer. The yield of the product was 33 mg.
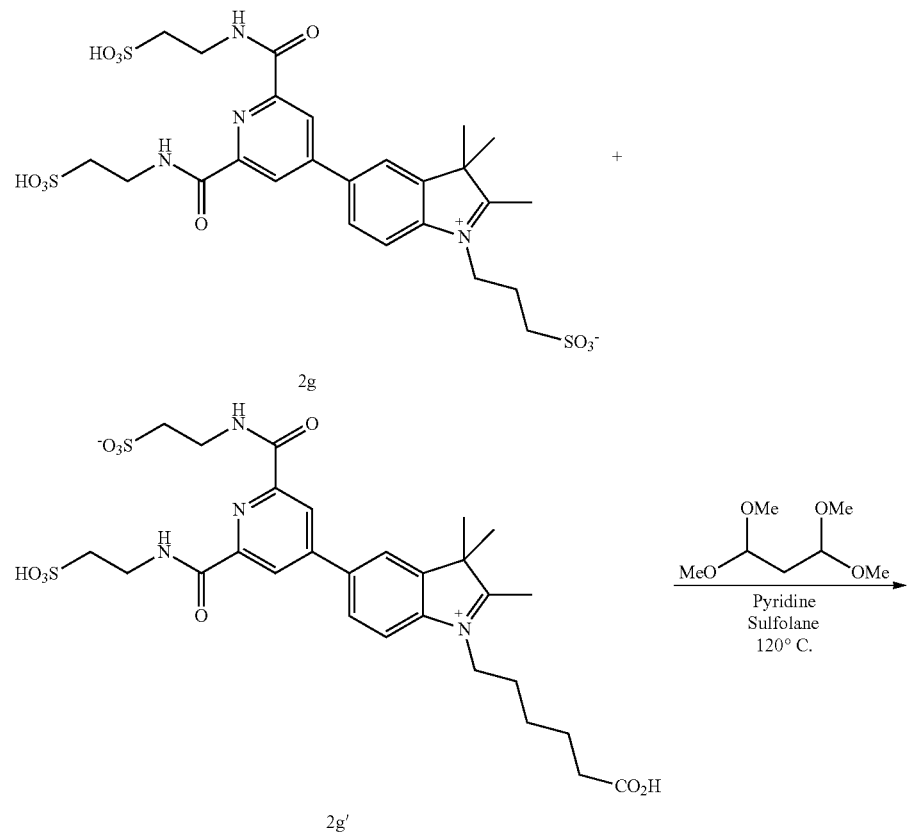

-continued

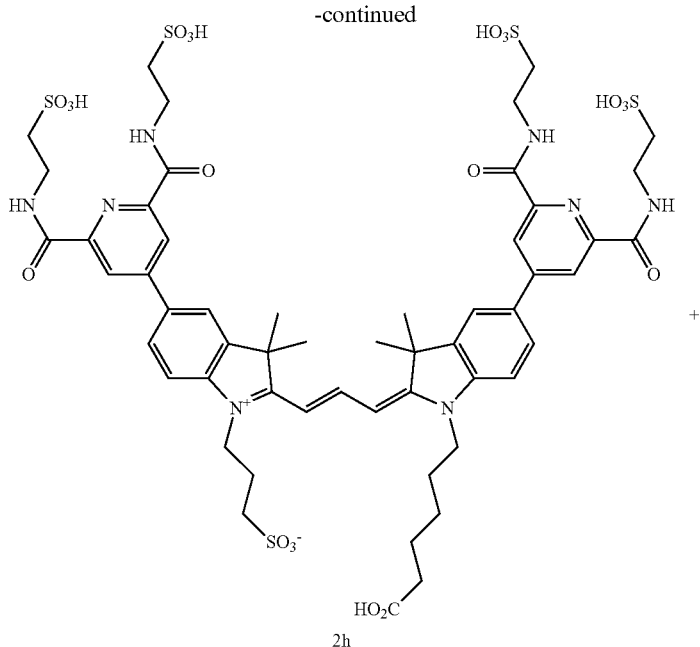
2h

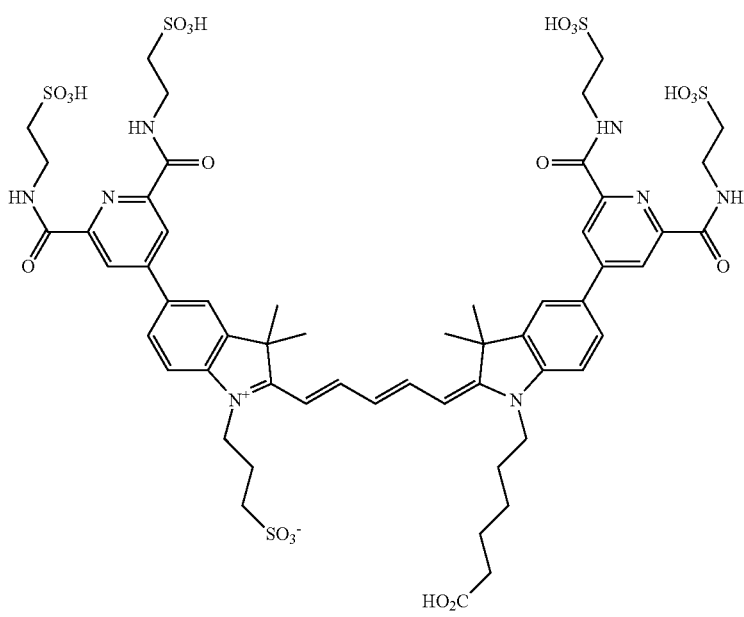
2h'

2.7. Synthesis of 2h and 2h'

2g (10 mg, 0.01 mmole) and 2g' (10 mg, 0.01 mmole) dissolved in 0.3 mL of sulfolane and 0.2 mL of pyridine at 80° C. was added 1,1,3,3 tetramethoxypropane (8.2 mg, 0.05 mmole) with stirring. The reaction was heated to 120° C. for 3 hr, during which time additional 1,1,3,3 tetramethoxypropane (8.2 mg, 0.05 mmole) was added to the reaction. After cooling down the reaction was diluted with 10 mL of 0.1 N TEAB, filtered, and purified by reverse phase HPLC eluted with a gradient of CH3CN over 0.1 N TEAB buffer. The yield of the product was 1.9 mg. Also isolated from the reaction was 2h' in 3.1 mg.

Scheme 2: Synthesis of pyridyl methoxyindolenine cyanine dyes
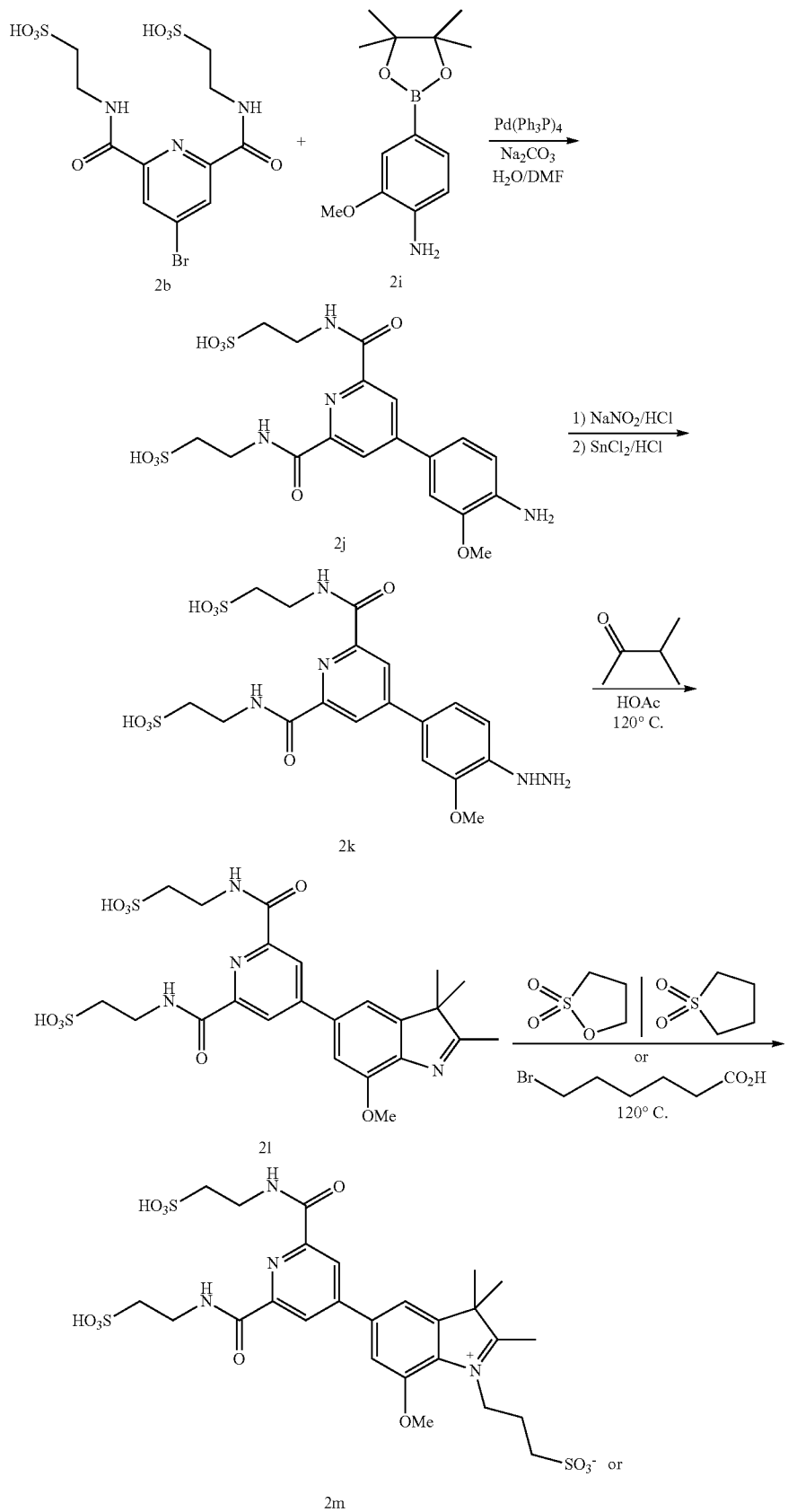

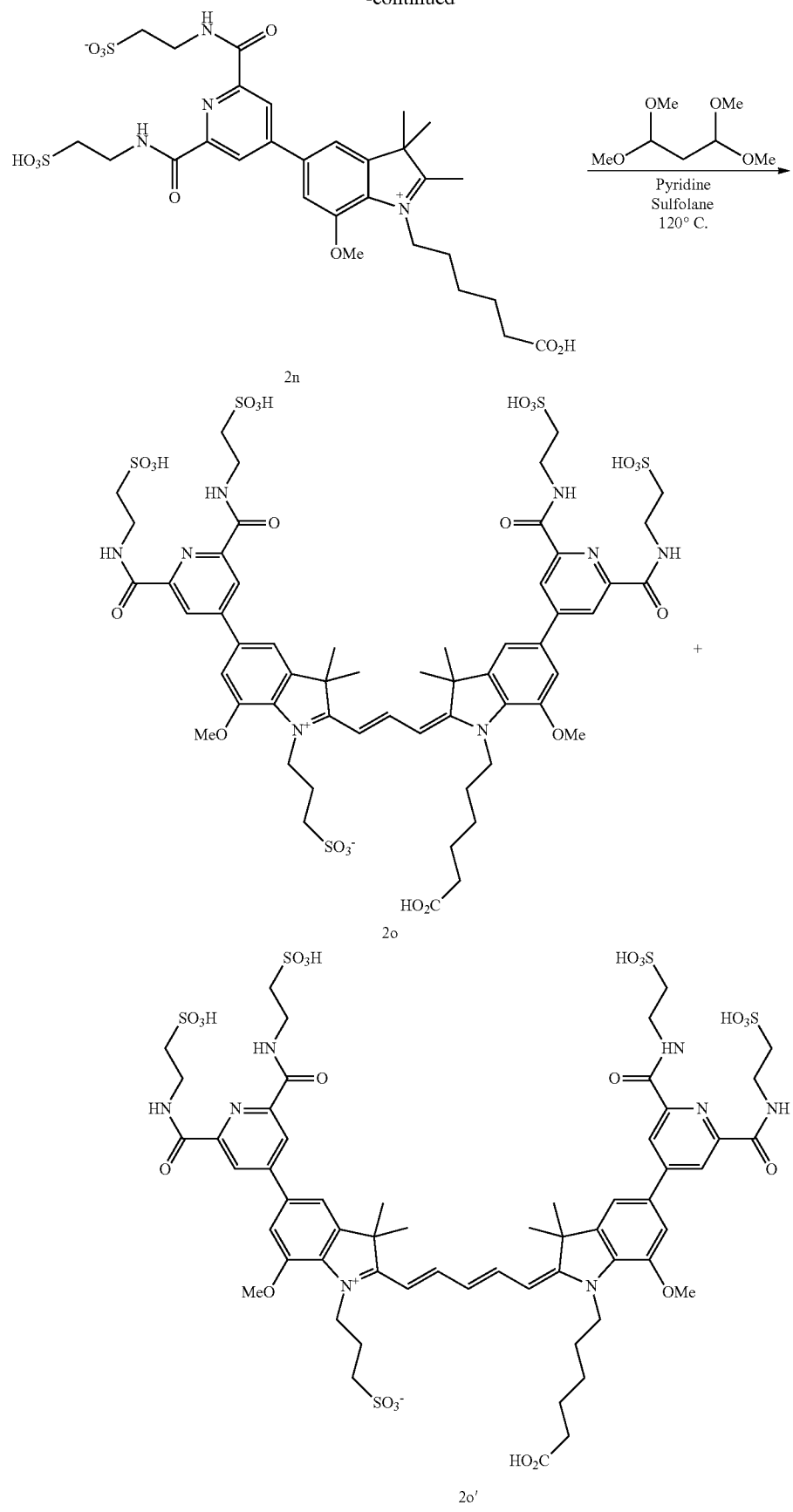

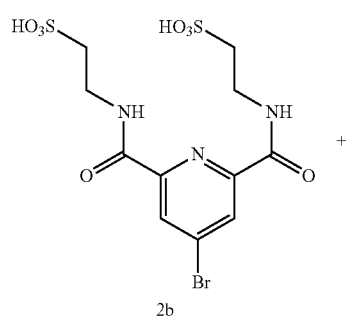

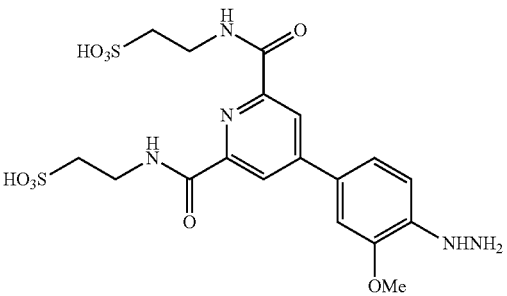

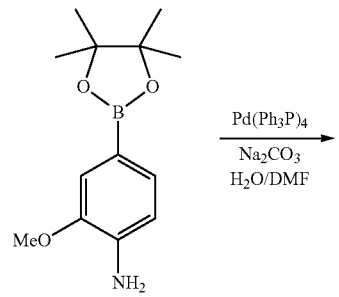

2.8 Synthesis of 2j

A solution of Na$_2$CO$_3$ (144 mg, 1.36 mmole) in 2.5 mL H$_2$O was added dropwise to a solution of 2b (175 mg, 0.27 mmole) and 2i 75 mg, 0.30 mmole) in 5 mL of DMF with stirring. Argon was bubbled through the result mixture for 1 hr, Pd(PPh$_3$)$_4$ (17 mg, 0.015 mmole) was added to the mixture after bubbling for 30 min. The result mixture was heated at 100° C. for 4 hr under a slight positive pressure of argon. The solvents were removed in vacuo, the residue was redissolved in 10 mL 0.1 N TEAB buffer, filtered and purified by reverse phase HPLC eluted with a gradient of CH$_3$CN over 0.1 N TEAB buffer. The yield of the desired product was 137 mg.

2.9 Synthesis of 2k

A solution NaNO$_2$ (27 mg, 0.39 mmole) in 0.5 mL H$_2$O was added to a solution of 2j (137 mg, 0.19 mmole) in 3 mL 4 N HCl at −5∼−10° C. over 2 min. During the course of addition the temperature was kept below −5° C. The reaction was stirred for another 30 min after the addition was completed. SnCl$_2$.2H$_2$O (210 mg, 0.93 mmole) in 0.5 mL 6N HCl, pre-cooled at −5° C., was added dropwise to the reaction at 5° C. over 2 min. The reaction was stirred for 4 hr as the cooling bath gradually warmed to room temperature. The reaction was diluted with 10 mL of H$_2$O, filtered, neutralized with 1 M NaOH to pH 9, and purified by reverse phase HPLC eluted with a gradient of CH3CN over 0.1 N TEAB buffer. The yield of the product was 88 mg.

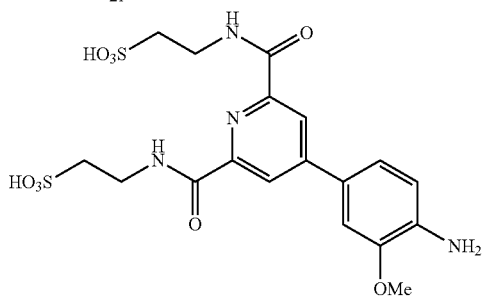

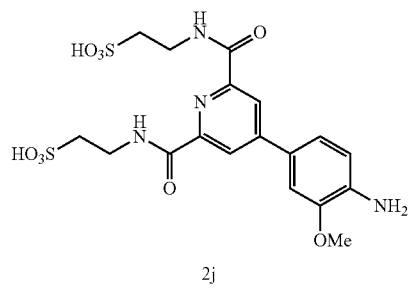

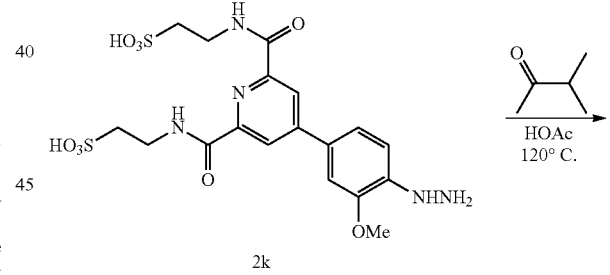

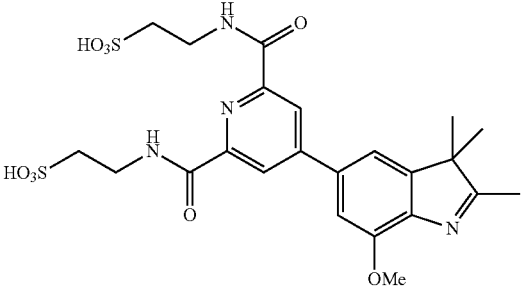

2.10 Synthesis of 2l

A solution of 2k (78 mg, 0.12 mmole) and methyl isopropyl ketone (104 mg, 1.2 mmole) in 3 mL HOAc was heated at 50° C. for 0.5 hr. HOAc was removed in vacuo, the residue redissolved in 0.1 N TEAB, filtered, and purified by reverse phase HPLC eluted with a gradient of $CH_3CN$ over 0.1 N TEAB buffer. The yield of the product was 46 mg.

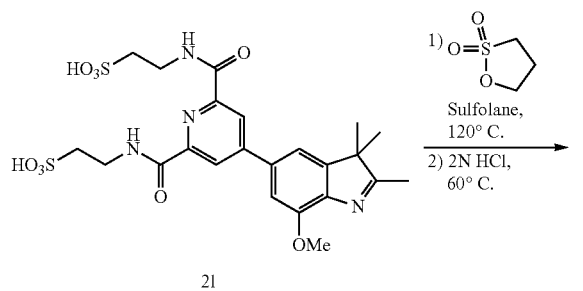

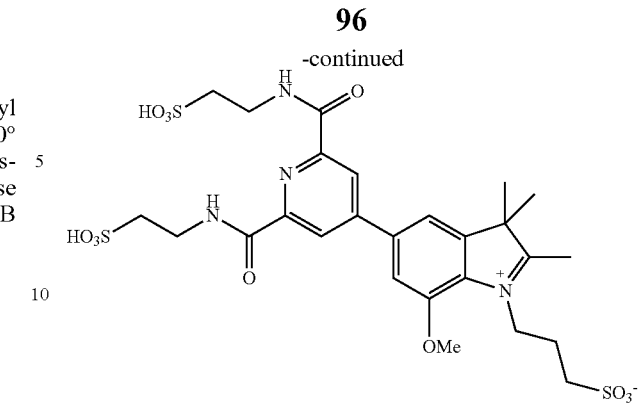

2.11 Synthesis of 2m 2l (22 mg, 0.028 mmole) dissolved in 0.25 mL of sulfolane at 80° C. was added 1,3-Propanesultone (46 mg, 0.37 mmole) with stirring. The reaction was heated to 120° C. for 1.5 hr. After cooling down the reaction was diluted with 10 mL 0.1 N TEAB, filtered, and purified by reverse phase HPLC eluted with a gradient of $CH_3CN$ over 0.1 N TEAB buffer. The yield of the product was 15 mg.

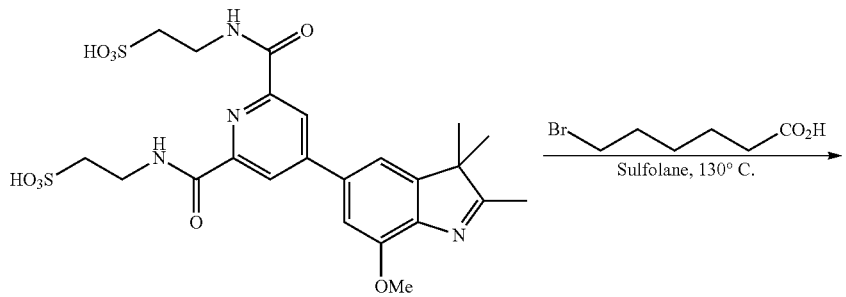

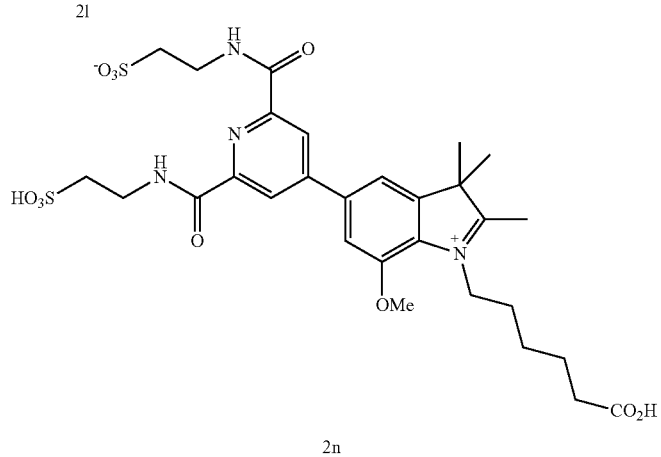

2.12 Synthesis of 2n 2l (50 mg, 0.065 mmole) dissolved in 0.5 mL of sulfolane at 80° C. was added 6-bromohexanoic acid (108 mg, 0.55 mmole) with stirring. The reaction was heated to 130° C. for 3 hr. After cooling down the reaction was diluted with 10 mL 0.1 N TEAB, filtered, and purified by reverse phase HPLC eluted with a gradient of $CH_3CN$ over 0.1 N TEAB buffer. The yield of the product was 26 mg.

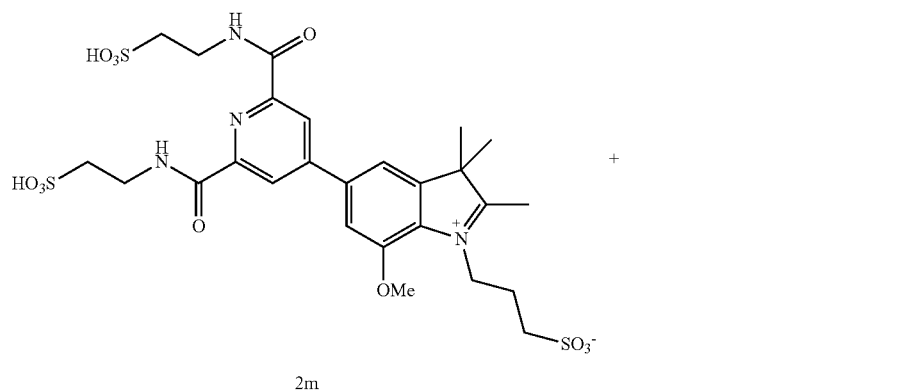
2m
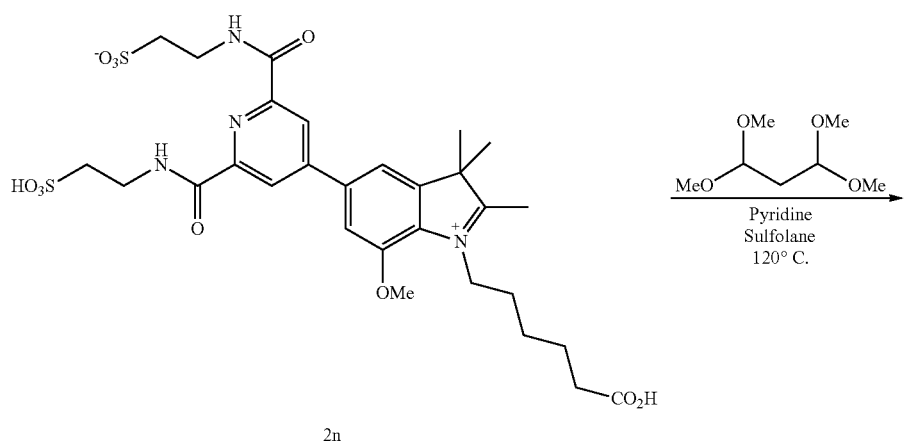
2n
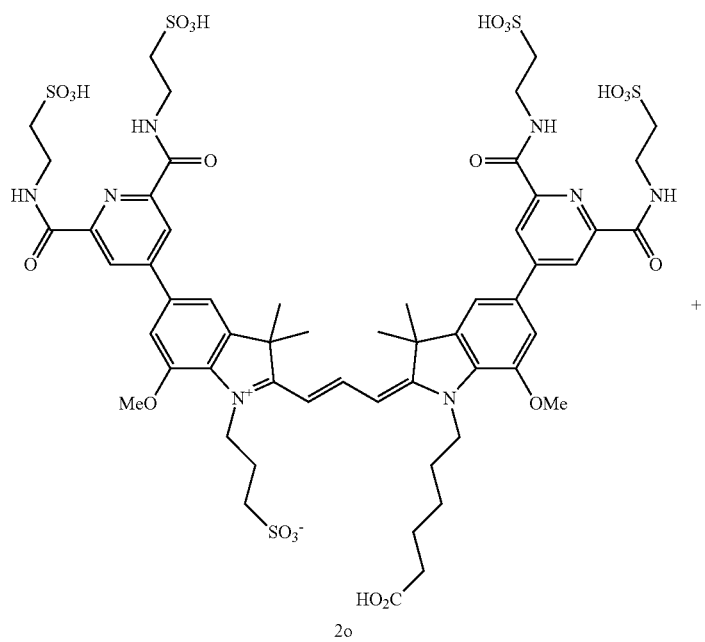
2o

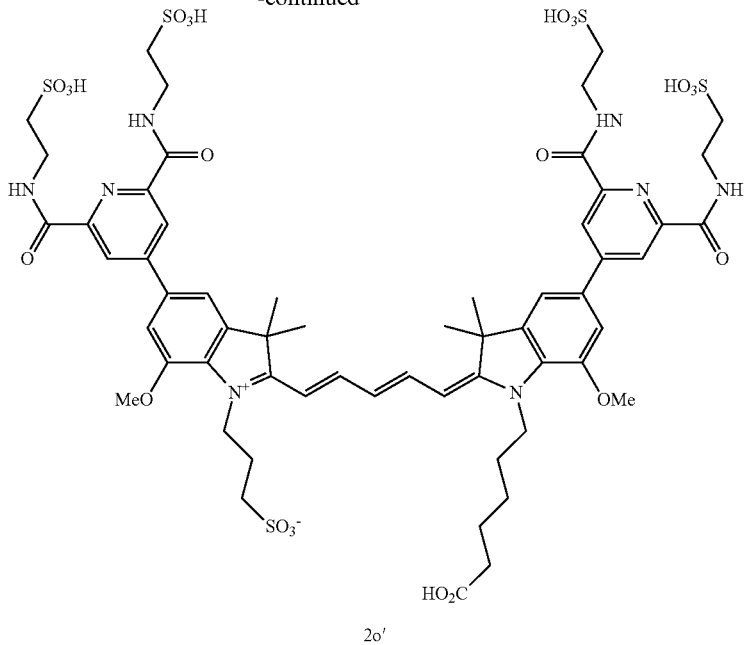

2o'

2.13 Synthesis of 2o and 2o'

2m (15 mg, 0.015 mmole) and 2n (15 mg, 0.015 mmole) dissolved in 0.5 mL of sulfolane and 0.3 mL of pyridine at 80° C. was added 1,1,3,3 tetramethoxypropane (8.2 mg, 0.05 mmole) with stirring. The reaction was heated to 120° C. for 3 hr, during which time additional 1,1,3,3 tetramethoxypropane (8.2 mg, 0.05 mmole) was added to the reaction. After cooling down the reaction was diluted with 10 mL 0.1 N TEAB, filtered, and purified by reverse phase HPLC eluted with a gradient of $CH_3CN$ over 0.1 N TEAB buffer. The yield of the product (2o') was 3.2 mg. Also isolated from the reaction was 2o (3.3 mg).

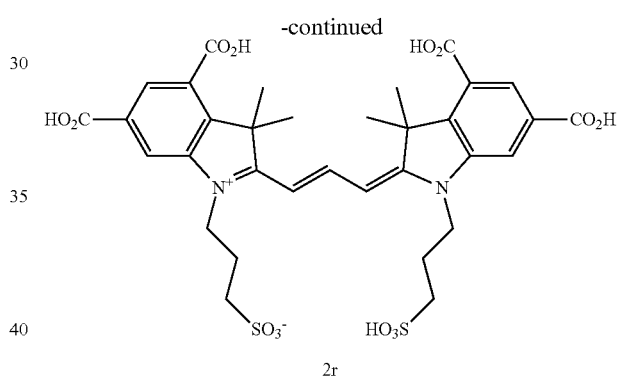

2r

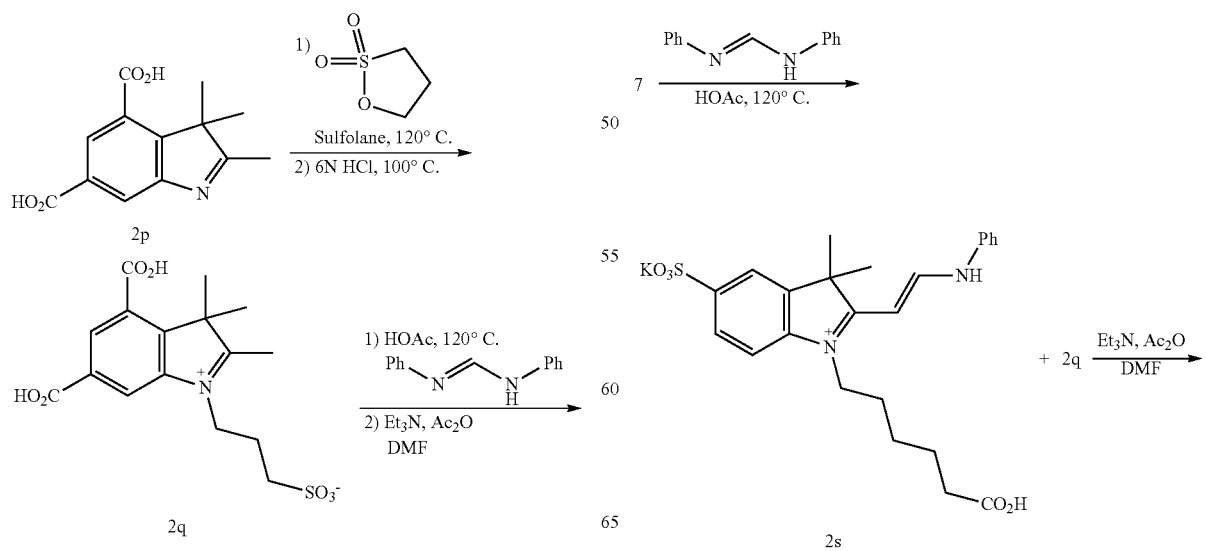

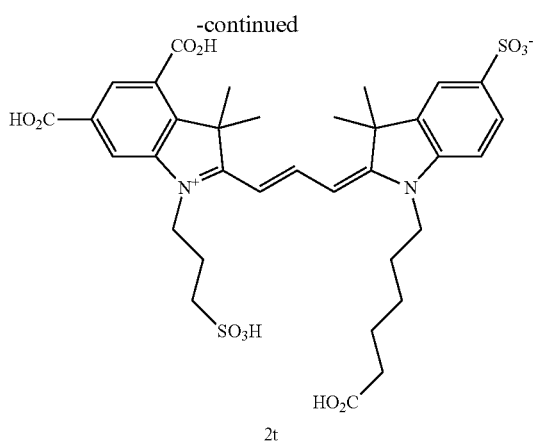

2t

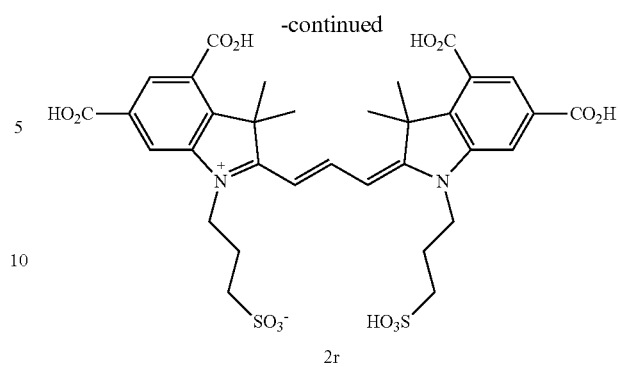

2r

2.15 Synthesis of 2r 2q (20 mg, 0.054 mmole) and diphenyl formamidine (13 mg, 0.064 mmole) was heated in 0.5 mL of HOAc at 120° C. for 2 hr. After cooling down, the reaction was diluted with 5 mL of EtOAc. The precipitate was collected, washed with EtOAc, dried under vacuum, and redissolved in 0.5 mL of DMF. 2q (20 mg, 0.054 mmole) was added to the DMF solution followed by $Et_3N$ (28 mg, 0.27 mmole), $Ac_2O$ (28 mg, 0.27 mmole), and the reaction was stirred for 3 hr at room temperature. The reaction was diluted with 10 mL 0.1 N TEAB, filtered, and purified by reverse phase HPLC eluted with a gradient of $CH_3CN$ over 0.1 N TEAB buffer. The yield of the product was 10.5 mg.

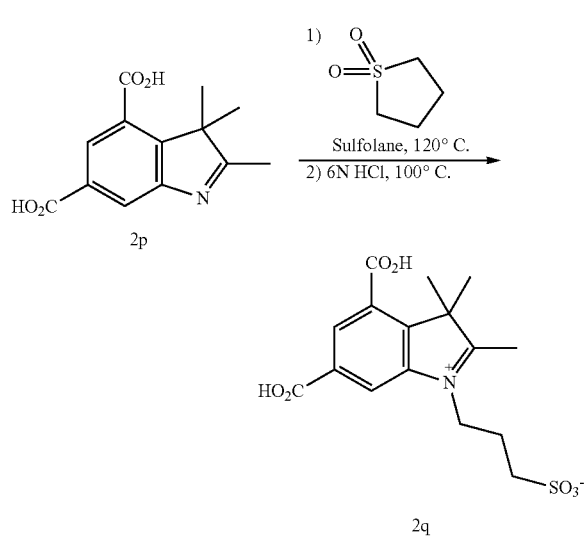

2p

2q

2.14 Synthesis of 2q 2p (500 mg, 2.02 mmole) and 3 mL of 1,3 propanesultone was heated at 120° C. for 3 hr. After cooling down, 15 mL of 6 N HCl was slowly added to the reaction and heated to 100° C. for 5 hr. The reaction was diluted with 15 mL of $CH_3CN$ and filtered. The filtrate was concentrated in vacuo and resuspended in 50 mL of EtOH. The precipitated was collected, washed with EtOH, $Et_2O$ and dried under vacuum. The yield of the product was 614 mg.

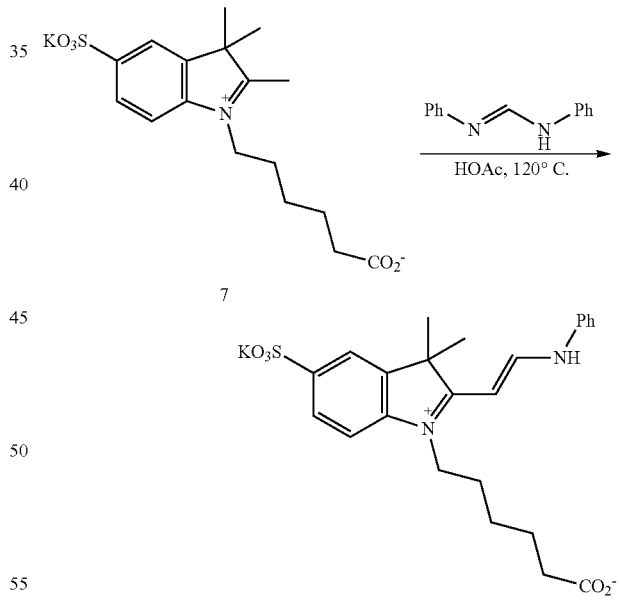

7

2s

2.16 Synthesis of 2s 7 (potassium salt, 180 mg, 0.46 mmole) and diphenyl formamidine (100 mg, 0.51 mmole) was heated in 4 mL of HOAc at 120° C. for 5 hr. During which time more diphenyl formamidine (50 mg, 0.25 mmole) was added to the reaction. After cooling down, the reaction was diluted with 30 mL of EtOAc, the precipitate was collected, washed with EtOAc,

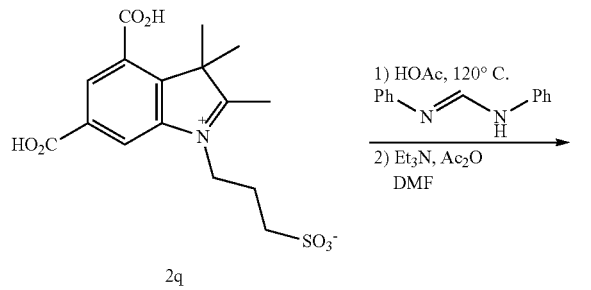

2q

Et₂O, and dried under vacuum. The yield of the crude product was 215 mg and was used without further purification.

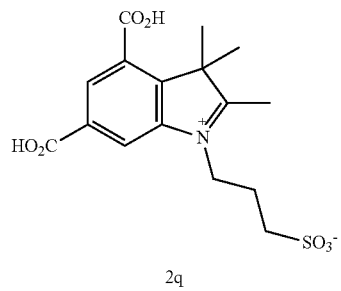

2q

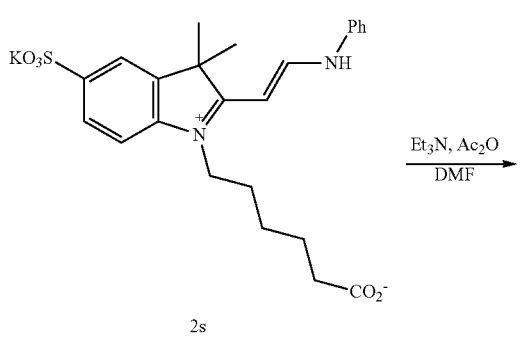

2s

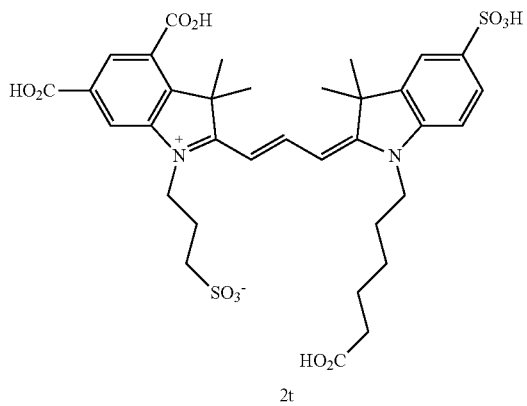

2t

2.17 Synthesis of 2t

To a stirring solution of 2q (50 mg, 0.13 mmole) and 2s (75 mg, crude) in 3 mL of DMF was added Et₃N (66 mg, 0.65 mmole) followed by Ac₂O (66 mg, 0.65 mmole). The reaction was stirred at room temperature for 3 hr and quenched with 12 mL EtOAc. The precipitated was collected and purified by reverse phase HPLC eluted with a gradient of CH₃CN over 0.1 N TEAB buffer. The yield of the product was 24 mg.

Scheme 4: Synthesis of taurine amide indolenine cyanine dyes

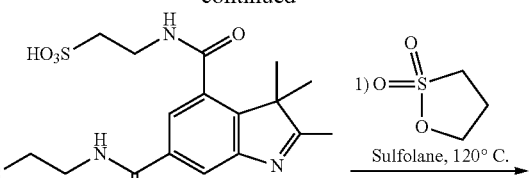

2u

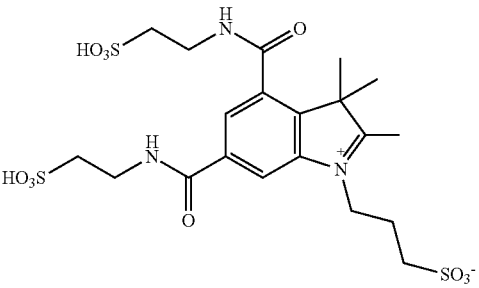

2v

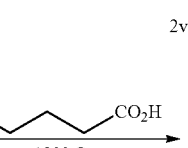

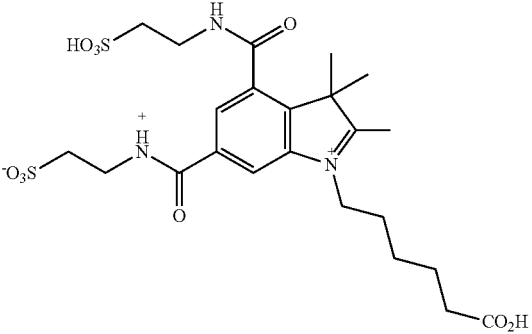

2w

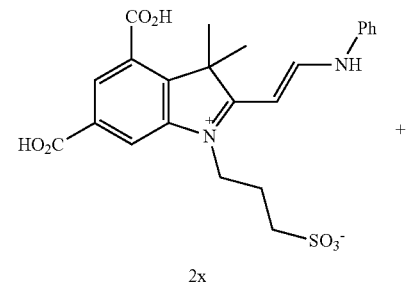

2x

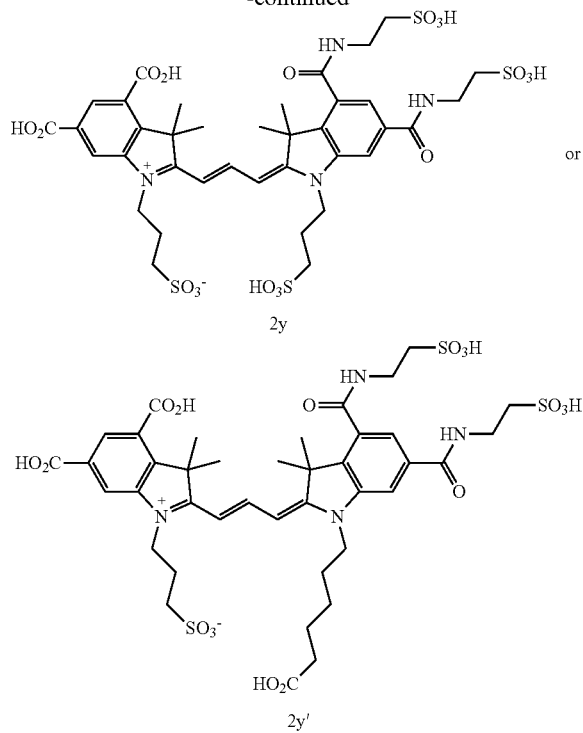

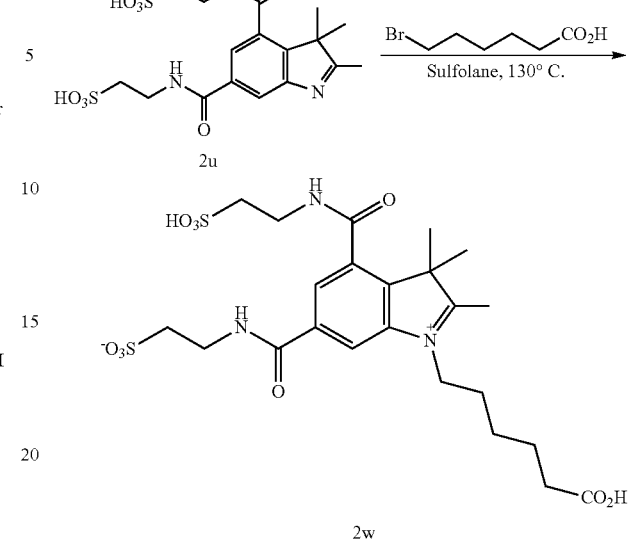

2.19 Synthesis of 2w 2u (200 mg, 0.30 mmole) dissolves in 1 mL of sulfolane at 80° C. was added 6-bromohexanoic acid (197 mg, 1.0 mmole) with stirring. The reaction was heated to 130° C. for 3 hr. During which time more 6-bromohexanoic acid (60 mg, 0.34 mmole) was added to the reaction. After cooling down the reaction was diluted with 10 mL of DMF. The precipitate was collected, washed with 1 mL DMF, EtOAc, Et$_2$O, dried under vacuum. The yield of the crude product was 116 mg and was used without further purification.

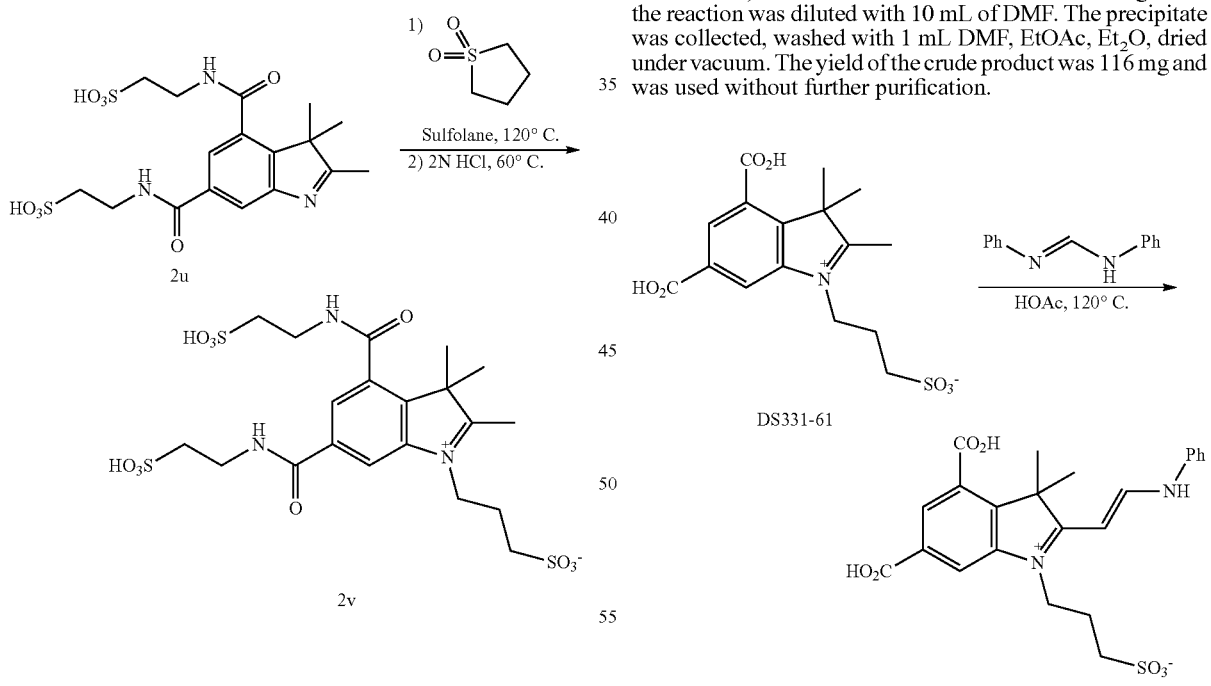

2.18 Synthesis of 2v 2u (267 mg, 0.40 mmole) dissolved in 1 mL of sulfolane at 80° C. was added 1,3 propanesultone (492 mg, 4 mmole) with stirring. The reaction was heated to 120° C. for 1.5 hr. After cooling down the reaction was diluted with 10 mL 0.1 N TEAB, filtered, and purified by reverse phase HPLC eluted with a gradient of CH$_3$CN over 0.1 N TEAB buffer. The yield of the product was 220 mg.

2.20 Synthesis of 2x 2q (37 mg, 0.10 mmole) and diphenyl formamidine (25 mg, 0.12 mmole) was heated in 4 mL of HOAc at 120° C. for 4 hr. During which time more diphenyl formamidine (12 mg, 0.06 mmole) was added to the reaction. After cooling down, the reaction was diluted with 30 mL of EtOAc, the precipitate was collected, washed with EtOAc, Et₂O, and dried under vacuum. The yield of the crude product was 32 mg and was used without further purification.

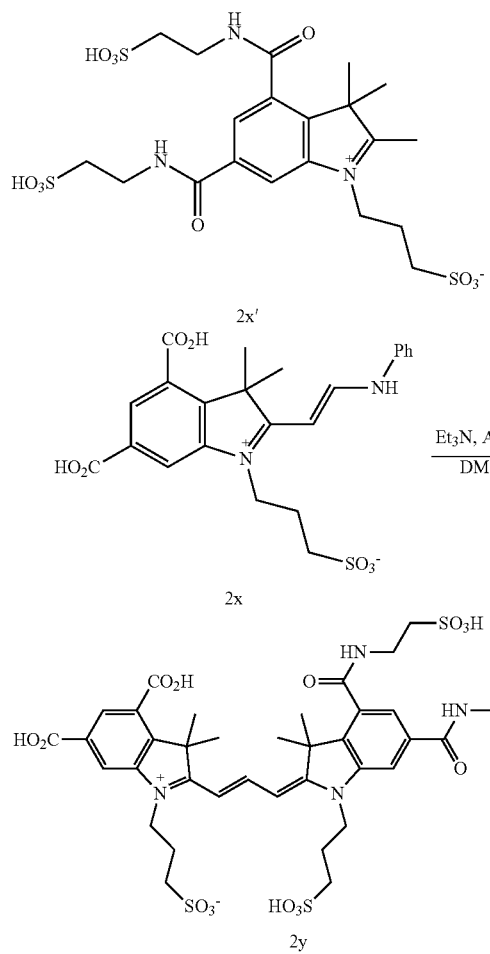

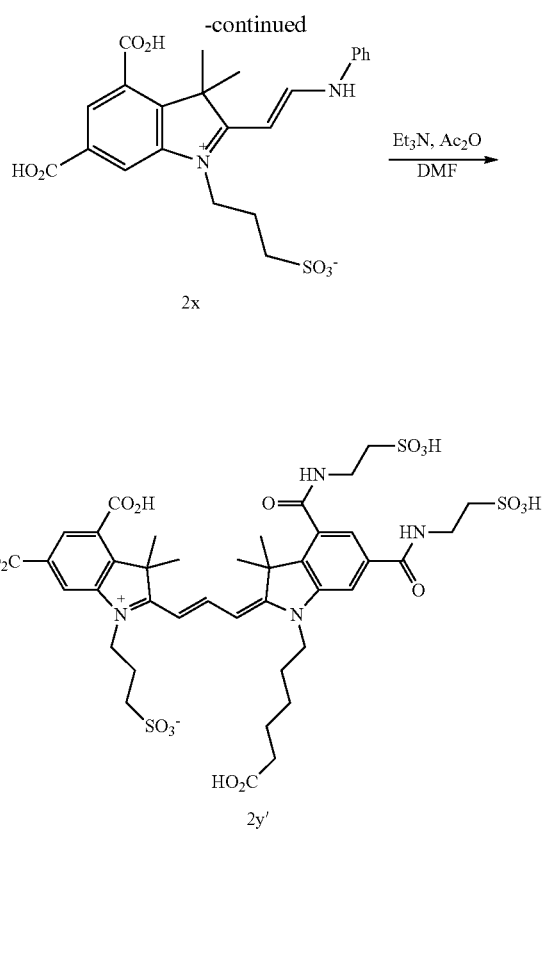

2.21 Synthesis of 2y

To a stirring solution of 2x' (24 mg, 0.027 mmole) and 2x (16 mg, crude) in 0.7 mL of DMF was added Et₃N (14 mg, 0.14 mmole) followed by Ac₂O (14 mg, 0.14 mmole). The reaction was stirred at room temperature for 3 hr and quenched with 4 mL EtOAc. The precipitated was collected and purified by reverse phase HPLC eluted with a gradient of CH₃CN over 0.1 N TEAB buffer. The yield of the product was 6.3 mg.

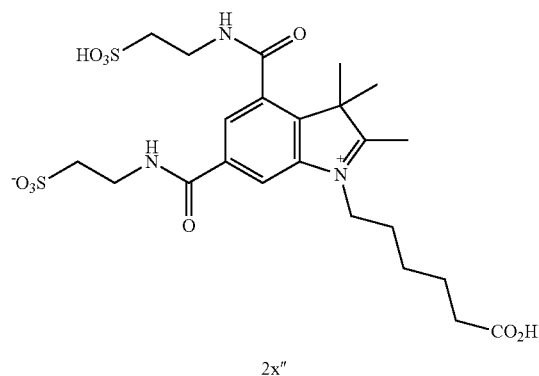

2.22 Synthesis of 2y'

To a stirring solution of 2x" (29 mg, 0.033 mmole) and 2x (16 mg, crude) in 0.7 mL of DMF was added Et3N (16 mg, 0.16 mmole) followed by Ac₂O (16 mg, 0.16 mmole). The reaction was stirred at room temperature for 3 hr and quenched with 4 mL EtOAc. The precipitated was collected and purified by reverse phase HPLC eluted with a gradient of CH₃CN over 0.1 N TEAB buffer. The yield of the product (DS374 140) was 9.6 mg.

Example 3

Scheme 5: Synthesis of taurine amide benzindole cyanine dyes

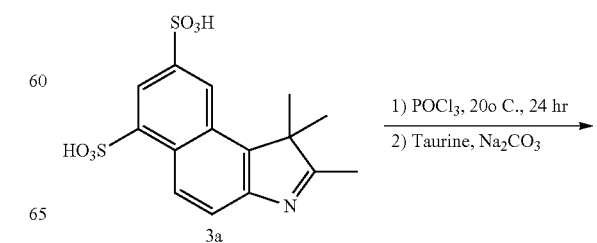

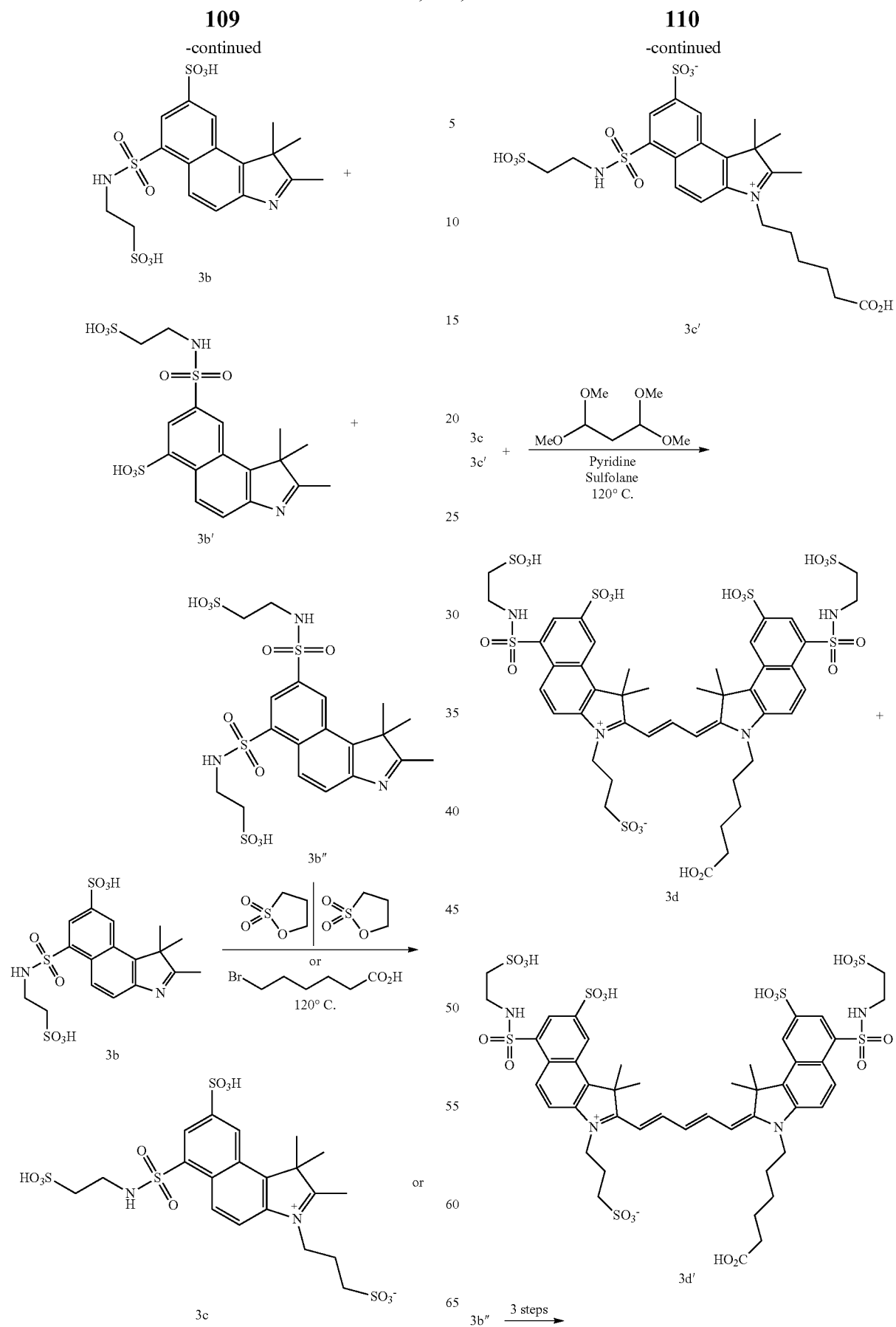

111
-continued
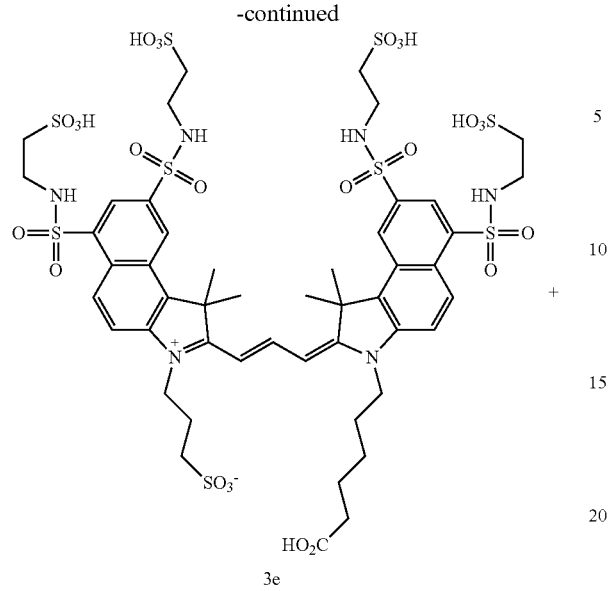
3e
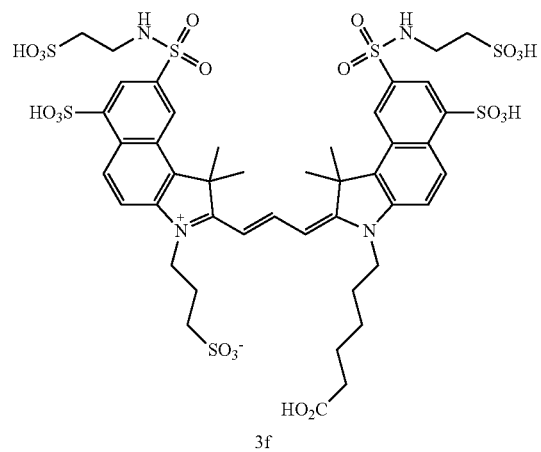
3e'
3b' —3 steps→
3f
112
-continued
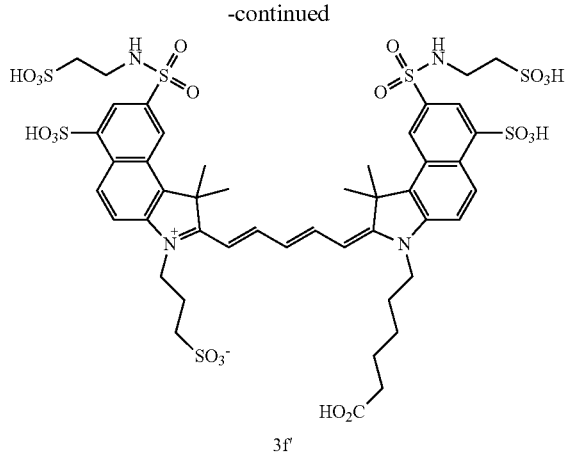
3f'
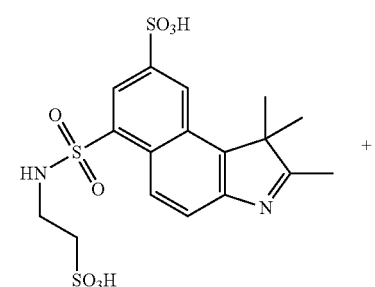
3a
1) POCl₃, 20° C., 24 hr
2) Taurine, Na₂CO₃
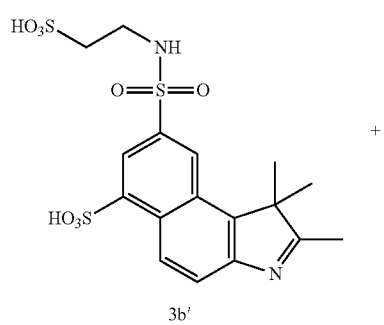
3b
3b'

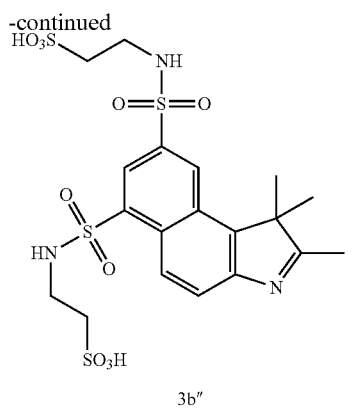

3b″

3.1 Synthesis of 3b, 3b', and 3b″

3a (1.25 g, triethylammonium salt) was stirred with 5 mL of $POCl_3$ at room temperature for 18 hr. $POCl_3$ was removed by rotavap and pumped under vacuum for 15 hr. The residue was dissolved in 10 mL DMF and added dropwise to a solution of taurine (5.5 g, 44 mmole) and $Na_2CO_3$ (14.0 g, 132 mmole) in 250 mL $DMF/H_2O$ (1:9) over 10 min at room temperature. The stirred for 30 min after the addition was completed. The products were purified by reverse phase HPLC eluted with a gradient of CH3CN over 0.1 N TEAB buffer. The yield of the product 3b was 530 mg, 3b' was 260 mg, and 3b″ was 303 mg.

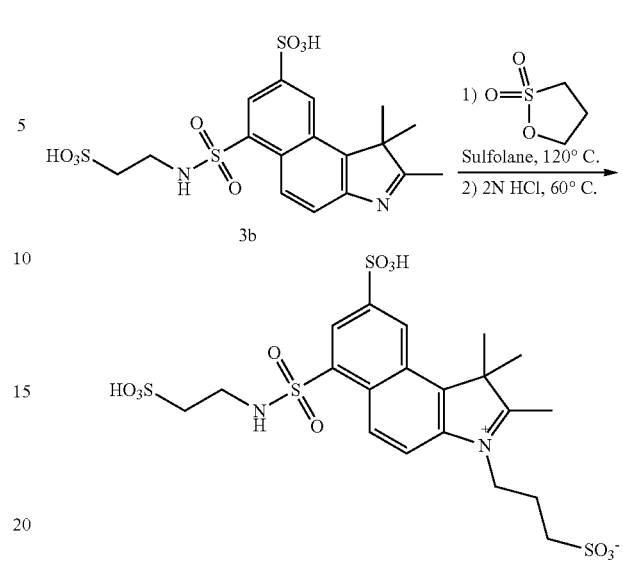

3.2 Synthesis of 3c 3b (67 mg, 0.1 mmole) dissolved in 0.8 mL of sulfolane at 80° C. was added 1,3 propanesultone (87 mg, 0.7 mmole) with stirring. The reaction was heated to 120° C. for 1.2 hr. After cooling down the reaction was diluted with 10 mL 0.1 N TEAB, filtered, and purified by reverse phase HPLC eluted with a gradient of $CH_3CN$ over 0.1 N TEAB buffer. The yield of the product was 54 mg.

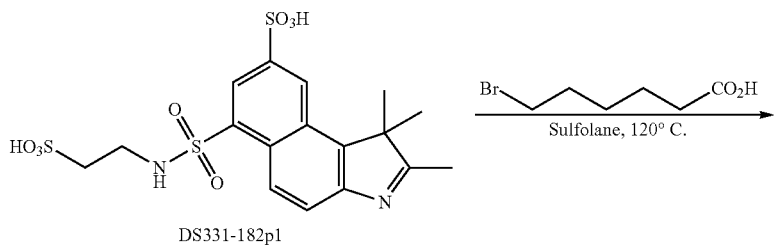

DS331-182p1

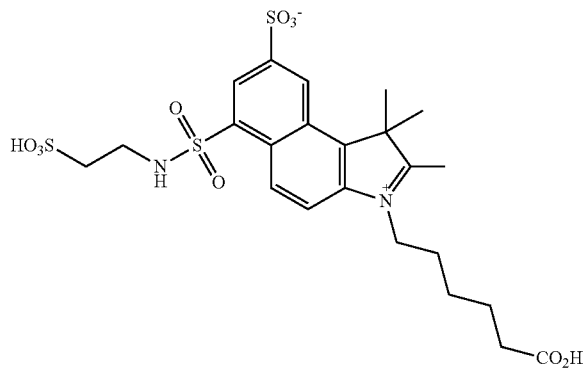

DS374-14

3.3 Synthesis of 3c'
3b (67 mg, 0.1 mmole) dissolved in 0.8 mL of sulfolane at 80° C. was added 6-bromohexanoic acid (196 mg, 1.0 mmole) with stirring. The reaction was heated to 120° C. for 3 hr. After cooling down the reaction was diluted with 10 mL 0.1 N TEAB, filtered, and purified by reverse phase HPLC eluted with a gradient of $CH_3CN$ over 0.1 N TEAB buffer. The yield of the product was 42 mg.
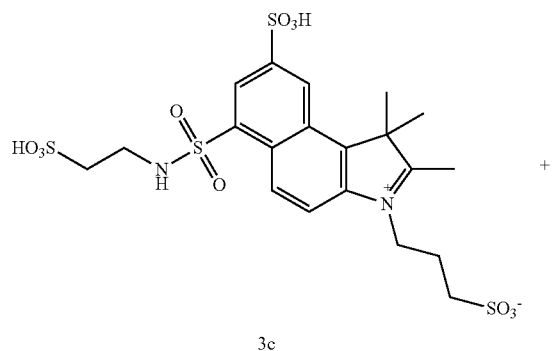
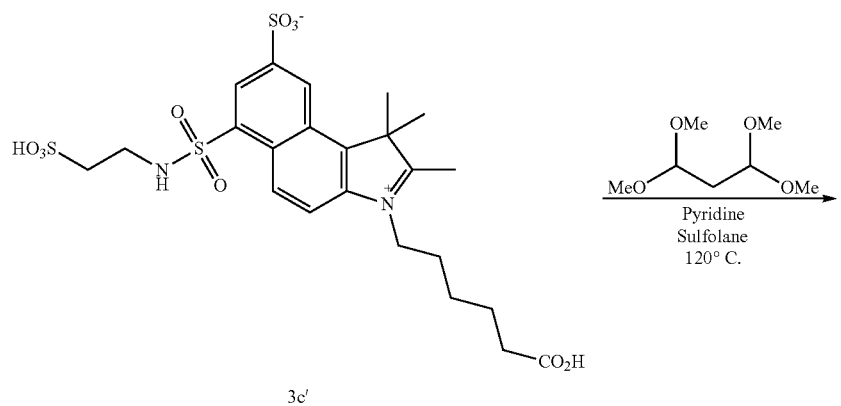
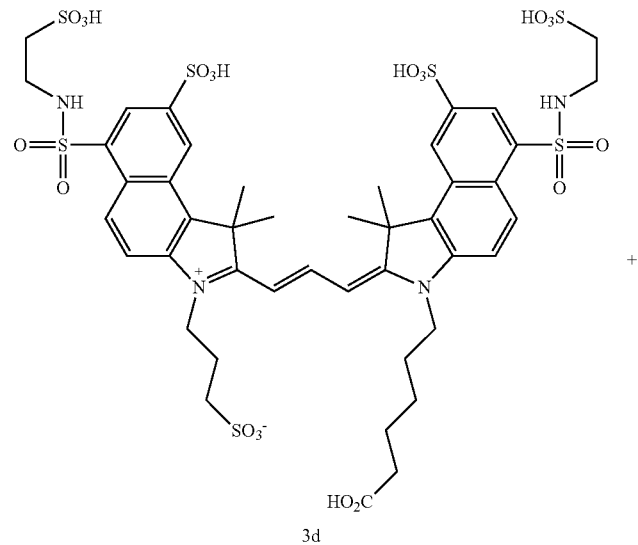

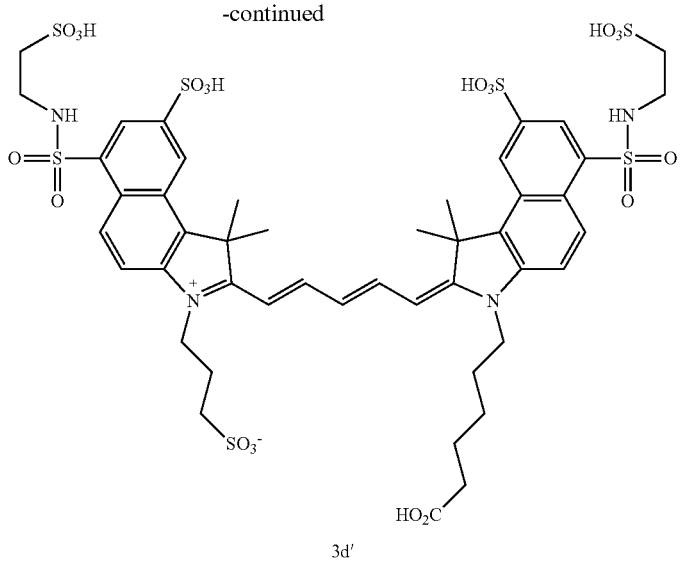

3d'

3.4 Synthesis of 3d and 3d'

3c (5 mg, 0.006 mmole) and 3c' (5 mg, 0.006 mmole) dissolved in 0.3 mL of sulfolane and 0.3 mL of pyridine at 80° C. was added 1,1,3,3 tetramethoxypropane (4.0 mg, 0.025 mmole) with stirring. The reaction was heated to 120° C. for 3 hr, during which time additional 1,1,3,3 tetramethoxypropane (8.2 mg, 0.05 mmole) was added to the reaction. After cooling down the reaction was diluted with 10 mL 0.1 N TEAB, filtered, and purified by reverse phase HPLC eluted with a gradient of CH+CN over 0.1 N TEAB buffer. The yield of the product (3d') was 1.7 mg. Also isolated from the reaction was 3d (2 2.4 mg).

3.5 Synthesis of 3e and 3e'

Similar to the synthesis of 3d and 3d'; starting from 3b", 3e and 3e' were prepared in 3 steps with similar yields.

3.6 Synthesis of 3f and 3f

Similar to the synthesis of 3d and 3d'; starting from 3b', 3f and 3f' were prepared in 3 steps with similar yields.

Example 4

Scheme 6: Synthesis of pyridyl benzindole cyanine dyes

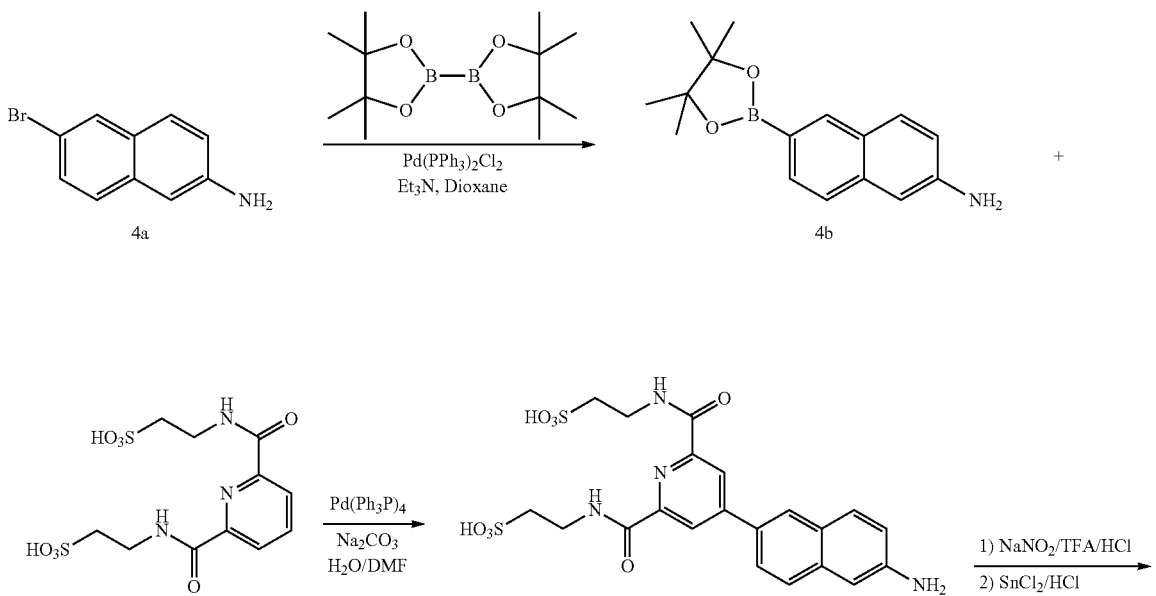

119
120
-continued
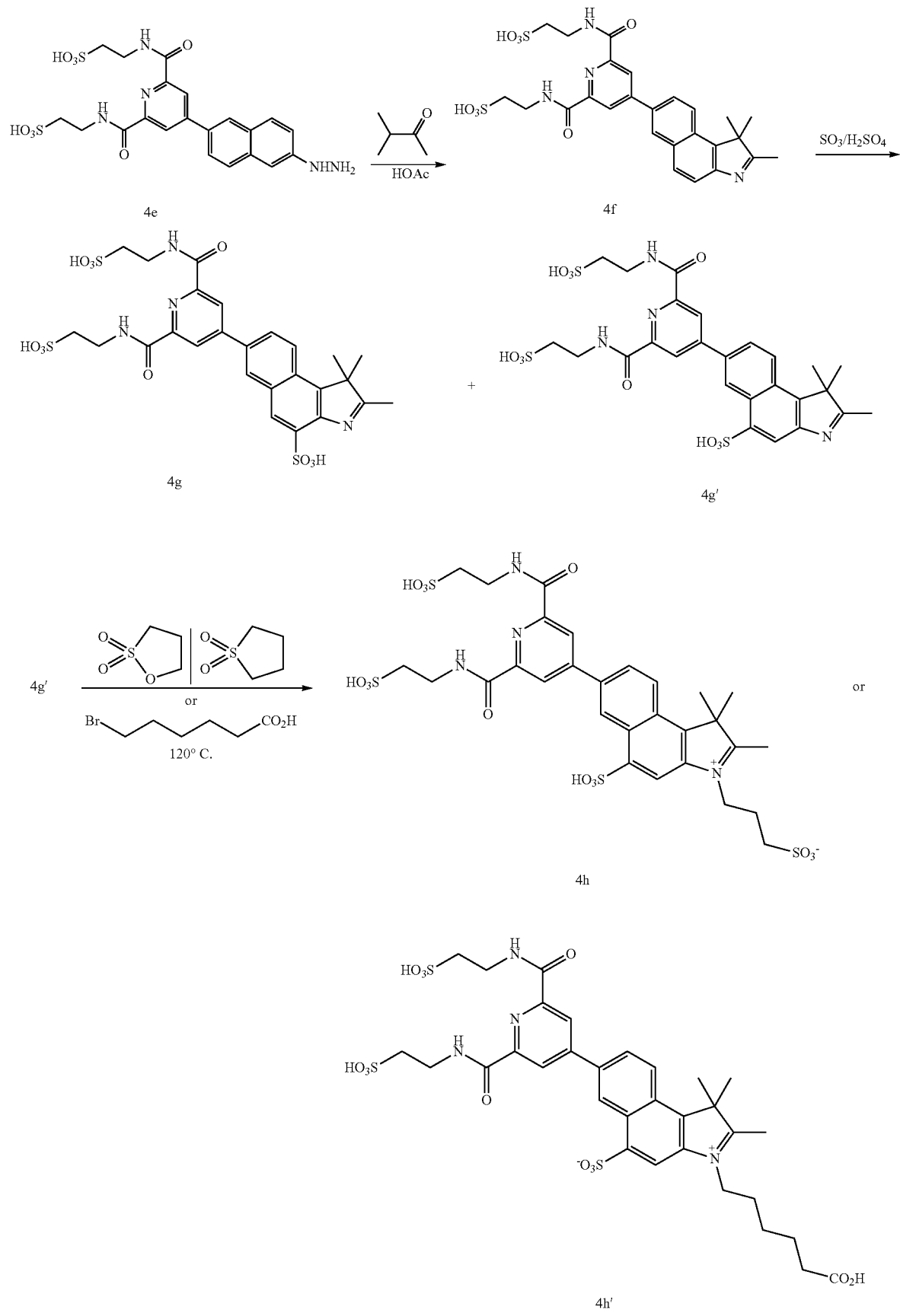

121 122
-continued
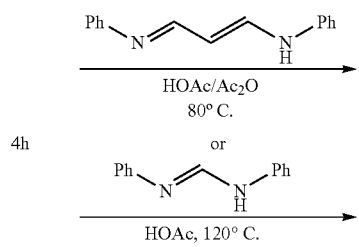
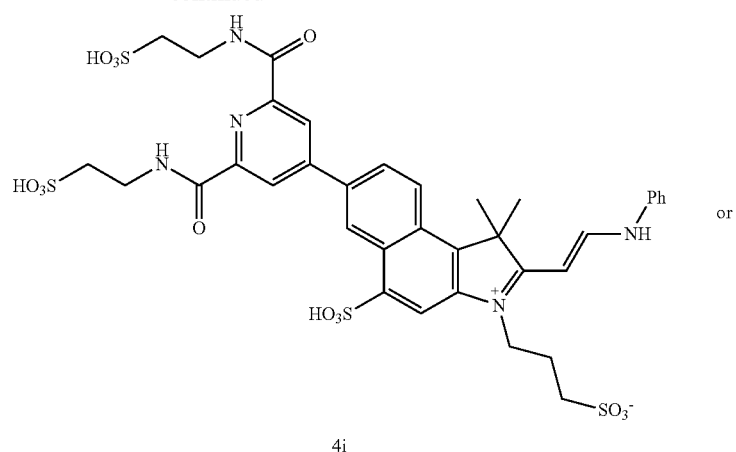
4i
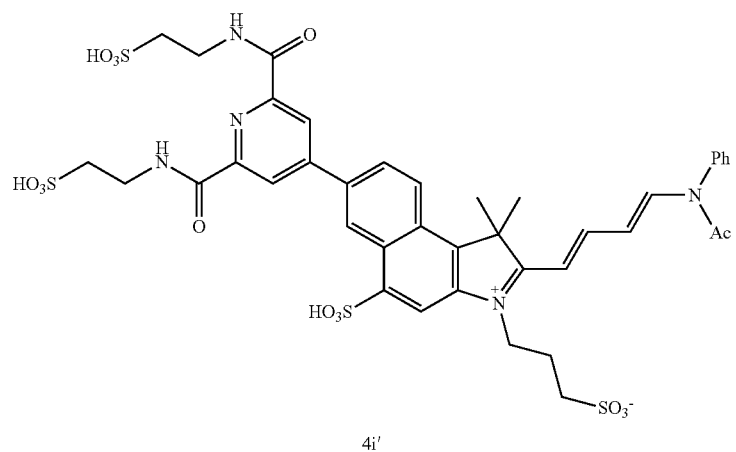
4i'
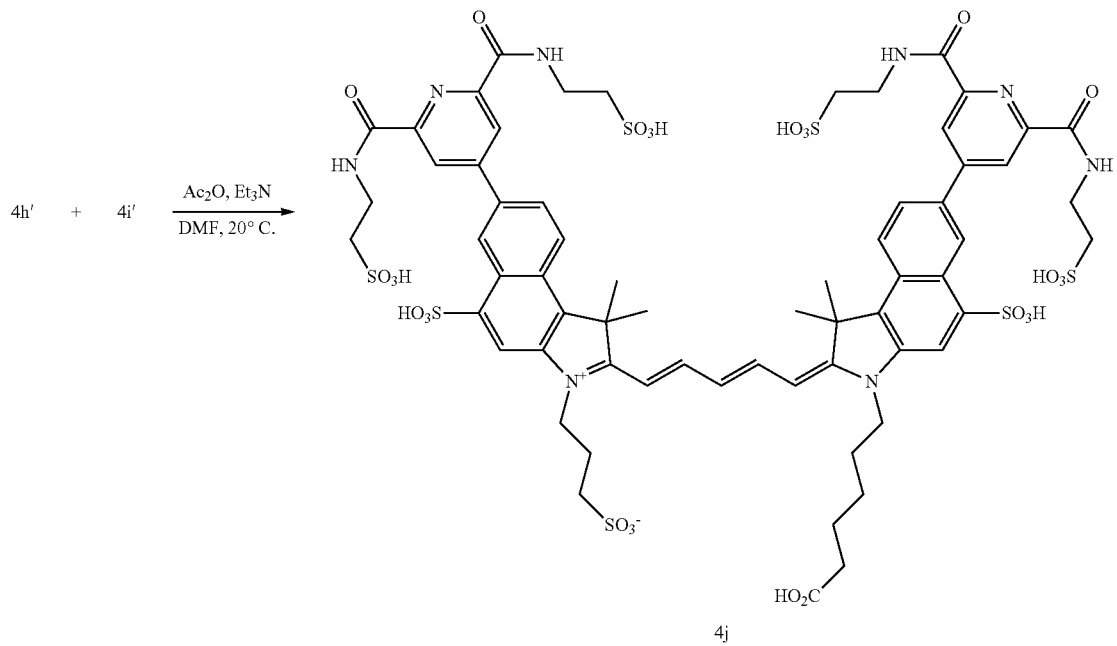
4j

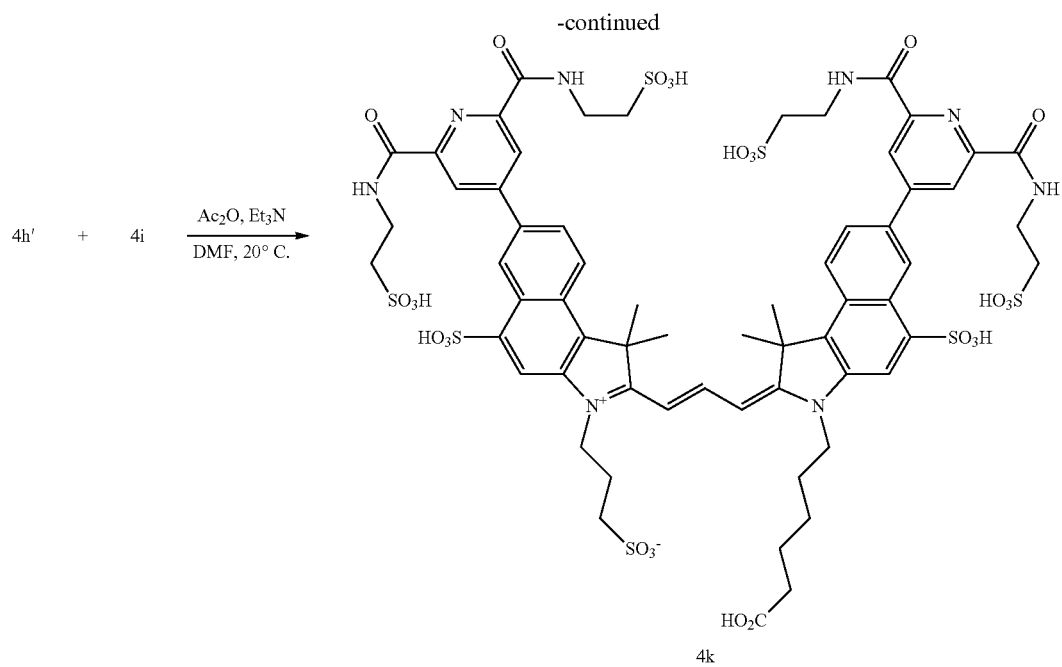

4k

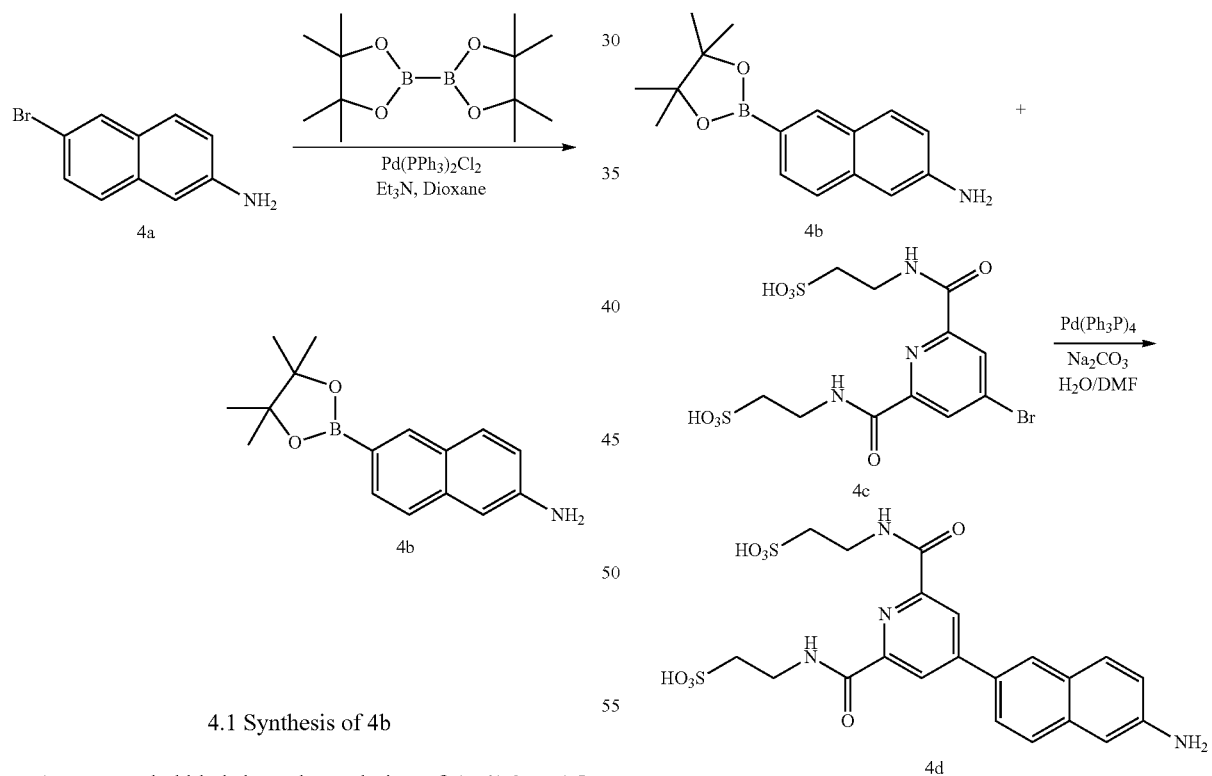

4.1 Synthesis of 4b

Argon was bubbled through a solution of 4a (1.0 g, 4.5 mmole), 4,4,5,5-tetramethyl-1,3,2-dioxaborolane (1.72 g, 13.5 mmole), and triethylamine (1.5 g, 14.6 mmole) in 10 mL of dioxane for 30 min, $Pd(PPh_3)_2Cl_2$ (160 mg, 0.23 mmole) was added to the mixture after bubbling for 15 min. The result mixture was heated at 80° C. for 8 hr under a slight positive pressure of argon. The solvents were removed in vacuo, the residue was dissolved in DCM and purified by silica gel flash column chromatography eluted with a gradient of MeOH over DCM. The yield of the desired product was 646 mg.

4.2 Synthesis of 4d

A solution of $Na_2CO_3$ (240 mg, 2.26 mmole) in 2.5 mL $H_2O$ was added dropwise to a solution of 4c (207 mg, 0.45 mmole) and 4b (115 mg, 0.45 mmole) in 5 mL of DMF with stirring. Argon was bubbled through the result mixture for 1 hr, $Pd(PPh_3)_4$ (17 mg, 0.015 mmole) was added to the mixture after bubbling for 30 min. The result mixture was heated at 100° C. for 6 hr under a slight positive pressure of argon. The solvents were removed in vacuo, the residue was redissolved in 10 mL 0.1 N TEAB buffer, filtered and purified by reverse phase HPLC eluted with a gradient of CH₃CN over 0.1 N TEAB buffer. The yield of the desired product was 147 mg.

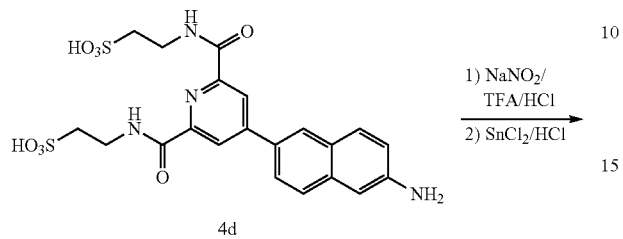

4d

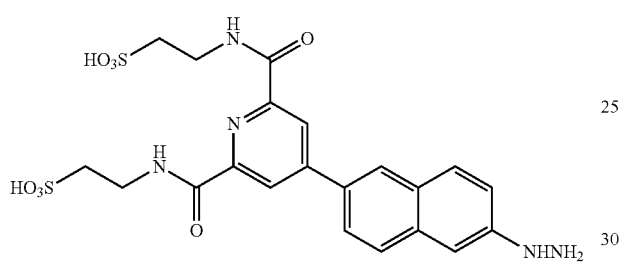

4e

4.3 Synthesis of 4e

A solution NaNO₂ (21 mg, 0.30 mmole) in 0.5 mL H₂O was added to a solution of 4d (147 mg, 0.20 mmole) in 6 mL trifluoroacetic acid and 1 mL 6 N HCl at −5~−10° C. over 2 min. During the course of addition the temperature was kept below −5° C. The reaction was stirred for another 30 min after the addition was completed. SnCl₂.2H₂O (145 mg, 0.64 mmole) in 0.5 mL 6N HCl, pre-cooled at −5° C., was added dropwise to the reaction at −5° C. over 2 min. The reaction was stirred for 4 hr as the cooling bath gradually warmed to room temperature. The reaction was diluted with 10 mL of H₂O, filtered, neutralized with 1 M NaOH to pH 9, and purified by reverse phase HPLC eluted with a gradient of CH₃CN over 0.1 N TEAB buffer. The yield of the product was 88 mg.

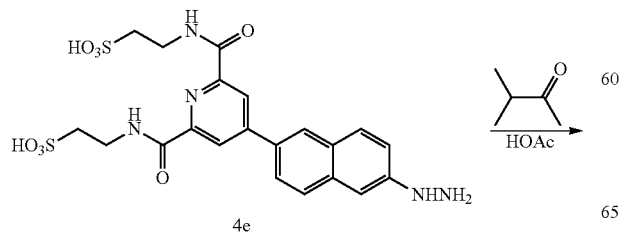

4e

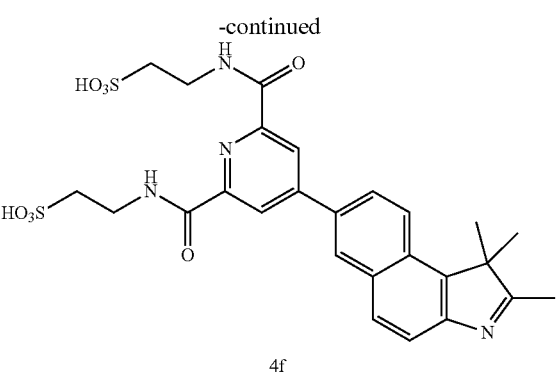

4f

4.4 Synthesis of 4f

A solution of 4e (88 mg, 0.12 mmole) and methyl isopropyl ketone (104 mg, 1.2 mmole) in 3 mL HOAc was heated at 100° C. for 3 hr. HOAc was removed in vacuo, the residue redissolved in 0.1 N TEAB, filtered, and purified by reverse phase HPLC eluted with a gradient of CH3CN over 0.1 N TEAB buffer. The yield of the product was 77 mg.

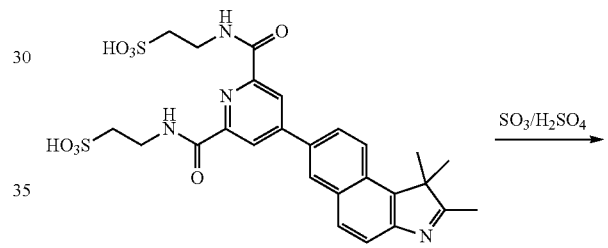

4f

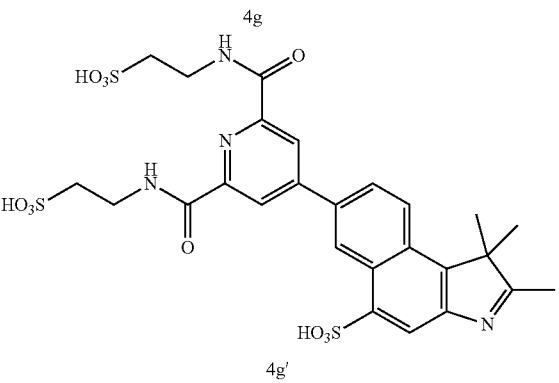

4g

4g′

4.5 Synthesis of 4g and 4g'

Fuming sulfuric acid (1 mL) was added to 4f (70 mg, 0.088 mmole) and the reaction stirred at room temperature for 1 hr. The reaction was quenched with 10 mL EtOAc pro-cooled at 4° C. The precipitate was collected by centrifugation redissolved in 0.1 N TEAB, filtered, and purified by reverse phase HPLC eluted with a gradient of CH₃CN over 0.1 N TEAB buffer. The yield of the product, 4g was 14 mg and 4g' was 45 mg.

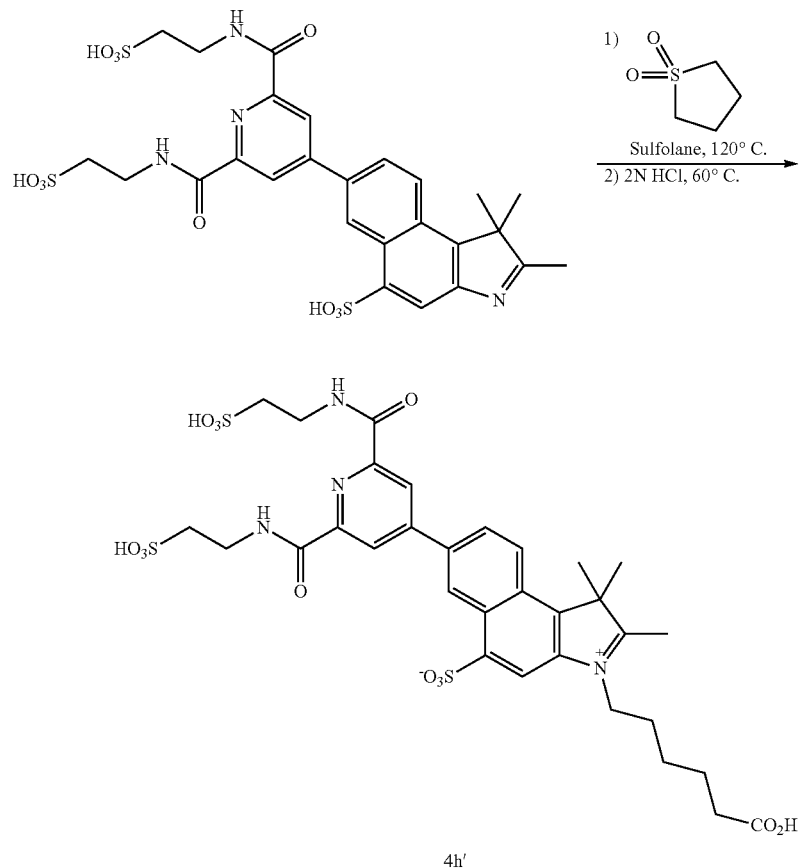

4.6 Synthesis of 4h'

4g' (21 mg, 0.021 mmole) dissolved in 0.5 mL of sulfolane at 80° C. was added 6-bromohexanoic acid (60 mg, 0.30 mmole) with stirring. The reaction was heated to 130° C. for 3 hr. After cooling down the reaction was diluted with 5 mL 0.1 N TEAB, filtered, and purified by reverse phase HPLC eluted with a gradient of CH₃CN over 0.1 N TEAB buffer. The yield of the product was 10.1 mg.

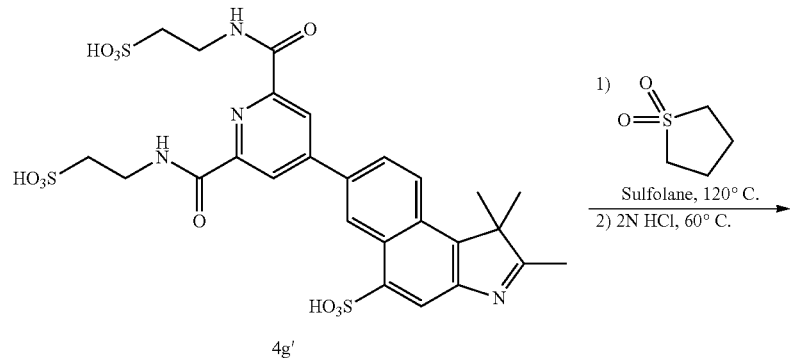

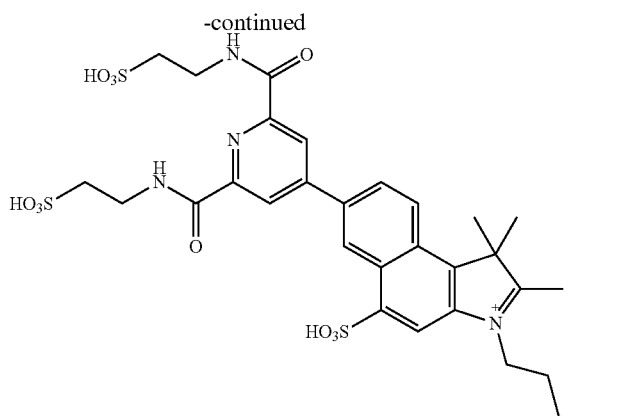

4h

4.7 Synthesis of 4h

4g' (24 mg, 0.034 mmole) dissolved in 0.5 mL of sulfolane at 80° C. was added 1,3 propanesultone (47 mg, 0.34 mmole) with stirring. The reaction was heated to 120° C. for 1 hr. After cooling down the reaction was diluted with 10 mL 0.1 N TEAB, filtered, and purified by reverse phase HPLC eluted with a gradient of CH3CN over 0.1 N TEAB buffer. The yield of the product was 17.3 mg.

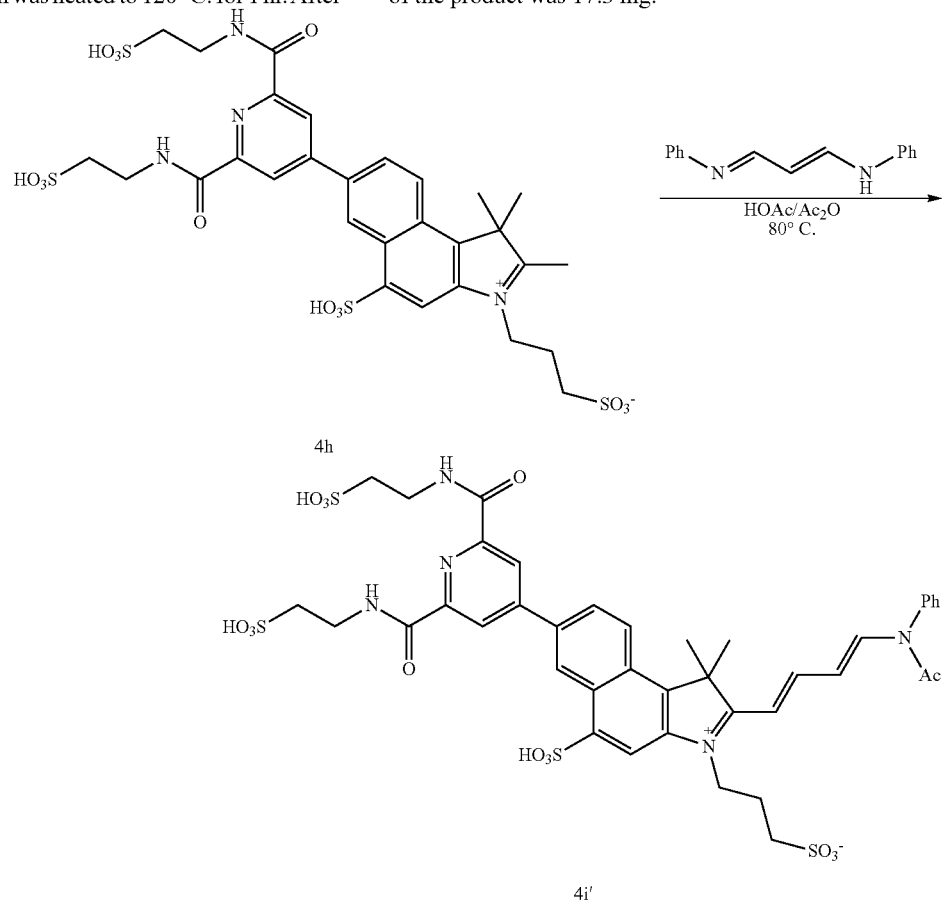

4.8 Synthesis of 4i'

4h (8.7 mg, 0.007 mmole) and 3-anilinoacrolein anil (6 mg, 0.023 mmole) was heated in 0.2 mL of HOAc and 0.2 mL of Ac$_2$O at 80° C. for 1 hr. After cooling down, the reaction was diluted with 4 mL of EtOAc, the precipitate was collected, washed with EtOAc, Et$_2$O, and dried under vacuum. The yield of the crude product was 11.4 mg and was used without further purification.

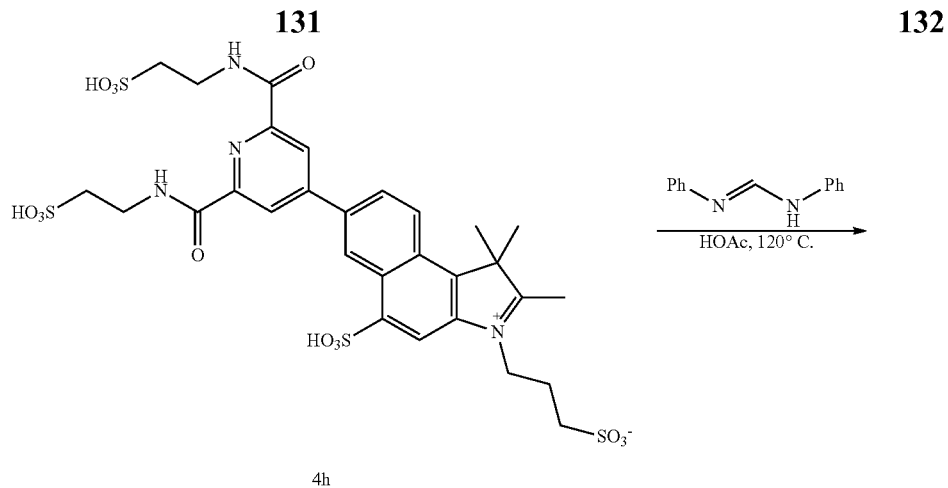

4h

4.9 Synthesis of 4i 4h (8.7 mg, 0.007 mmole) and diphenyl formamidine (4.7 mg, 0.023 mmole) was heated in 0.3 mL of HOAc at 120° C. for 6 hr. During which time more diphenyl formamidine (4.7 mg, 0.023 mmole) was added to the reaction. After cooling down, the reaction was diluted with 4 mL of EtOAc, the precipitate was collected, washed with EtOAc, Et$_2$O, and dried under vacuum. The yield of the crude product was 10.5 mg and was used without further purification.

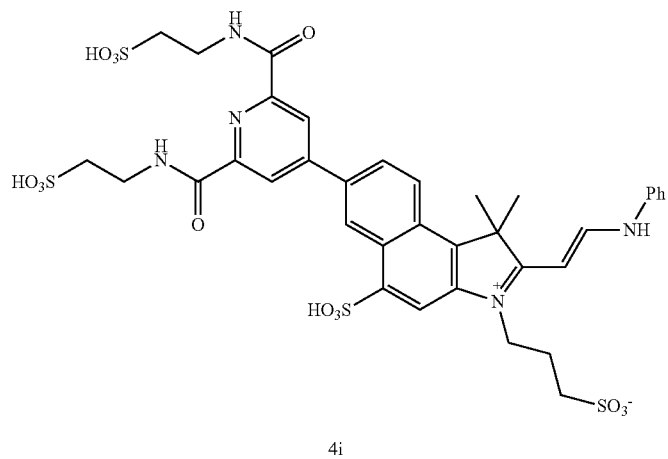

4i

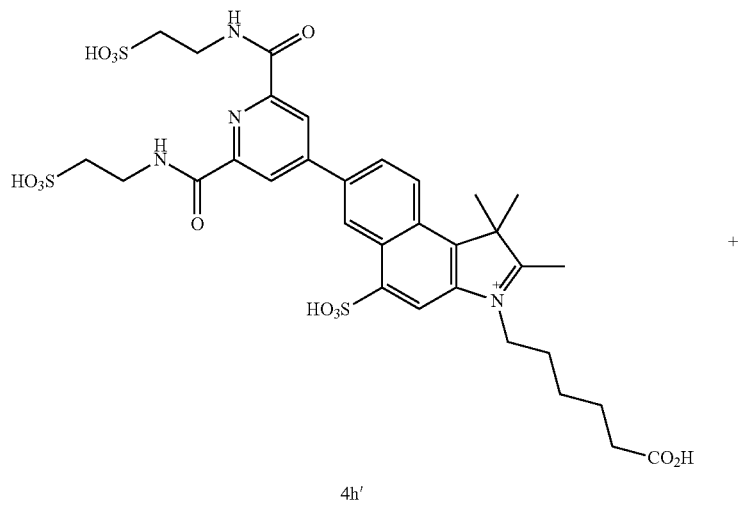

4h'

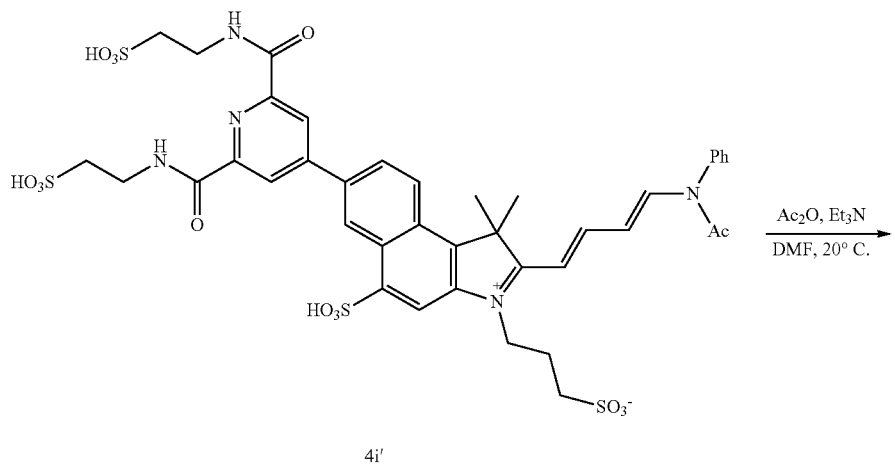

4i′

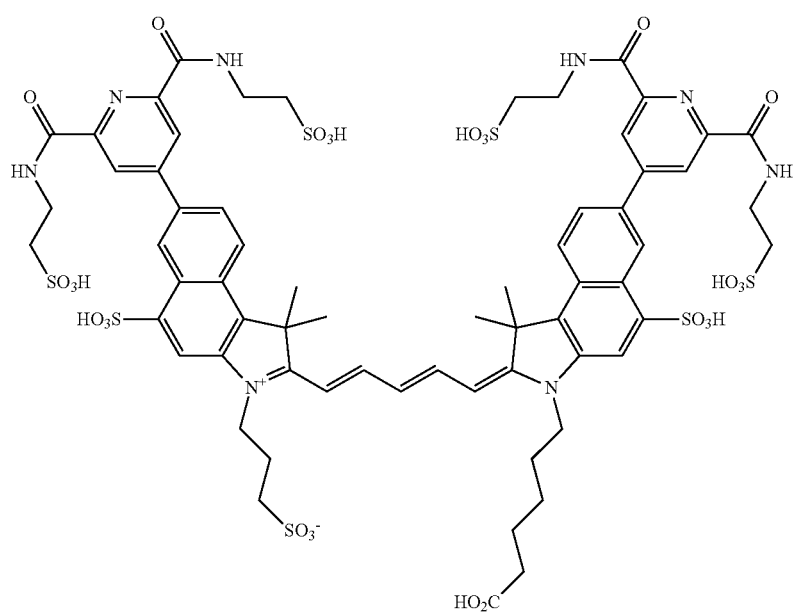

4j

4.10 Synthesis of 4j

To a stirring solution of 4h′ (3.3 mg, 2.8 umole) and 4i′ (11.4 mg, crude) in 0.2 mL of DMF was added $Et_3N$ (10 mg, 0.1 mmole) followed by $Ac_2O$ (10 mg, 0.1 mmole). The reaction was stirred at room temperature for 3 hr and diluted with 5 mL 0.1 N TEAB buffer. The solution was filtered and the product purified by reverse phase HPLC eluted with a gradient of $CH_3CN$ over 0.1 N TEAB buffer. The product was further purified by ion exchange column eluted with a gradient of 1.5 N TEAB buffer with 20% ACN over 0.05 N TEAB buffer with 20% ACN. The yield of the product was 1.6 mg.

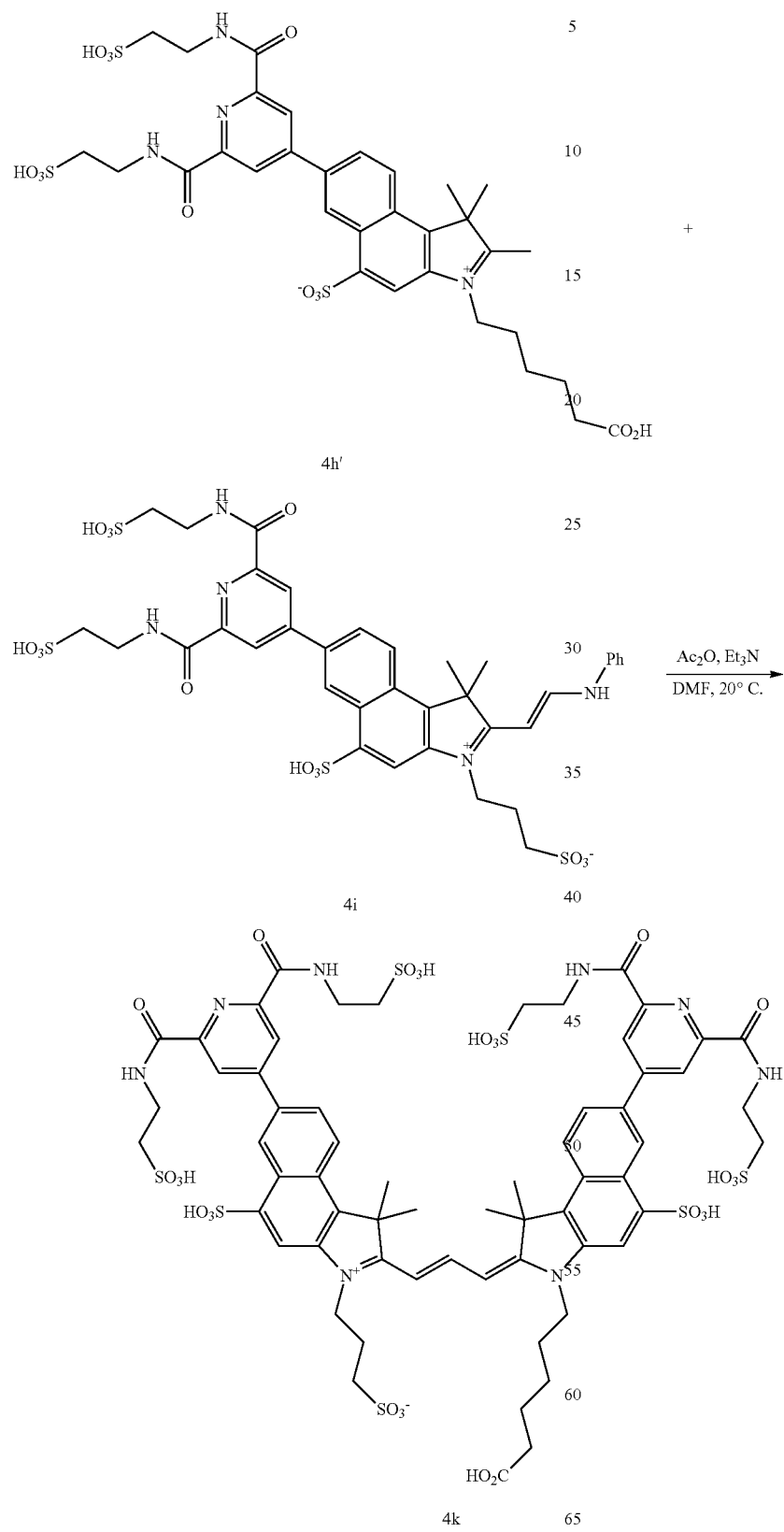

4.11 Synthesis of 4k

To a stirring solution of 4h' (3.3 mg, 2.8 umole) and 4i (10.5 mg, crude) in 0.2 mL of DMF was added Et₃N (10 mg, 0.1 mmole) followed by Ac₂O (10 mg, 0.1 mmole). The reaction was stirred at room temperature for 3 hr and diluted with 5 mL 0.1 N TEAB buffer. The solution was filtered and the product purified by reverse phase HPLC eluted with a gradient of CH₃CN over 0.1 N TEAB buffer. The product was further purified by ion exchange column eluted with a gradient of 1.5 N TEAB buffer with 20% ACN over 0.05 N TEAB buffer with 20% ACN. The yield of the product was 1.0 mg.

Example 5

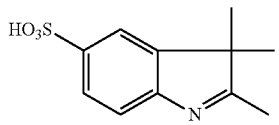

2,3,3,-Trimethylindoleninium-5-sulfonate

To an oven dried 500-mL round bottomed flask equipped with a stirring bar, a reflux condenser and a nitrogen balloon was add p-hydrazinobenzenesulfonic acid hemihydrate (50.0 g, 0.253 mol), acetic acid (150 mL), and 3-methyl-2-butanone (84 mL, 0.785 mol). Heated the reaction mixture with stirring in an oil bath at 115° C. for 4 h. Monitored the reaction with TLC (2:1 CH₂Cl₂:MeOH; starting material $R_f$=0.42, product $R_f$=0.69) until all starting material was consumed. Removed oil bath and cooled the reaction solution to ambient temperature. Slowly added EtOAc (~200 mL) and the resultant pink solid were collected via filtration with the aid of EtOAc (2×50 mL). After brief drying the solid was dissolved in MeOH (700 mL). Added KOH (15 g) in iPrOH (200 mL) to the above solution and stirred. Collected the resultant yellow solid via filtration. Washed the solid with iPrOH (2×100 mL), EtOAc (3×100 mL) and air dried. Placed the solid in two amber bottles and dried in a desiccator under high vacuum overnight. There was obtained 48.8 g (69.5%) of the desired product as a potassium salt.

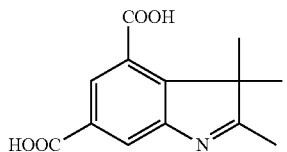 [SMILES: CC1=Nc2cc(C(=O)O)cc(C(=O)O)c2C1(C)C]

2,3,3-Trimethyl-4,6-dicarboxy-3H-indole

A solution of 5-hydrazinylbenzene-1,3-dicarboxylic acid (30.0 g, 129 mmol), isopropylmethylketone (22.0 mL, 205 mmol) in acetic acid (300 mL) and was heated under reflux in an oil bath for 18 h. After cooling to ambient temperature the solvent was evaporated off under reduced pressure to a small volume of ~100 mL. To the crude mixture was added iPrOH (200 mL) and the solid was collected with a filter funnel, washed with EtOAc (3×200 mL) and ethyl ether (2×200 mL) and dried. Further drying of the solid in an oven at 50° C. under high vacuum for 18 h provided 30.44 g (95.5%) of the product.

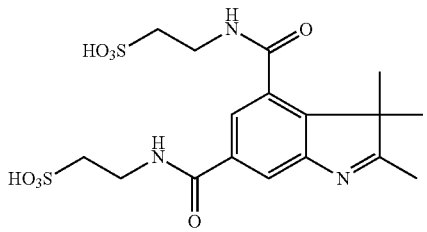 [SMILES: CC1=Nc2cc(C(=O)NCCS(=O)(=O)O)cc(C(=O)NCCS(=O)(=O)O)c2C1(C)C]

2,3,3-Trimethyl-4,6-di(sulfoethylcarboxyamide)-3H-indole

To a solution of 2,3,3-trimethyl-4,6-dicarboxy-3H-indole (71 mg, 0.29 mmol) in DMF (3.5 mL) was added triethylamine (0.21 mL) followed by N,N,N',N'-tetramethyl-O—(N-succinimidyl)uronium tetrafluoroborate (0.26 g, 0.86 mmol). The resulting mixture was stirred at room temperature for 15 minutes to generate the bis-N-succinimidyl ester. In a separate flask, a solution of taurine was prepared by dissolving 0.35 g of taurine in 3.5 mL of 1 M NaHCO₃. The bis-N-succinimidyl ester solution was added in a rapid dropwise fashion into this aqueous taurine solution and after two hours of stirring at room temperature, all the volatile components were removed under reduced pressure and the residual was stirred in 10 mL of water, filtered to remove any insoluble material and the crude was purified on a RP C-18 column to yield 80 mg of product as its triethylammonium salt.

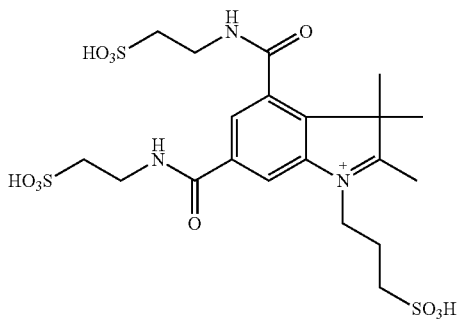

1-(3-Sulfopropyl)-2,3,3-trimethylindoleninium-4,6-di(sulfoethylcarboxyamide)

To a solution of 2,3,3-trimethyl-4,6-di(sulfoethylcarboxyamide)-3H-indole (267 mg, 0.40 mmole) sulfolane (1 mL) was added 1,3-propanesultone (492 mg, 4 mmole) with stirring. The reaction was heated to 120° C. for 1.5 h. After cooling to ambient temperature the solution was diluted with 0.1 N TEAB (10 mL), filtered, and purified purified by reverse-phase HPLC (acetonitrile/0.1 M TEAB gradient) to give 220 mg of product.

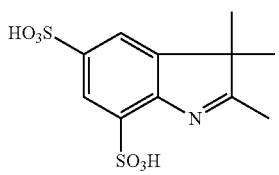

-continued

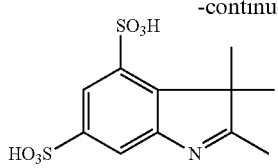

2,3,3,-Trimethylindoleninium-5,7-disulfonate and 2,3,3,-Trimethylindoleninium-4,6-disulfonate To a solution of 2,3,3-trimethylindoleninium (2.00 mL, 12.5 mmol) was added oleum (30%, 11 mL, 62.3 mmol) and stirred at ambient temperature for 48 h followed by heating to 160° C. for 18 h. After cooling to ambient temperature the acid was poured into ice water (50 mL) and neutralized with KOH to basic. The aqueous solvent was evaporated off under reduced pressure to give a solid, which was then extracted with MeOH (3×100 mL). After filtering through a pad of filter paper the organic extracts were combined and concentrated to dryness. Triturated the solid with iPrOH 950 mL) and the solid was collected through filtration, washed with EtOAc (3×20 mL) and dried. Further drying in an oven at 45° C. under high vacuum gave a mixture of the titled compound (~6:4) as an off-white solid (quantitative yield).

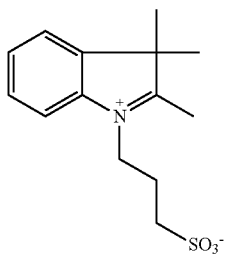

1-(3-Sulfonatopropyl)-2,3,3-trimethylindoleninium

To an oven dried 50-mL round bottom flask equipped with a stir bar, condenser, and an argon balloon in an oil bath was added 2,3,3-trimethylindolenine (1.60 mL, 10.0 mmol), 1,3-propanesultone (1.32 mL, 15.0 mmol) and 1,2-dichlorobenzene (20 mL). Heated the oil bath to 140° C. for 18 h. Removed the oil bath and cooled the mixture to ambient temperature. Decanted the solvent and triturated the solid with EtOAc (40 mL). Collected the solid using filtration funnel. Re-dissolved the solid in hot MeOH (20 mL) and concentrated to dryness to give the solid product. Further drying in an oven at 45° C. under high vacuum overnight gave 1.96 g (70.0%) of product.

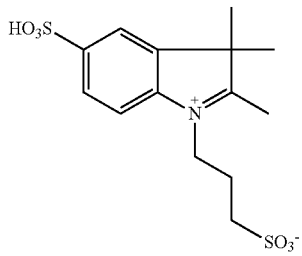

1-(3-Sulfonatopropyl)-2,3,3-trimethylindoleninium-5-sulfonate

To an oven dried 50-mL round bottom flask equipped with a stir bar, condenser, and an argon balloon in an oil bath was added 2,3,3-trimethylindoleninium-5-sulfonate (1.50 g, 5.40 mmol), 1,3-propanesultone (0.62 mL, 7.0 mmol) and 1,2-dichlorobenzene (15 mL). Heated the oil bath to 140° C. for 48 h. The progress of the reaction was monitored with analytical HPLC for the disappearance of the starting material, and the formation of the product. Removed oil bath and cooled the mixture to ambient temperature. Decanted the solvent and triturated the solid with EtOAc (40 mL). Collected the solid using filtration funnel. Re-dissolved the solid in hot MeOH (40 mL) and added iPrOH (200 mL) to precipitate the solid. The resultant solid was collected, washed with iPrOH (2×50 mL), EtOAc (2×50 mL), ether (2×50 mL) and air dried. The solid was placed in an amber bottle and dried in an oven under high vacuum overnight. There was obtained a total of 1.28 g (59.2%) of product.

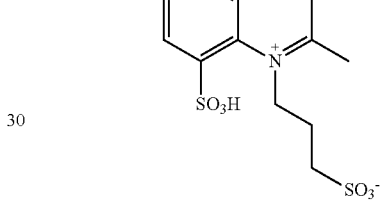

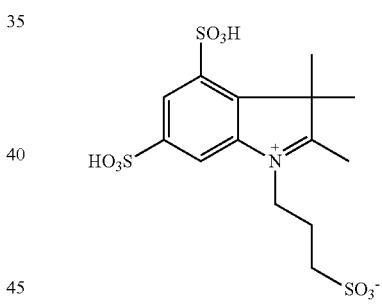

1-(3-Sulfonatopropyl)-2,3,3-trimethylindoleninium-5,7-disulfonate and 1-(3-Sulfonatopropyl)-2,3,3-trimethylindoleninium-4,6-disulfonate To a 6:4 mixture of 2,3,3,-trimethylindoleninium-5,7-disulfonate and 2,3,3,-trimethylindoleninium-4,6-disulfonate (803.2 mg, 2.515 mmol) was added 1,3-propanesultone (1.99 mL, 22.6 mmol) in a seal vial. Heated the vial in an oil bath at 140° C. for 72 h. After cooling to ambient temperature added ethyl acetate (20 mL) to triturate the solid. Decanted the organic solvent and continue to triturate the solid with EtOAc (3×20 mL). Collected the solid using filtration funnel. Re-dissolved the solid in hot MeOH (40 mL) and added iPrOH (200 mL) to precipitate the solid. The resultant solid was collected, washed with iPrOH (2×50 mL), EtOAc (2×50 mL), ether (2×50 mL) and air dried. The solid was placed in an amber bottle and dried in an oven under high vacuum overnight. There was obtained 660 mg (60%) of product.

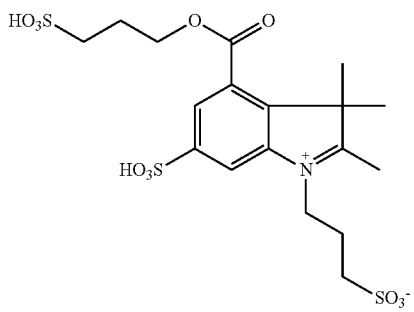

1-(3-Sulfonatopropyl)-2,3,3-trimethylindoleninium-4-(sulfonatopropylcarboxylate)-6-sulfonate A mixture of 2,3,3-trimethylindoleninium-4-carboxy-6-sulfonate (218 mg, 0.769 mmol) and 1,3-propanesultone (1.5 mL, 17 mmol) in a sealed tube was heated to 140° C. for 60 h. Cooled the mixture to ambient temperature and to it was added ethyl acetate (20 mL), stirred and the organic solvent was decanted. Repeated the process two more times with ethyl acetate (2×20 mL) and the oily product was dried under reduced pressure. Added 1 M HCl (15 mL) to the tube and heated to 80° C. for 4 h. After cooling to ambient temperature the solvent was evaporated off under reduced pressure. The crude product was then purified by reverse-phase HPLC (acetonitrile/0.1 M TEAB gradient) to give 263.2 mg of the solid product (64.8% yield).

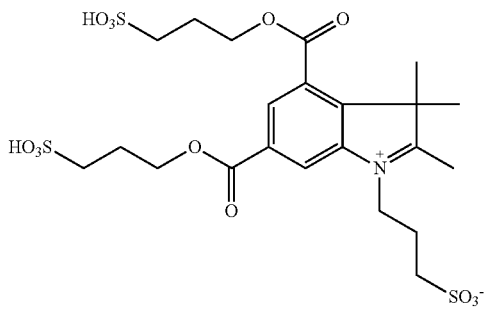

1-(3-Sulfonatopropyl)-2,3,3-trimethylindoleninium-4,6-di(sulfonatopropylcarboxylate)

A mixture of 2,3,3-trimethyl-4,6-dicarboxy-3H-indole (600 mg, 2.43 mmol), 1,3-propanesultone (5 mL, 57 mmol) and sofolane (3 mL) in a sealed tube was heated to 125° C. for 36 h. Cooled the mixture to ambient temperature and to it was added ethyl acetate (20 mL), stirred and the organic solvent was decanted. Repeated the process two more times with ethyl acetate (2×20 mL) and the oily product was dried under reduced pressure. Added 1 M HCl (10 mL) to the tube and heated to 60° C. for 10 h. After cooling to ambient temperature the solvent was evaporated off under reduced pressure. The crude product was then purified by reverse-phase HPLC (acetonitrile/0.1 M TEAB gradient) to give 283 mg (18%) of the solid product and 605 mg (51% yield) of a monoacid ester, presumably the 4-carboxy derivative.

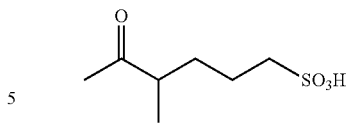

4-Methyl-5-oxo-1-hexanesulfonate

To a solution of ethyl 2-methylacetoacetate (30.0 mL, 208 mmol) was added 1M t-BuOK in t-BuOH (229 mL, 229 mmol) and 1,3-propanesultone (20.2 mL, 229 mmol) and heated in an oil bath to reflux for 24 h. After cooling to ambient temperature a solid was formed which was triturated with EtOAc (200 mL) and the resultant solid was collected through filtration, washed with ethyl acetate (2×20 mL) and dried. To the dried solid was added 50% HCl (100 mL) and the solution was heated at 110° C. for 24 h. Solvent was evaporated off under reduced pressure and co-evaporated with acetonitrile (2×30 mL) to give 38.3 g (95%) of an oily product. The crude residue was used without further purification.

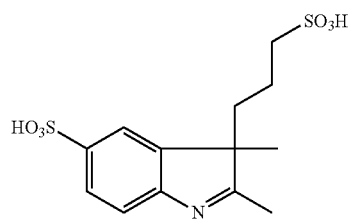 [SMILES: CC1=Nc2ccc(S(=O)(=O)O)cc2C1(C)CCCS(=O)(=O)O]

2,3-Dimethyl-3-(3-sulfopropyl)indoleninium-5-sulfonate

To an oven dried 100-mL round bottomed flask equipped with a stirring bar, a reflux condenser and a nitrogen balloon was add p-hydrazinobenzenesulfonic acid hemihydrate (2.0 g, 0.010 mol), acetic acid (25 mL), and 4-methyl-5-oxo-1-hexanesulfonate (5.5 g, 0.028 mol). Heated the reaction mixture to reflux with stirring in an oil bath at 115° C. for 30 h. Removed the oil bath and cooled the reaction solution to ambient temperature. Solvent was evaporated off under reduced pressure to dryness. The residual crude product was triturated with MeOH/iPrOH (1:5, 100 mL) and filtered. The solid was then dissolved in MeOH (400 mL) and filtered to remove the undissolved solid (starting material). The filtrate was poured into a beaker and to it was added KOH (1.19 g, 0.021 mol) in iPrOH (400 mL) and stirred. The resultant solid was collected, washed with iPrOH (2×20 mL), EtOAc (2×20 mL) and dried. Placed the solid in an amber bottle and dried in an oven at 50° C. under high vacuum for 18 h. There was obtained 2.94 g (68.4%) of the desired product as a potassium salt.

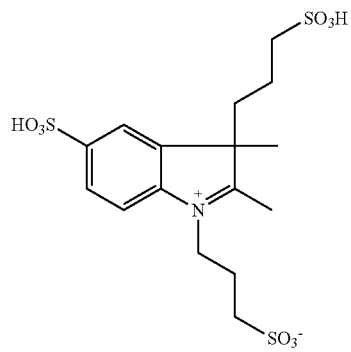

2,3-Dimethyl-1,3-bis(3-sulfopropyl)indoleninium-5-sulfonate

To an oven dried 50-mL round bottom flask equipped with a stir bar, condenser, and an argon balloon in an oil bath was added 2,3-dimethyl-3-(3-sulfopropyl)indoleninium-5-sulfonate (530 mg, 1.25 mmol), 1,3-propanesultone (0.554 mL, 626 mmol) and 1,2-dichlorobenzene (5 mL). Heated the oil bath to 135° C. for 24 h. Removed oil bath and cooled the mixture to ambient temperature. Decanted the solvent and triturated the solid with iPrOH (40 mL). The resultant solid was collected, washed with iPrOH (2×50 mL), EtOAc (2×50 mL), ether (2×50 mL) and air dried. The solid was placed in an amber bottle and dried in an oven under high vacuum overnight. The solid product was used without further purification.

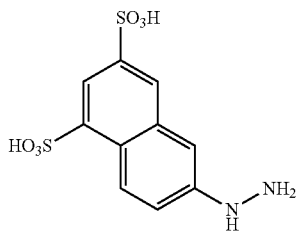 [SMILES: NNc1ccc2c(S(=O)(=O)O)cc(S(=O)(=O)O)cc2c1]

6-Hydrazino-1,3-naphthalenedisulfonate

To a solution of disodium 6-amino-1,3-naphthalenedisulfonate hydrate (10.0 g, 28.8 mmol) in 50% hydrochloric acid (200 mL) at 0° C. was added dropwise a cold solution of sodium nitroxide (2.18 g, 31.7 mmol) in water (20 mL). After completion of addition (~25 min) the solution was stirred for an additional 30 min at 0° C. followed by dropwise addition of a cold solution of SnCl$_2$ (6.0 g, 31.7 mmol) in hydrochloric acid (10 mL) in 40 min. Continue to stir at 0° C. for 1 h and then ambient temperature for 1 h. Concentrated to dryness and triturated with hot iPrOH (400 mL). Filtered to collect the solid, washed with iPrOH (2×30 mL), ethyl acetate (2×30 mL) and dried. Further drying in an oven at 40° C. under high vacuum for 18 h provided 12.4 g of a solid product (quantitative yield).

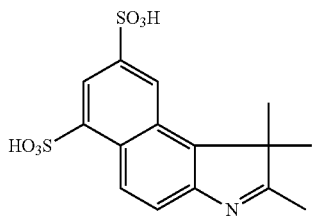 [SMILES: CC1=Nc2ccc3c(S(=O)(=O)O)cc(S(=O)(=O)O)cc3c2C1(C)C]

1,1,2-Trimethylbenz[e]indole-6,8-disulfonate

A solution of 6-hydrazino-1,3-naphthalenedisulfonate (10.3 g, 32.5 mmol), isopropylmethylketone (7.6 mL, 71 mmol), potassium acetate (6.82 g, 69 mmol) in acetic acid (50 mL) was heated under reflux in an oil bath for 24 h. After cooling to ambient temperature the solvent was evaporated off under reduced pressure to dryness and triturated with iPrOH (100 mL). The resultant solid was collected, washed with iPrOH (2×30 mL) and dried. Further drying in an oven at 40° C. under high vacuum for 18 h provided the solid product (9.59 g, 80%).

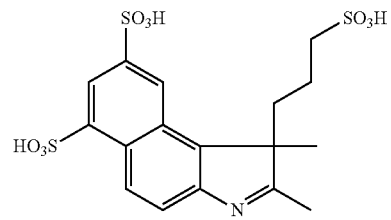 [SMILES: CC1=Nc2ccc3c(S(=O)(=O)O)cc(S(=O)(=O)O)cc3c2C1(C)CCCS(=O)(=O)O]

1,2-Dimethyl-1-(3-sulfopropyl)benz[e]indole-6,8-disulfonate

To an oven dried 100-mL round bottomed flask equipped with a stirring bar, a reflux condenser and a nitrogen balloon was add 6-hydrazino-1,3-naphthalenedisulfonate (3.18 g, 0.010 mol), acetic acid (35 mL), and 4-methyl-5-oxo-1-hexanesulfonate (5.5 g, 0.028 mol). Heated the reaction mixture to reflux with stirring in an oil bath at 115° C. for 30 h. Removed the oil bath and cooled the reaction solution to ambient temperature. Solvent was evaporated off under reduced pressure to dryness. The residual crude product was triturated with MeOH/iPrOH (1:5, 100 mL) and filtered. The solid was then dissolved in MeOH (400 mL) and filtered to remove the undissolved solid (starting material). The filtrate was poured into a beaker and to it was added KOH (1.19 g, 0.021 mol) in iPrOH (400 mL) and stirred. The resultant solid was collected, washed with iPrOH (2×20 mL), EtOAc (2×20 mL) and dried. Placed the solid in an amber bottle and dried in an oven at 50° C. under high vacuum for 18 h. There was obtained 4.3 g (90%) of the desired product as a potassium salt.

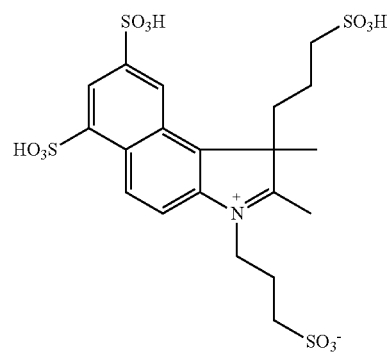

1,2-Dimethyl-1,3-bis(3-sulfopropyl)benz[e]indole-6,8-disulfonate

To an oven dried 50-mL round bottom flask equipped with a stir bar, condenser, and an argon balloon in an oil bath was added 1,2-dimethyl-1-(3-sulfopropyl)benz[e]indole-6,8-disulfonate (1.33 g, 2.25 mmol), 1,3-propanesultone (1.0 mL, 11.3 mmol) and 1,2-dichlorobenzene (10 mL). Heated the oil bath to 140° C. for 72 h. Removed the oil bath and cooled the mixture to ambient temperature. Decanted the solvent and triturated the solid with iPrOH (40 mL). The resultant solid was collected, washed with iPrOH (2×50 mL), EtOAc (2×50 mL), ether (2×50 mL) and air dried. Further drying in an oven under high vacuum overnight gave the solid product. The solid product was used without further purification.

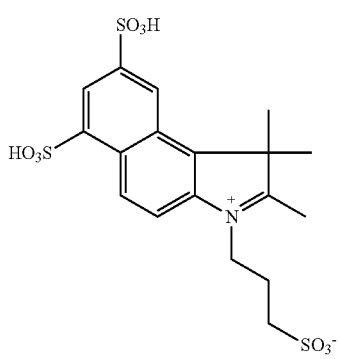

1,1,2-Trimethyl-3-(3-sulfopropyl)benz[e]indolium-6,8-disulfonate

A suspension of 1,1,2-trimethylbenz[e]indole-6,8-disulfonate (2.5 g, 6.8 mmol) and 1,3-propanesultone (2.16 mL, 24.4 mmol) in 1,2-dichlorobenzene (50 mL) was heated in an oil bath at 140° C. for 24 h. After cooling to ambient temperature the solvent was decanted, the solid was washed with ethyl acetate (3×20 mL) and solvent was decanted. The solid was triturated with methanol (50 mL) and then ethyl acetate (50 mL) was added. Filtered to collect the solid, washed with ethyl acetate (2×20 mL), ether (2×20 mL) and dried in an oven at 40° C. under high vacuum for 18 h to afford 1.9 g (50%) of a solid product.

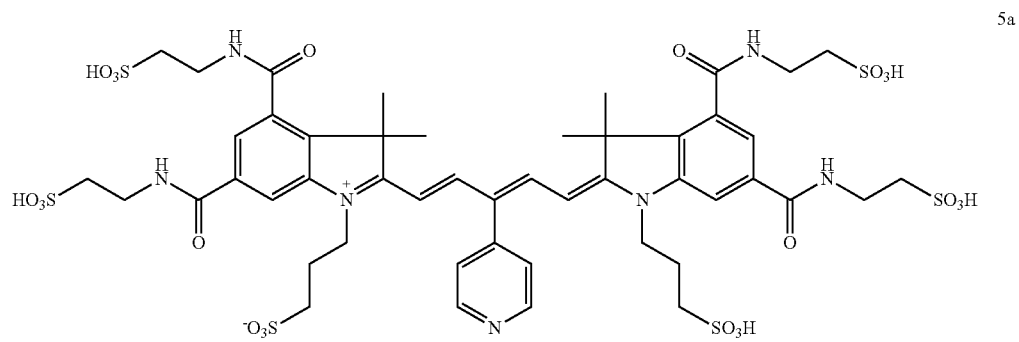

5a

Preparation of 5a

A solution of 1-(3-sulfopropyl)-2,3,3-trimethylindoleninium-4,6-di(sulfoethylcarboxyamide) (22.8 mg, 39 umol), 2-(3-pyridyl)malondialdehyde (3.00 mg, 20 umol), potassium acetate (3 mg, 30 umol) in acetic anhydride (0.5 mL) and acetic acid (0.5 mL) was heated at 130° C. for 3 h under nitrogen atmosphere. After cooling to ambient temperature the solvent was evaporated off under reduced pressure to give a dark blue solid, which was then subjected to reverse-phase HPLC (acetonitrile/0.1 M TEAB gradient) purification to give the product: 5a (4.66 umol, 24% yield, ☐max 640 nm).

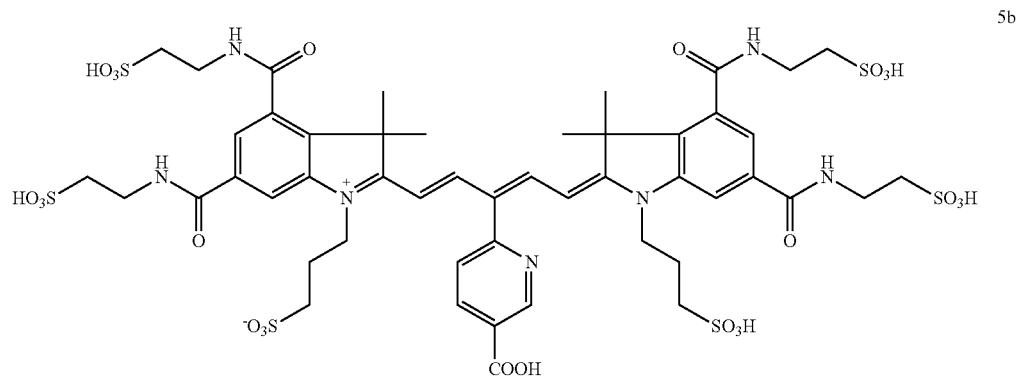

5b

Preparation of 5b

A solution of 1-(3-sulfopropyl)-2,3,3-trimethylindoleninium-4,6-di(sulfoethylcarboxyamide) (5.3 mg, 9 umol), 2-(3-hydroxycarbonyl-6-pyridyl)malondialdehyde (2.00 mg, 10 umol), potassium acetate (2 mg, 20 umol) in acetic anhydride (0.3 mL) and acetic acid (0.3 mL) was heated at 130° C. for 3 h under nitrogen atmosphere. After cooling to ambient temperature the solvent was evaporated off under reduced pressure to give a dark blue solid, which was then subjected to reverse-phase HPLC (acetonitrile/0.1 M TEAB gradient) purification to give the product: 5b (0.69 umol, 15% yield, □max 638 nm).

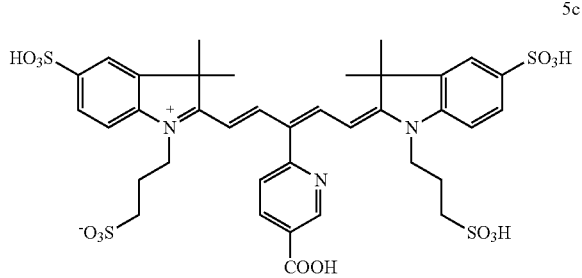

5c

Preparation of 5c

A solution of 2,3-dimethyl-1,3-bis(3-sulfopropyl)indoleninium-5-sulfonate (16.0 mg, 0.0400 mmol), 2-(3-hydroxycarbonyl-6-pyridyl)malondialdehyde (4.00 mg, 0.0200 mmol), potassium acetate (10 mg, 0.10 mmol) in acetic anhydride (1 mL) and acetic acid (1 mL) was heated at 130° C. for 3 h under nitrogen atmosphere. After cooling to ambient temperature the solvent was evaporated off under reduced pressure to give a dark blue solid, which was then subjected to reverse-phase HPLC (acetonitrile/0.1 M TEAB gradient) purification to give the product: 5c (8.93 umol, 44.7% yield, □max 645 nm).

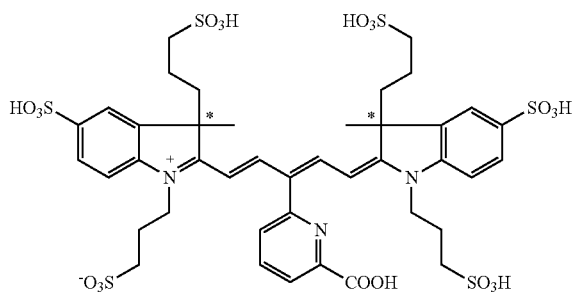

5d

Preparation of 5d

A solution of 2,3-dimethyl-1,3-bis(3-sulfopropyl)indoleninium-5-sulfonate (54.4 mg, 0.100 mmol), 2-(2-hydroxycarbonyl-6-pyridyl)malondialdehyde (9.86 mg, 0.0500 mmol), potassium acetate (35 mg, 0.35 mmol) in acetic anhydride (3 mL) and acetic acid (3 mL) was heated at 130° C. for 3 h under nitrogen atmosphere. After cooling to ambient temperature the solvent was evaporated off under reduced pressure to give a dark blue solid, which was then subjected to reverse-phase HPLC (acetonitrile/0.1 M TEAB gradient) purification to give two diastereomers of products: GS318-086A (more polar isomer, 3.65 umol, □max 650 nm) and 5d (less polar isomer, 4.72 umol, □max 653 nm).

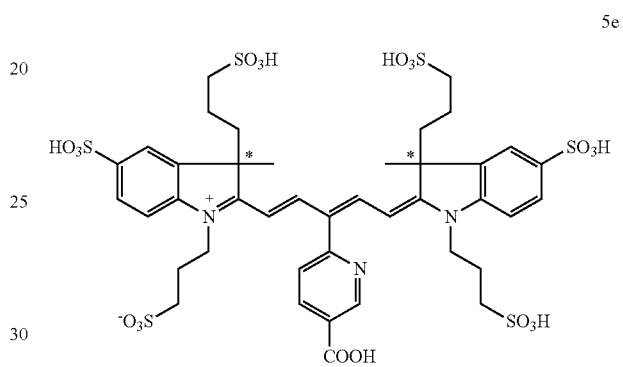

5e

Preparation of 5e

A solution of 2,3-dimethyl-1,3-bis(3-sulfopropyl)indoleninium-5-sulfonate (57.0 mg, 0.107 mmol), 2-(3-hydroxycarbonyl-6-pyridyl)malondialdehyde (10.0 mg, 0.0500 mmol), potassium acetate (35 mg, 0.35 mmol) in acetic anhydride (3 mL) and acetic acid (3 mL) was heated at 130° C. for 3 h under nitrogen atmosphere. After cooling to ambient temperature the solvent was evaporated off under reduced pressure to give a dark blue solid, which was then subjected to reverse-phase HPLC (acetonitrile/0.1 M TEAB gradient) purification to give two diastereomers of products: GS318-090A (more polar isomer, 4.23 umol, □max 650 nm) and 5e (less polar isomer, 4.93 umol, □max 650 nm).

5f

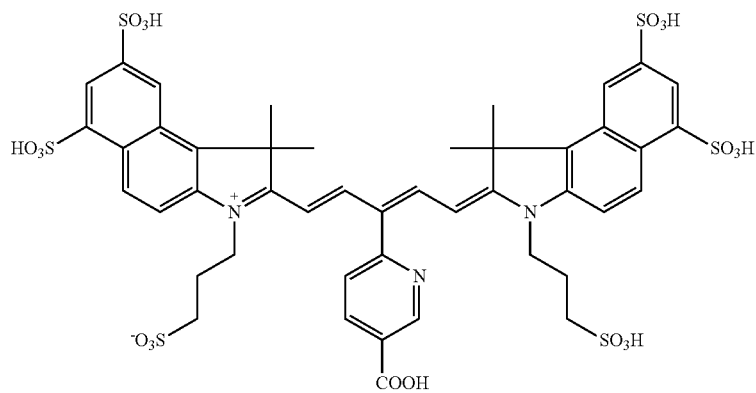

Preparation of 5f

A solution of 1,1,2-trimethyl-3-(3-sulfopropyl)benz[e]indolium-6,8-disulfonate (56.7 mg, 0.115 mmol), 2-(3-hydroxycarbonyl-6-pyridyl)malondialdehyde (11.2 mg, 0.0570 mmol), potassium acetate (35 mg, 0.35 mmol) in acetic anhydride (3 mL) and acetic acid (3 mL) was heated at 130° C. for 3 h under nitrogen atmosphere. After cooling to ambient temperature the solvent was evaporated off under reduced pressure to give a dark blue solid, which was then subjected to reverse-phase HPLC (acetonitrile/0.1 M TEAB gradient) purification to give the product: 5f (1.13 umol, □max 672 nm).

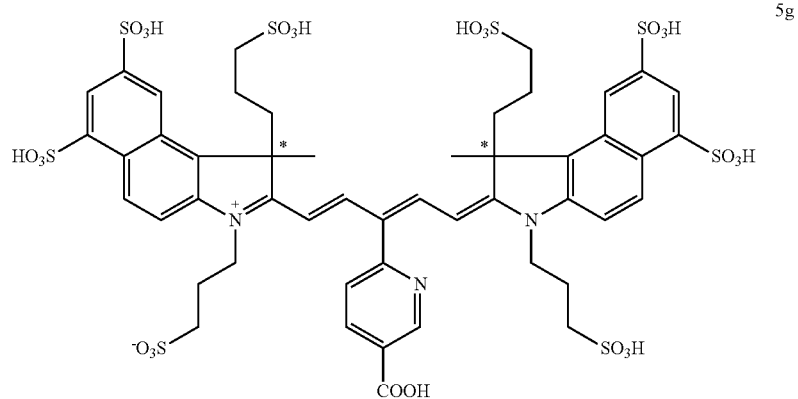

Preparation of 5g

A solution of 1,2-dimethyl-1,3-bis(3-sulfopropyl)benz[e]indole-6,8-disulfonate (121 mg, 0.170 mmol), 2-(3-hydroxycarbonyl-6-pyridyl)malondialdehyde (16 mg, 0.085 mmol), potassium acetate (50 mg, 0.51 mmol) in acetic anhydride (6 mL) and acetic acid (6 mL) was heated at 130° C. for 3 h under nitrogen atmosphere. After cooling to ambient temperature the solvent was evaporated off under reduced pressure to give a dark blue solid, which was then subjected to reverse-phase HPLC (acetonitrile/0.1 M TEAB gradient) purification to give two diastereomers of products: GS318-105A (more polar isomer, □max 680 nm) and 5g (less polar isomer, □max 678 nm).

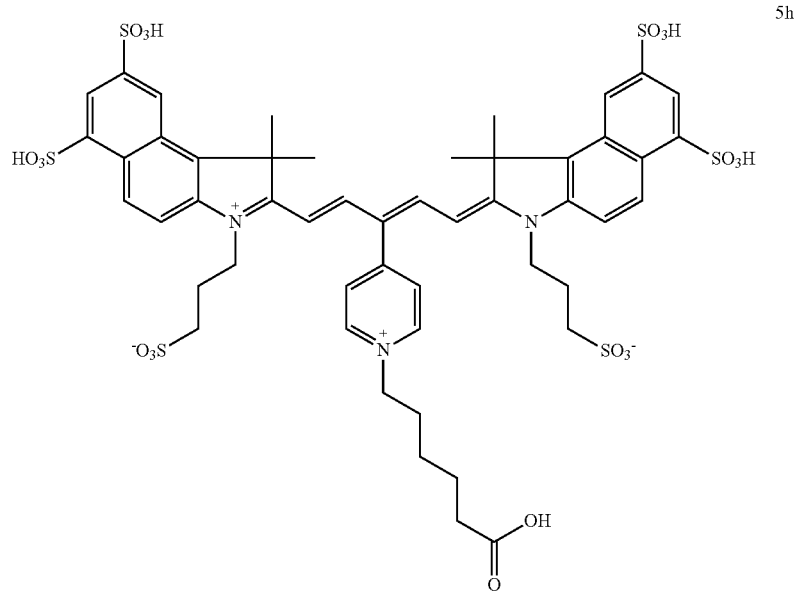

Preparation of 5h

A solution of 1,1,2-trimethyl-3-(3-sulfopropyl)benz[e]indolium-6,8-disulfonate (200 mg, 0.407 mmol), 2-(3-carboxypentyl-3-pyridyl)malondialdehyde (120 mg, 0.418 mmol), potassium acetate (20 mg, 0.20 mmol) in acetic anhydride (3 mL) and acetic acid (3 mL) was heated at 130° C. for 3 h under nitrogen atmosphere. After cooling to ambient temperature the solvent was evaporated off under reduced pressure to give a dark blue solid, which was then subjected to reverse-phase HPLC (acetonitrile/0.1 M TEAB gradient) purification to give the product: 5h (□max 666 nm).

Example 6

Scheme 1.

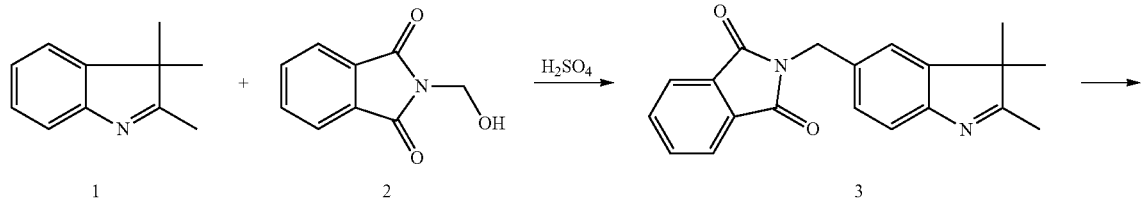

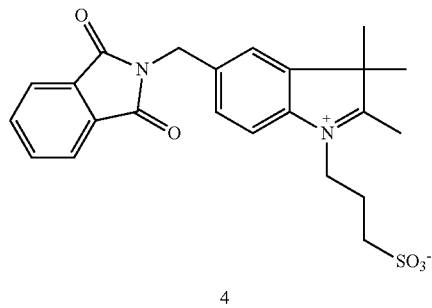

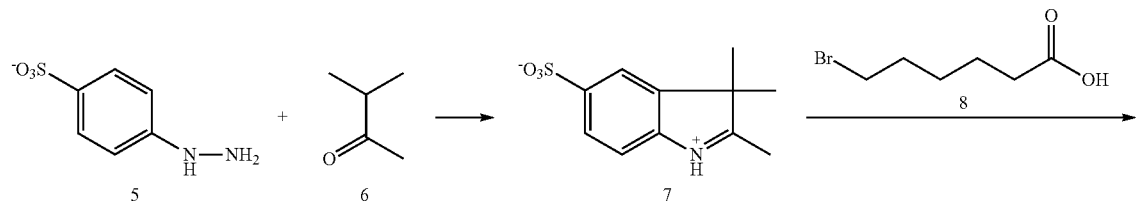

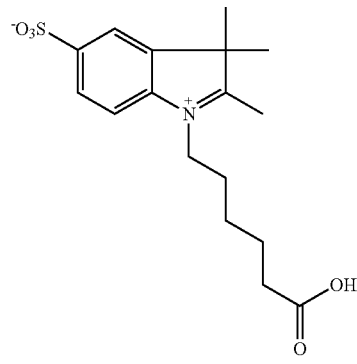

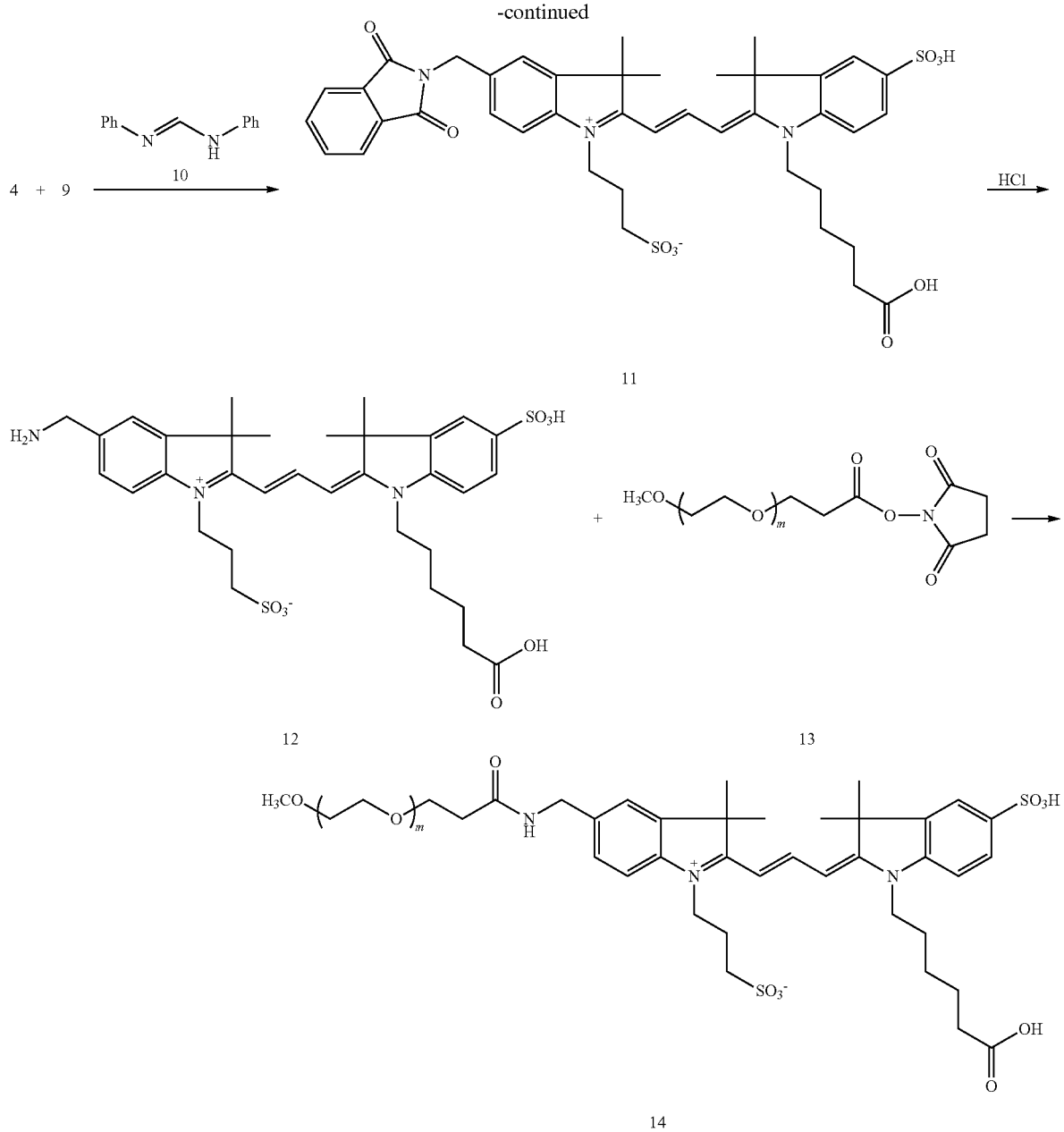

6.1 Synthesis of 5-phthalimidomethyl-2,3,3-trimethylindolenine (3)

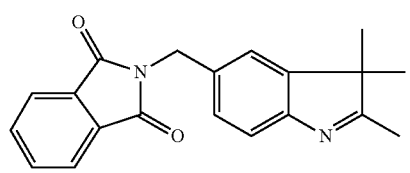

To an oven dried 500-mL round bottomed flask equipped with a stirring bar, a reflux condenser and a nitrogen balloon was added 2,3,3,-trimethylindolenine (50.0 g, 0.314 mol) and then concentrated sulfuric acid (260 mL) and stirred for 20 min. To it was added portionwise N-hydroxymethylphthalimide (50 g, 0.286 mol). The progress of the reaction was followed with TLC for the disappearance of the starting material and the appearance of the product. After stirring for 70 h the starting material was consumed completely and the solution was poured onto ice (500 g) and neutralized with concentrated ammonium hydroxide (900 mL). The resulting red precipitate was filtered, washed with water (3×100 mL) and dried. The product was then triturated with hexane (500 mL), filtered and dried to give a dark orange solid (87.22 g, 95.8%).

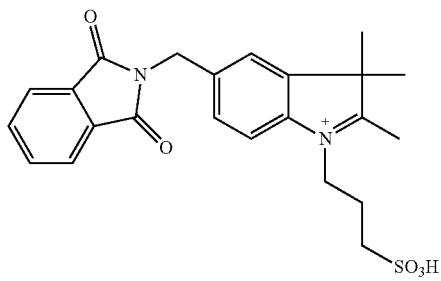

4

6.2 Synthesis of 5-phthalimidomethyl-1-(3-sulfonatopropyl)-2,3,3-trimethylindolenine (4)

A suspension of 5-phthalimidomethyl-2,3,3-trimethylindolenine (2.367 g, 7.436 mmol), 1,3-propanesultone (0.82 mL, 9.30 mmol) and 1,2-dichlorobenzene (15 mL) in 1,2-dichlorobenzene (20 mL) was heated in an oil bath at 140° C. under nitrogen atmosphere for 18 h. Removed oil bath and cooled the reaction solution to ambient temperature. Slowly added EtOAc (100 mL) and the solid were collected via filtration with the aid of EtOAc (2×50 mL). After brief drying the solid was dissolved in MeOH (70 mL). Added EtOAc (200 mL) and ethyl ether (200 mL). Collected the resultant solid, washed the solid with EtOAc (2×20 mL), Ethyl ether (2×20 mL) and air dried. Further drying of the solid under high vacuum at 50° C. overnight provided 3.13 g (96%) of a light pinkish solid.

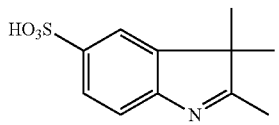

7

6.3 Synthesis of 2,3,3,-Trimethylindoleninium-5-sulfonate (7)

To an oven dried 500-mL round bottomed flask equipped with a stirring bar, a reflux condenser and a nitrogen balloon was add p-hydrazinobenzenesulfonic acid hemihydrate (50.0 g, 0.253 mol), acetic acid (150 mL), and 3-methyl-2-butanone (84 mL, 0.785 mol). Heated the reaction mixture with stirring in an oil bath at 115° C. for 4 h. Monitored the reaction with TLC (2:1 CH$_2$Cl$_2$:MeOH; starting material R$_f$=0.42, product R$_f$=0.69) until all starting material was consumed. Removed oil bath and cooled the reaction solution to ambient temperature. Slowly added EtOAc (~200 mL) and the resultant pink solid were collected via filtration with the aid of EtOAc (2×50 mL). After brief drying the solid was dissolved in MeOH (700 mL). Added KOH (15 g) in iPrOH (200 mL) to the above solution and stirred. Collected the resultant yellow solid via filtration. Washed the solid with iPrOH (2×100 mL), EtOAc (3×100 mL) and air dried. Placed the solid in two amber bottles and dried in a desiccator under high vacuum overnight. There was obtained 48.8 g (69.5%) of the desired product as a potassium salt.

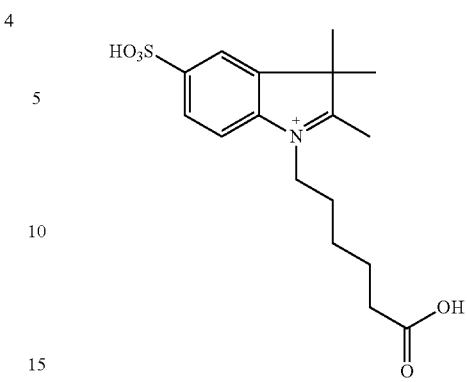

9

6.4 Synthesis of 1-carboxypentyl-2,3,3-trimethylindoleninium-5-sulfonate (9)

To an oven dried 250-mL round bottom flask equipped with a stir bar, condenser, and an argon balloon in an oil bath was added 2,3,3-trimethylindolenine-5-sulfonate (10 g, 36.05 mmol), bromohexanoic acid (8.78 g, 45.0 mmol) and 1,2-dichlorobenzene (100 mL). Heated the oil bath to 110° C. for 24 h. Monitored the reaction with TLC (2:1 CH$_2$Cl$_2$:MeOH) for the disappearance of starting material (R$_f$=0.69) and the formation of product (R$_f$=0.22). Removed oil bath and cooled the mixture to room temperature. Decanted the solvent and triturated the solid with iPrOH (100 mL). Collected the solid using filtration funnel. Re-dissolved the solid in MeOH (300 mL) and added iPrOH (700 mL) to precipitate the solid. The resultant solid was collected, washed with iPrOH (2×50 mL), EtOAc (2×50 mL), ether (2×50 mL) and air dried. The solid was placed in an amber bottle and dried in a desiccator under high vacuum overnight. There was obtained a total of 8.02 g (62%) of product.

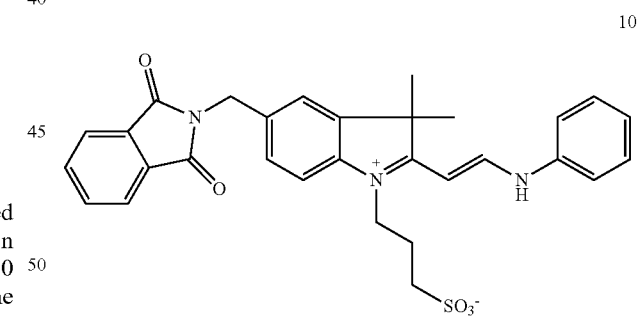

10

6.5 Synthesis of 2-[(1E)-2-Anilinoethenyl]-3,3-dimethyl-1-(3-sulfonatopropyl)-5-phthalimidomethyl-3H-indoleninium (10)

A mixture of 5-phthalimidomethyl-1-(3-sulfonatopropyl)-2,3,3-trimethylindolenine (503 mg, 1.14 mmol) and N,N'-diphenylformamidine (225 mg, 1.14 mmol) in acetic anhydride (5 mL) and acetic acid (3 mL) was heated in an oil bath at 125° C. for 6 h. Acetic acid was removed under reduced pressure and the residual dark solid was washed with ethyl ether (3×20 mL). The dried solid was used without further purification in the next reaction for carbocyanine dye synthesis.

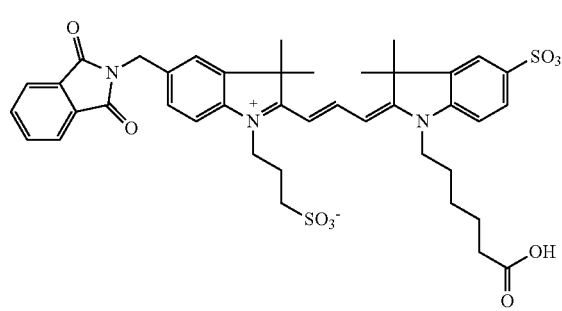

11

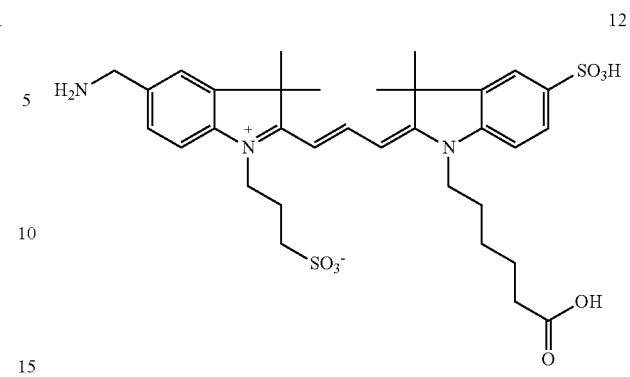

12

6.6 Synthesis of 5-phthalimidomethyl-5'-sulfonate-1-(3-sulfonatopropyl)-1-carboxypentyl Carbocyanine (11)

A mixture of 2-[(1E)-2-anilinoethenyl]-3,3-dimethyl-1-(3-sulfonatopropyl)-5-phthalimidomethyl-3H-indoleninium (1.14 mmol) and 1-carboxypentyl-2,3,3-trimethylindoleninium-5-sulfonate (363 mg, 1.03 mmol) in acetic anhydride (2 mL), pyridine (2 mL) was heated in a flask at 60° C. for 1 h. After cooling to room temperature added ethyl ether (500 mL) and the resultant solid was collected via filtration and washed with ethyl ether (2×20 mL) and dried to give 562 mg (68%) of the crude product of carbocyanine dye.

6.7 Synthesis of 5-aminomethyl-5'-sulfonate-1-(3-sulfonatopropyl)-1-carboxypentyl Carbocyanine (12)

A solution of the nitrogen protected carbocyanine from above (8.8 mg, 0.011 mmol) in concentrated hydrochloric acid (1 mL) was heated in an oil bath at 100° C. for 15 h. After cooling to room temperature added water (3 mL) to dilute the acid and neutralized with triethylamine until basic. The solution was concentrated to a small volume and then purified by reverse-phase HPLC (acetonitrile/0.1 M TEAB gradient) to give 7.9 umol (74%) of the desired product.

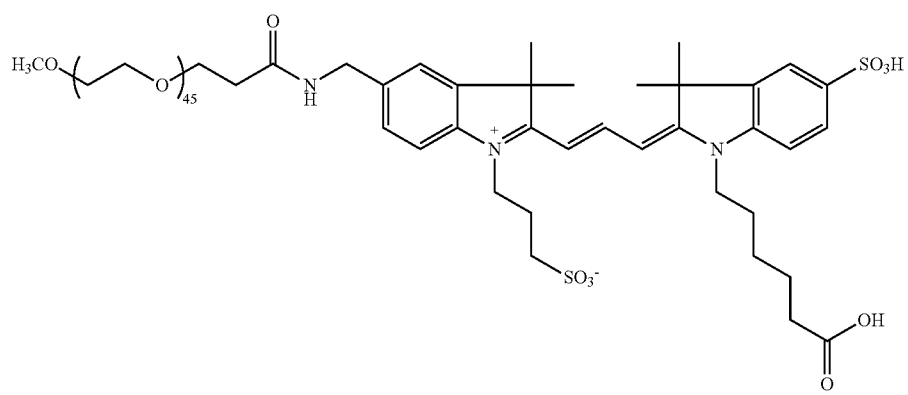

14

6.8 Synthesis of PEG (45)-carbocyanine (14)

A solution of the amino carbocyanine (1.5 umol) in water (100 uL) was added to the NHS dPEG ester (8.0 mg, 3.5 umol) in DMF (100 uL). The solution was kept in the dark at room temperature for 18 h and then purified with reverse-phase HPLC (acetonitrile/0.1 M TEAB gradient) to give the PEGlated carbocyanine in good yield.

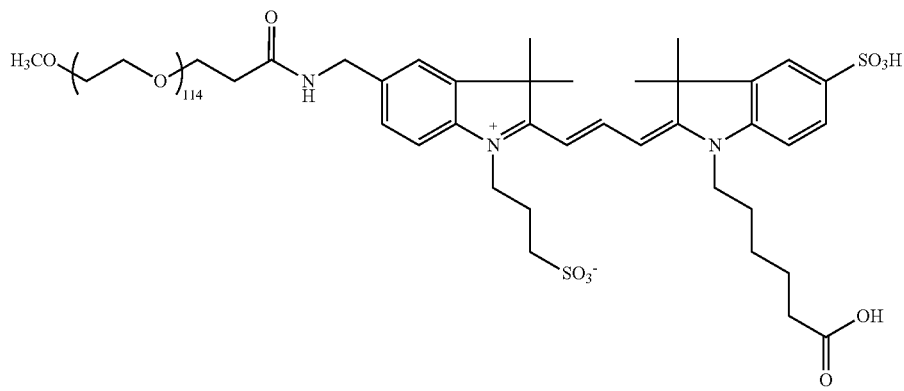
6.9 Synthesis of PEG (114)-carbocyanine (15)
A solution of the amino carbocyanine (1.5 umol) in water (100 uL) was added to the NHS dPEG ester (15.5 mg, 3.2 umol) in DMF (100 uL). The solution was kept in the dark at room temperature for 18 h and then purification with reverse-phase HPLC (acetonitrile/0.1 M TEAB gradient) to give the PEGlated carbocyanine in good yield.
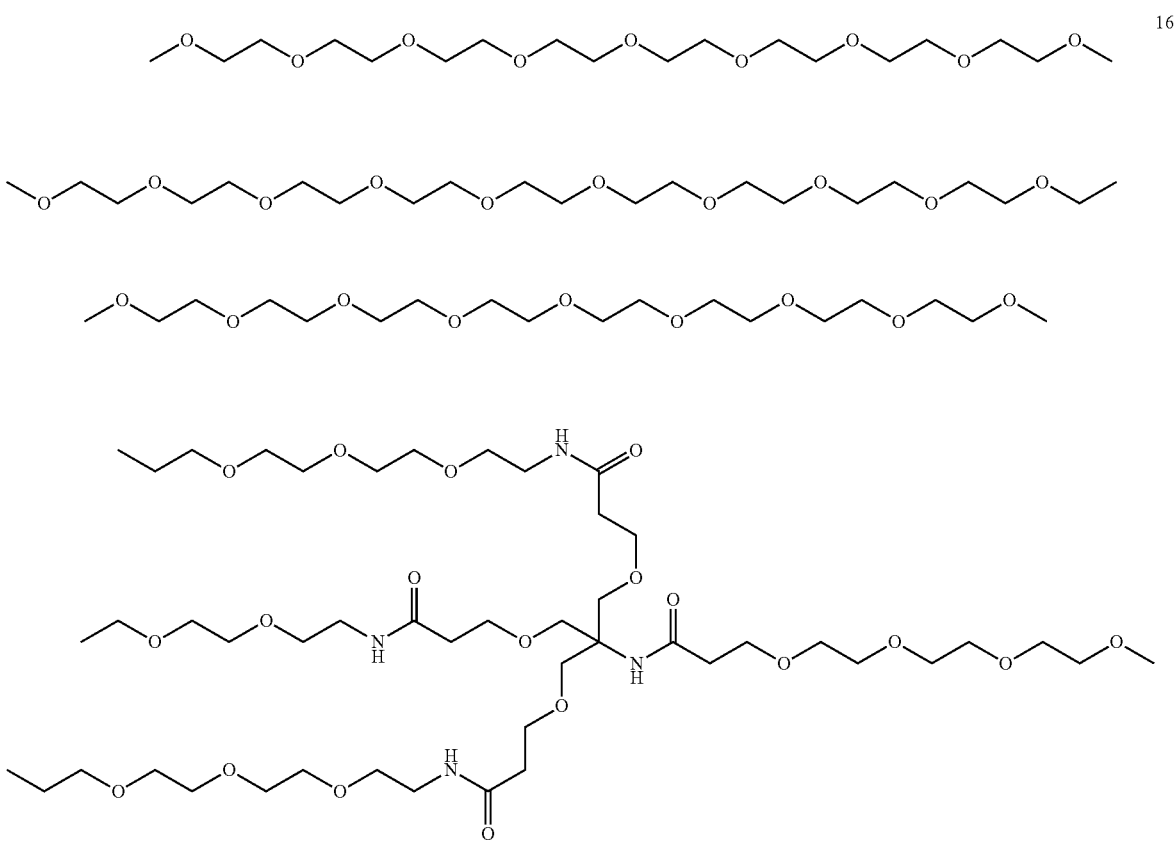

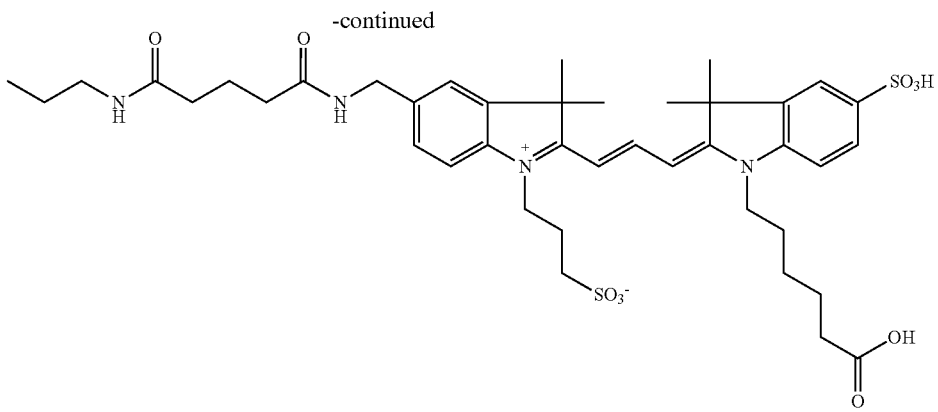

6.10 Synthesis of branched PEG (3×12)-carbocyanine

A solution of the amino carbocyanine (1.5 umol) in water (100 uL) was added to the NHS dPEG ester (14.0 mg, 5.8 umol) in DMF (100 uL). The solution was kept in the dark at room temperature for 18 h and then purification with reverse-phase HPLC (acetonitrile/0.1 M TEAB gradient) to give the PEGlated carbocyanine in good yield.

The present invention provides, inter alia, novel cyanine dyes, conjugates incorporating these dyes and method of using the dyes and conjugates. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A compound having the formula:

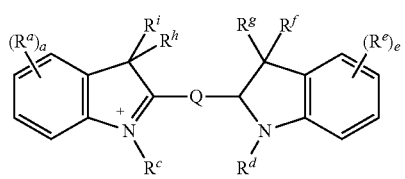

wherein
Q is:

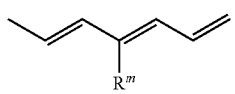

$R^m$ is a substituted or unsubstituted heteroaryl;

$R^c$, and $R^d$ are independently selected from alkyl and heteroalkyl, substituted with a member selected from sulfonic acid, carboxylic acid, phosphonic acid, and phosphoric acid;

each $R^a$ and each $R^e$, is independently selected from $C(O)R^9$, $OR^{12}$, $NR^{12}R^{13}$, $CR^{12}C(O)R^{13}$, $NR^{12}C(O)_2R^{13}$, $SO_3H$, and $C(O)NR^{12}R^{13}$, substituted or unsubstituted alkyl, substituted or unsubstituted heteroalkyl, substituted or unsubstituted aryl, substituted or unsubstituted heteroaryl, substituted or unsubstituted heterocycloalkyl, and a ring structure formed by joining a member selected from two $R^a$ moieties together with the atoms to which they are attached, two $R^e$ moieties together with the atoms to which they are attached, and a combination thereof, to form said ring structure, which is a member selected from a substituted or unsubstituted aryl and a substituted or unsubstituted heteroaryl, said ring substituted with at least one $SO_3H$, wherein
$R^9$ is a member selected from $OR^{10}$, and $NH(CH_2)_tOR^{11}$ wherein
$R^{10}$ is a member selected from H and substituted or unsubstituted alkyl;

t is selected from the integers from 1 to 12;

$R^{11}$ is a member selected from H, and

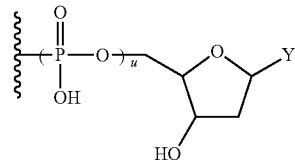

wherein
u is selected from the integers from 1 to 8; and
Y is a nucleobase; and $R^{12}$ and $R^{13}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

a and e are integers independently selected from 0, 1, 2, 3 and 4;

$R^f$, $R^g$, $R^h$, and $R^i$ are independently selected from unsubstituted alkyl, alkylsulfonic acid, and

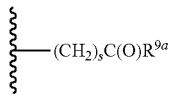

wherein
  s is selected from the integers from 1 to 12; and
  $R^{9a}$ is a member selected from OH, and

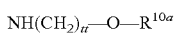

wherein
  tt is selected from the integers from 1 to 12; and
  $R^{10a}$ is a member selected from H, a moiety comprising poly(ethylene glycol), and

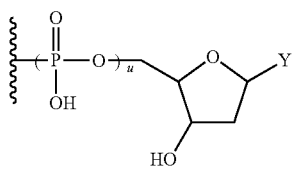

wherein
  Y is a nucleobase; and
  u is selected from the integers from 1 to 8.

2. The compound according to claim 1 wherein at least two of $R^f$, $R^g$, $R^h$, and $R^i$ are alkylsulfonic acid.

3. The compound according to claim 1 wherein neither $R^c$ nor $R^d$ is unsubstituted alkyl.

4. The compound according to claim 1 wherein when two $R^a$ moieties are not joined to form said ring substituted with said at least one $SO_3H$ moiety, at least one $R^a$ is $SO_3H$.

5. The compound according to claim 1 wherein when two $R^e$ moieties are not joined to form said aryl ring substituted with said at least one $SO_3H$ moiety, at least one $R^e$ is $SO_3H$.

6. The compound according to claim 1 wherein two $R^a$ moieties are joined, providing said compound with the substructure:

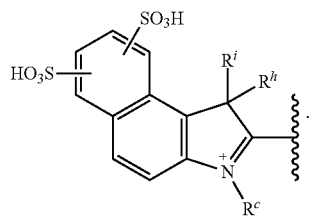

7. The compound according to claim 1 wherein two $R^e$ moieties are joined, providing said compound with the substructure:

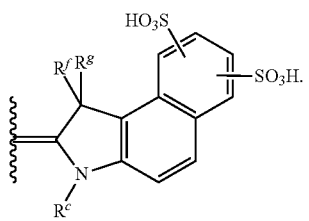

8. The compound according to claim 1 having the formula:

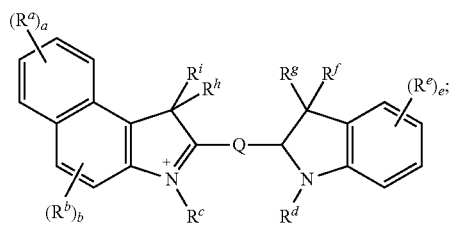

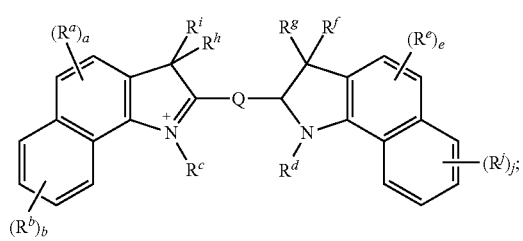

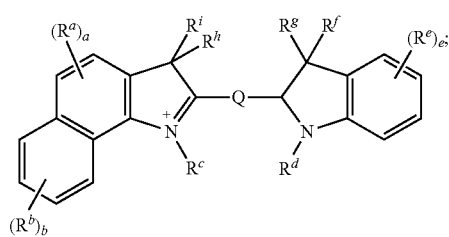

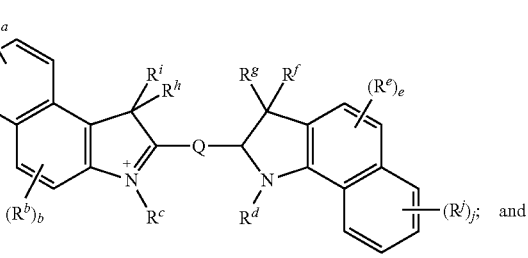

and

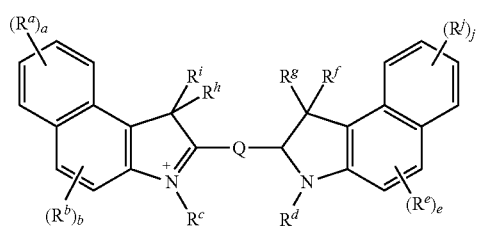

wherein
  each $R^b$ and each $R^j$ are members independently selected from $C(O)R^{29}$, $OR^{32}$, $NR^{32}R^{33}$, $CR^{32}C(O)R^{33}$, $NR^{32}C(O)_2R^{33}$, $SO_3H$, and $C(O)NR^{32}R^{33}$, substituted or unsubstituted alkyl, substituted or unsubstituted heteroalkyl, substituted or unsubstituted aryl, substituted or unsubstituted heteroaryl, substituted or unsubstituted heterocycloalkyl wherein R²⁹ is a member selected from OR³¹, and NH(CH₂)ₜ'OR³⁰ wherein

R³¹ is a member selected from H and substituted or unsubstituted alkyl;

t' is selected from the integers from 1 to 12;

R³⁰ is a member selected from H, and

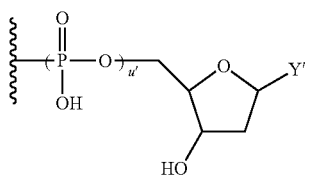

wherein u' is selected from the integers from 1 to 8; and

Y is a nucleobase;

R³² and R³³ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

9. The compound according claim 1 having the formula:

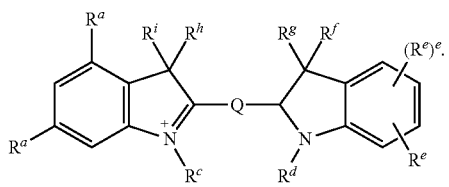

10. The compound according to claim 1 having the formula:

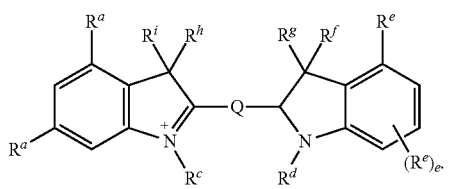

11. The compound according to claim 1 having the formula:

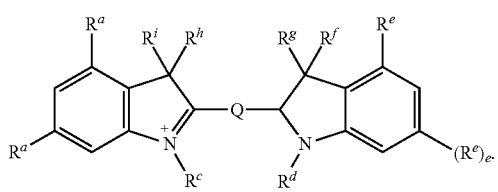

12. The compound according to claim 1 having the formula:

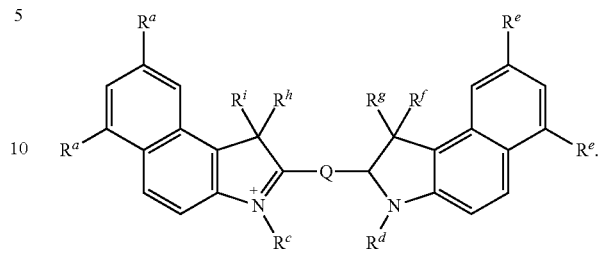

13. The compound according to claim 1 wherein $R^a$, and $R^e$ are independently selected from:

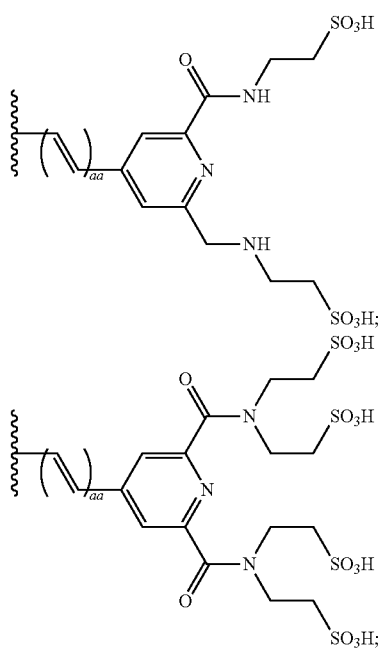

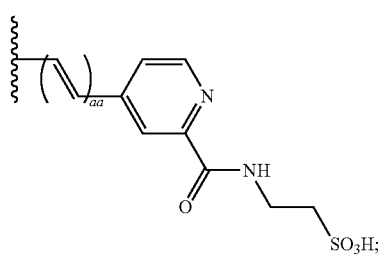

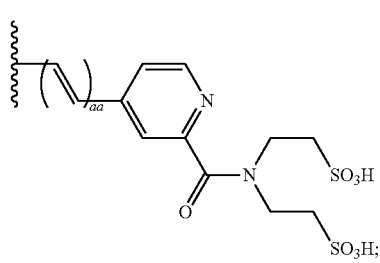

-continued

[chemical structures]

in which
aa is 0 or 1;
x is an integer selected from 0, 1, 2, 3, 4, 5, 6, 7, 8, 9, and 10;
n is an integer which provides a polyethylene glycol moiety of molecular weight of at least about 100;

$R^p$ is selected from H, substituted or unsubstituted alkyl and substituted or unsubstituted heteroalkyl;

$R^{33}$ is a member selected from H, COOH,

[chemical structures: -C(O)NHCH₂CH₂SO₃H; and -C(O)N(CH₂CH₂SO₃H)₂;]

and $R^8$ is a member selected from H, substituted or unsubstituted alkyl and substituted or unsubstituted heteroalkyl.

14. The compound according to claim 1 wherein $R^m$ has a formula:

[chemical structure with C(O)R¹²]

wherein
Z is N;
$R^{12}$ is a member selected from OH, and $-NH(CH_2)_{t'}-O-R^{10'}$ wherein
t' is selected from the integers from 1 to 12;
$R^{10'}$ is a member selected from H, a moiety comprising poly(ethylene glycol), and

[chemical structure with phosphate, sugar, Y']

wherein
u' is selected from the integers from 1 to 8; and
Y' is a nucleobase.

15. The compound according to claim 1 wherein $R^m$ has the formula:

[pyridine structure with C(O)R¹²].

16. The compound according to claim 1 wherein $R^m$ is a member selected from:

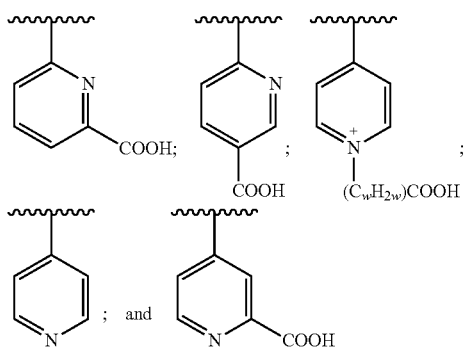

in which w is an integer selected from 1, 2, 3, 4, 5, 6, 7, 8, 9, 10 or greater.

17. The compound according to claim 1 wherein 1, 2, 3 or 4 of $R^f$, $R^g$, $R^h$, $R^i$, $R^c$ and $R^d$ is:

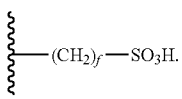

18. The compound according to claim 1 wherein both $R^c$ and $R^d$ are:

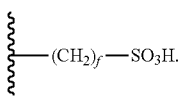

19. The compound according to claim 1 in which two, three, four, five or six of $R^a$, $R^e$, $R^c$, $R^d$, $R^f$, $R^g$, $R^h$, Ri, and $R^m$ in any combination, include an independently selected $R^{11}$ moiety which is:

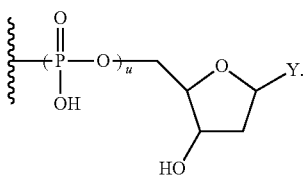

20. The compound according to claim 1 in which two, three, four, five or six of $R^a$, $R^e$, $R^c$, $R^d$, $R^f$, $R^g$, $R^h$, Ri, and $R^m$ in any combination, include an independently selected dye moiety or dye linker moiety.

21. The compound according to claim 1 in which two, three, four-, five or six of $R^a$, $R^e$, $R^j$, $R^c$, $R^d$, $R^f$, $R^g$, $R^h$, Ri, and $R^m$ in any combination, include an independently selected polyvalent moiety.

22. The compound according to claim 21 wherein said polyvalent moiety has bound thereto one or more member selected from a dye, a dye-linker moiety, and a nucleotide polyphosphate.

23. A method of monitoring an enzyme reaction, said method comprising:

(a) forming a reaction mixture by contacting said enzyme with a fluorescent dye that is a compound having the formula:

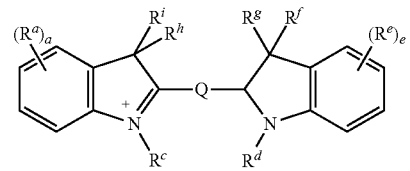

wherein
Q is:

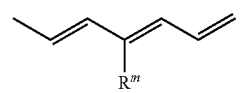

$R^m$ is a member selected from substituted or unsubstituted aryl and substituted or unsubstituted heteroaryl;

$R^c$, and $R^d$ are independently selected from alkyl and heteroalkyl, substituted with a member selected from sulfonic acid, carboxylic acid, phosphonic acid, and phosphoric acid;

each $R^a$ and each $R^e$, is independently selected from $C(O)R^9$, $OR^{12}$, $NR^{12}R^{13}$, $CR^{12}C(O)R^{13}$, $NR^{12}C(O)_2R^{13}$, $SO_3H$, and $C(O)NR^{12}R^{13}$, substituted or unsubstituted alkyl, substituted or unsubstituted heteroalkyl, substituted or unsubstituted aryl, substituted or unsubstituted heteroaryl, substituted or unsubstituted heterocycloalkyl, and a ring structure formed by joining a member selected from two $R^a$ moieties together with the atoms to which they are attached, two $R^e$ moieties together with the atoms to which they are attached, and a combination thereof, to form said ring structure, which is a member selected from a substituted or unsubstituted aryl and a substituted or unsubstituted heteroaryl, said ring substituted with at least one $SO_3H$ wherein
$R^9$ is a member selected from $OR^{10}$, and $NH(CH_2)_tOR^{11}$
wherein
$R^{10}$ is a member selected from H and substituted or unsubstituted alkyl;
t is selected from the integers from 1 to 12;
$R^{11}$ is a member selected from H, and

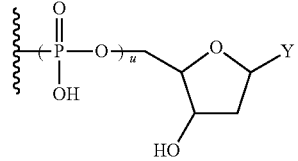

wherein
u is selected from the integers from 1 to 8; and
Y is a nucleobase; and
$R^{12}$ and $R^{13}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

a and e are integers independently selected from 0, 1, 2, 3 and 4;

$R^f$, $R^g$, $R^h$, and $R^i$ are independently selected from unsubstituted alkyl, alkylsulfonic acid, and

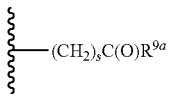

wherein
s is selected from the integers from 1 to 12; and
$R^{9a}$ is a member selected from OH, and

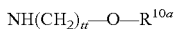

wherein
tt is selected from the integers from 1 to 12; and
$R^{10a}$ is a member selected from H, a moiety comprising poly(ethylene glycol), and

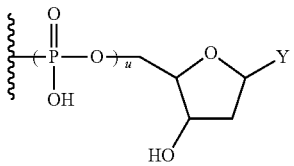

wherein
Y is a nucleobase; and
u is selected from the integers from 1 to 8;
comprising at least one nucleoside phosphate wherein said dye is a substrate for said enzyme under conditions sufficient for said enzyme and said dye to react; and
(b) monitoring fluorescence of said reaction mixture.

24. The method according to claim 23 wherein said enzyme is a DNA polymerase and said dye comprises a nucleic acid moiety which is said substrate for said enzyme.

25. The method according to claim 23 wherein said enzyme reaction is template directed DNA synthesis.

26. The method according to claim 23 wherein said reaction is a component of a single molecule DNA sequencing analysis.

27. The compound according to claim 8 wherein $R^b$ and $R^j$ are independently selected from:

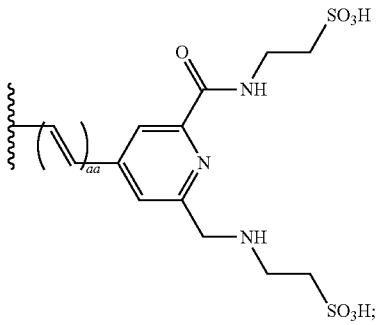

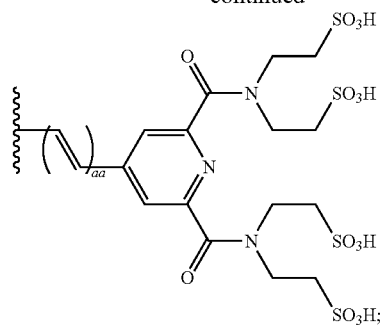

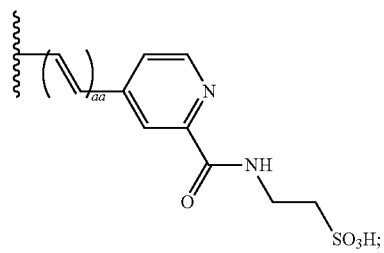

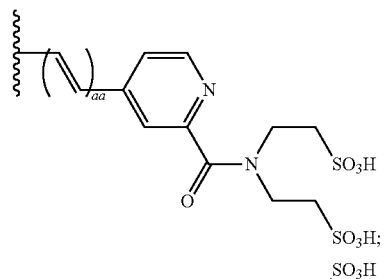

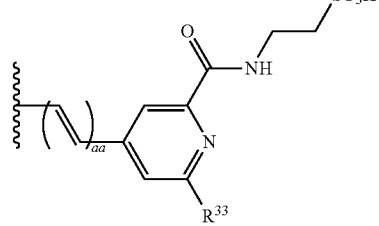

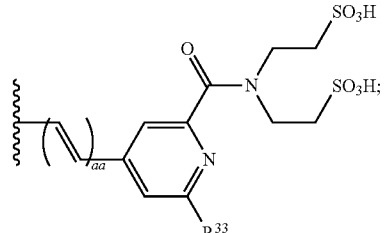

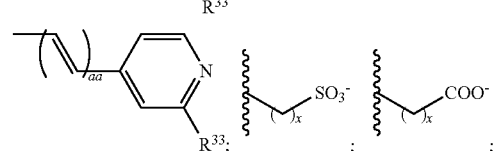

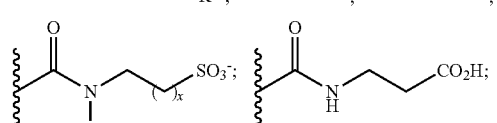

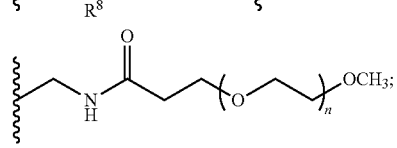

-continued

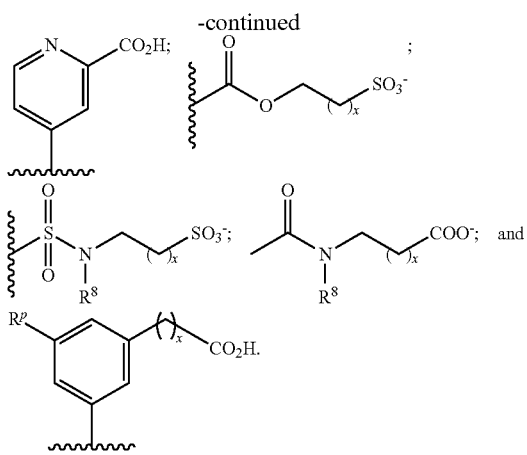

in which
aa is 0 or 1;
x is an integer selected from 0, 1, 2, 3, 4, 5, 6, 7, 8, 9, and 10;
n is an integer which provides a polyethylene glycol moiety of molecular weight at least about 100;
$R^p$ is selected from H, substituted or unsubstituted alkyl and substituted or unsubstituted heteroalkyl;
$R^{33}$ is a member selected from H, COOH,

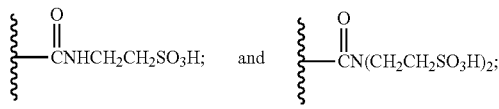

and $R^8$ is a member selected from H, substituted or unsubstituted alkyl and substituted or unsubstituted heteroalkyl.

28. The compound according to claim 8 in which two, three, four, five or six of $R^b$ and $R^j$ in any combination, include an independently selected $R^{11}$ moiety which is:

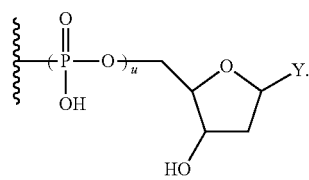

29. The compound according to claim 8 in which two, three, four, five or six of $R^b$ and $R^j$ in any combination, include an independently selected dye moiety or dye linker moiety.

30. The compound according to claim 8 in which two, three, four, five or six of $R^b$ and $R^j$ in any combination, include an independently selected polyvalent moiety.

31. The compound according to claim 30 wherein said polyvalent moiety has bound thereto one or more member selected from a dye, a dye-linker moiety, and a nucleotide polyphosphate.

* * * * *